US008895242B2

(12) United States Patent
Messmer

(10) Patent No.: US 8,895,242 B2
(45) Date of Patent: Nov. 25, 2014

(54) SINGLE MOLECULE NUCLEIC ACID NANOPARTICLES

(75) Inventor: Bradley T. Messmer, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 24 days.

(21) Appl. No.: 13/502,729

(22) PCT Filed: Oct. 19, 2010

(86) PCT No.: PCT/US2010/053270
§ 371 (c)(1),
(2), (4) Date: Jun. 28, 2012

(87) PCT Pub. No.: WO2011/050000
PCT Pub. Date: Apr. 28, 2011

(65) Prior Publication Data
US 2012/0263783 A1 Oct. 18, 2012

Related U.S. Application Data

(60) Provisional application No. 61/279,408, filed on Oct. 20, 2009.

(51) Int. Cl.
C12Q 1/68 (2006.01)
C07H 21/00 (2006.01)
A61K 31/7088 (2006.01)
A61K 9/51 (2006.01)
A61K 31/704 (2006.01)
A61K 39/385 (2006.01)
B82Y 5/00 (2011.01)
C12N 15/11 (2006.01)
A61K 39/00 (2006.01)
G01N 15/00 (2006.01)

(52) U.S. Cl.
CPC ........... A61K 31/7088 (2013.01); A61K 9/5146 (2013.01); A61K 31/704 (2013.01); A61K 39/385 (2013.01); B82Y 5/00 (2013.01); C12N 15/111 (2013.01); A61K 2039/64 (2013.01); C12N 2310/16 (2013.01); C12N 2310/315 (2013.01); C12N 2310/51 (2013.01); C12N 2330/31 (2013.01); C12N 2330/50 (2013.01); G01N 2015/0038 (2013.01)
USPC .......... 435/6.1; 435/6.11; 435/6.12; 424/450; 536/22.1

(58) Field of Classification Search
None
See application file for complete search history.

(56) References Cited

U.S. PATENT DOCUMENTS

2002/0106647 A1* 8/2002 Segal et al. ........................ 435/6
2006/0088864 A1* 4/2006 Smolke et al. ..................... 435/6
2009/0082217 A1* 3/2009 Smolke et al. ..................... 506/9
2009/0191170 A1* 7/2009 Segal et al. ................. 424/93.21
2010/0081128 A1* 4/2010 Drmanac et al. .................. 435/6
2012/0252699 A1* 10/2012 Jaffrey et al. .................... 506/16

FOREIGN PATENT DOCUMENTS

WO WO 03/048298 6/2003
WO WO 2008/039254 4/2008

OTHER PUBLICATIONS

Guo, RNA nanotechnology: engineering, assembly and applications in detection, gene delivery and therapy, J. Nanosci. Nanotechnol., Dec. 2005, vol. 5, No. 12, pp. 1964-1982).*
Bagalkot et al. (An Aptamer-Doxorubicin Physical Conjugate as a Novel Targeted Drug-Delivery Platform, Angew. Chem. Int. Ed. 2006, 45, 8149-8152).*
Merrium Webster, acessed on Apr. 2, 2013 at http://www.merriam-webster.com/dictionary/plural.*
Cho et al. (Applications of Aptamers as Sensors, Annu. Rev. Anal. Chem. 2009. 2:241-64).*
Zhao et al. (Rolling Circle Amplification: Applications in Nanotechnology and Biodetection with Functional Nucleic Acids, Angew. Chem. Int. Ed., Aug. 4, 2008, 47, 6330-6337).*
Simonova et al. (Enhanced cellular binding of concatemeric oligonucleotide complexes, Biochimica et Biophysica Acta 1758 (2006) 413-418).*
Wu et al. (Selection of Oligonucleotide Aptamers with Enhanced Uptake and Activation of Human Leukemia B Cells, Human Gene Therapy 14:849-860 (Jun. 10, 2003)).*
Gronostajski et al., Site-specific DNA binding of nuclear factor I: effect of the spacer region, Nucleic Acids Research, vol. 14, No. 14, 1987.*
Fire et al., Rolling replication of short DNA circles, Proc. Natl. Acad. Sci. USA, vol. 92, 1995.*
Kutter et al., Molecular Mechanisms of Phage Infection, in Bacteriophages: Biology and Applications, Eds. Kutter et al., Ch. 7, 2004.*
Friedrichs et al., Nucleic-Acid-Based Switches, in Molecular Switches, Second Ed. 2011, Eds. Feringa & Browne, Ch. 7.*

(Continued)

Primary Examiner — Christopher M Babic
Assistant Examiner — Aaron Priest
(74) Attorney, Agent, or Firm — Knobbe Martens Olson & Bear LLP

(57) ABSTRACT

The present technology relates to a nanoparticle platform based on the unique and varied properties of DNA. Circular DNA can be replicated using a strand displacing polymerase to generate long linear concatamers of controllable length that spontaneously fold into a ball conformation due to internal base-pairing. These balls of DNA are discreet particles that can be made in variable sizes on a nanometer size scale in a scalable manner. The particles can be used in a variety of manners, discussed herein, including specific targeting, drug delivery to cancer cells, and diagnostics. Nanoparticles may also serve as multifunctional platforms for the integration of many currently used cancer therapeutic techniques.

40 Claims, 66 Drawing Sheets

(56) References Cited

OTHER PUBLICATIONS

Guo, P., "RNA nanotechnology: engineering, assembly and applications in detection, gene delivery and therapy," J. Nanosci. Nanotechnol., Dec. 2005, vol. 5, No. 12, pp. 1964-1982.
Steiner, J.M., et al., DeNAno: Selectable deoxyribonucleic acid nanoparticle libraries, J. of Biotechnol., Dec. 4, 2009, vol. 145, No. 4, pp. 330-333.
International Search Report and Written Opinion issued on Jul. 29, 2011 for International application No. PCT/US2010/053270.
Anraku M, Cunningham KS, Yun Z, Tsao MS, Zhang L, Keshavjee S, Johnston MR, de Perrot M (2008) Impact of tumor-infiltrating T cells on survival in patients with malignant pleural mesothelioma. J Thorac Cardiovasc Surg 135: 823-9.
Ardavin C (2003) Origin, precursors and differentiation of mouse dendritic cells. Nat Rev Immunol 3: 582-90.
Austin R (2003) Nanopores: The art of sucking spaghetti. Nat Mater 2: 567-8.
Bagalkot et al., An aptamer-doxorubicin physical conjugate as a novel targeted drug-delivery platform. Angew Chem Int Ed Engl. 2006;45:8149-8152.
Banchereau J, Steinman RM (1998) Dendritic cells and the control of immunity. Nature 392: 245-52.
Bartel, D.P. & Szostak, J.W. Isolation of new ribozymes from a large pool of random sequences [see comment]. Science 261, 1411-1418 (1993).
Becker Y, (1992) Anticancer role of dendritic cells (DC) in human and experimental cancers—a review. Anticancer Res 12: 511-20.
Beriou G, Peche H, Guillonneau C, Merieau E, Cuturi MC (2005) Donor-specific allograft tolerance by administration of recipient-derived immature dendritic cells and suboptimal immunosuppression. Transplantation 79: 969-72.
Berti L, et al. DNA-Templated Photoinduced Silver Deposition J. Am. Chem. Soc. 2005;127:11216-11217.
Blab, G.A., Schmidt, T. & Nilsson, M. Homogeneous detection of single rolling circle replication products. Anal. Chem., 2004, 76, 495-498.
Blair SL, et al., Enhanced touch preps improve the ease of interpretation of intraoperative breast cancer margins. Am Surg. 2007;73:973-976.
Boisgerault et al., (2005) Cross-priming of T cell responses by synthetic microspheres carrying a CD8+ T cell epitope requires an adjuvant signal. J Immunol 174: 3432-9.
Bomford R (1998) Will adjuvants be needed for vaccines of the future? Dev Biol Stand 92: 13-7.
Bonifaz et al., (2004) In vivo targeting of antigens to maturing dendritic cells via the DEC-205 receptor improves T cell vaccination. J Exp Med 199: 815-24.
Bourquin et al., (2008) Targeting CpG oligonucleotides to the lymph node by nanoparticles elicits efficient antitumoral immunity. J Immunol 181: 2990-8.
Brazolot Millan CL et al., (1998) CpG DNA can induce strong Th1 humoral and cell-mediated immune responses against hepatitis B surface antigen in young mice. Proc Natl Acad Sci U S A 95: 15553-8.
Breaker et al., A DNA enzyme that cleaves RNA. Chem Biol. 1994;1:223-229.
Clackson et al., Making antibody fragments using phage display libraries. Nature, 1991, 352, 624-628.
Clemente et al., (1996) Prognostic value of tumor infiltrating lymphocytes in the vertical growth phase of primary cutaneous melanoma. Cancer 77: 1303-10.
Cortes-Mateos MJ, et al. Automated microscopy to evaluate surgical specimens via touch prep in breast cancer. Ann Surg Oncol. 2009;16:709-720.
Davenport et al., (1996) Analysis of peptide-binding motifs for two disease associated HLA-DR13 alleles using an M13 phage display library. Immunology 88: 482-6.
De Jong et al., (2007) Encapsulation in liposomal nanoparticles enhances the immunostimulatory, adjuvant and anti-tumor activity of subcutaneously administered CpG ODN. Cancer Immunol Immunother 56: 1251-64.
Diederichsen et al., (2003) Prognostic value of the CD4+/CD8+ ratio of tumour infiltrating lymphocytes in colorectal cancer and HLA-DR expression on tumour cells. Cancer Immunol Immunother 52: 423-8.
Ellington et al., In vitro selection of RNA molecules that bind specific ligands. Nature, 1990, 346, 818-822.
Farokhzad et al., Targeted nanoparticle-aptamer bioconjugates for cancer chemotherapy in vivo. Proc Natl Acad Sci U S A. 2006;103:6315-6320.
Ferrari, M. Cancer nanotechnology: opportunities and challenges. Nat Rev Cancer, 2005, 5, 161-171.
Fichou et al., The potential of oligonucleotides for therapeutic applications. Trends Biotechnol. 2006;24:563-570.
Figdor CG, et al., Dendritic cell immunotherapy: mapping the way. Nat Med, 2004, 10: 475-80.
Finn OJ (2003) Cancer vaccines: between the idea and the reality. Nat Rev Immunol 3: 630-41.
Fong et al., Dendritic cells in cancer immunotherapy. Annu Rev Immunol, 2000, 18, 245-273.
Galon et al., (2006) Type, density, and location of immune cells within human colorectal tumors predict clinical outcome. Science 313: 1960-4.
Gilboa E (2004) The promise of cancer vaccines. Nat Rev Cancer 4: 401-11.
Gilliet et al., (2002) The development of murine plasmacytoid dendritic cell precursors is differentially regulated by FLT3-ligand and granulocyte/macrophage colony-stimulating factor. J Exp Med 195: 953-8.
Golding B (1991) Cytokine regulation of of humoral immune responses. CRC Press, Boca Raton, FL.
Gram H, et al. In vitro selection and affinity maturation of antibodies from a naive combinatorial immunoglobulin library. Proc Natl Acad Sci U S A. 1992;89:3576-3580.
Gresser I (1987) A. Chekhov, M.D., and Coley's toxins. N Engl J Med 317: 457.
Gupta et al., (1994) Comparison of adjuvant activities of aluminium phosphate, calcium phosphate and stearyl tyrosine for tetanus toxoid. Biologicals 22: 53-63.
Henderson et al., (2005) Cancer vaccines and immunotherapies: emerging perspectives. Vaccine 23: 2359-62.
Herr et al., (2008) History of bacillus Calmette-Guerin and bladder cancer: an immunotherapy success story. J Urol 179: 53-6.
Hicke BJ, et al., (2001) Tenascin-C aptamers are generated using tumor cells and purified protein. J Biol Chem 276: 48644-54.
Hipp et al., (2000) Cancer vaccines: an update. In Vivo 14: 571-85.
Huang, et al., Aptamer-modified gold nanoparticles for colorimetric determination of platelet-derived growth factors and their receptors. Anal. Chem. 77, 2005, 5735-5741.
Hwu et al., (2002) The immunotherapy of patients with ovarian cancer. J Immunother 25: 189-201.
Inaba et al., (1992) Generation of large numbers of dendritic cells from mouse bone marrow cultures supplemented with granulocyte/macrophage colony-stimulating factor. The Journal of Experimental Medicine 176: 1693-702.
Inaba K, et al., (1993) Granulocytes, macrophages, and dendritic cells arise from a common major histocompatibility complex class II-negative progenitor in mouse bone marrow. Proc Natl Acad Sci U S A 90: 3038-42.
Irving RA, et al. Affinity maturation of recombinant antibodies using E. coli mutator cells. Immunotechnology. 1996;2:127-143.
Jarvius J, et al. Digital quantification using amplified single-molecule detection. Nat Methods, 2006, 3: 725-7.
Jones et al., (2002) Bacterial motif DNA as an adjuvant for the breakdown of immune self-tolerance to pyruvate dehydrogenase complex. Hepatology (Baltimore, Md.) 36: 679-86.
Kato et al., (1984) Adjuvant activity of Klebsiella O3 lipopolysaccharide: comparative study using defined uniform salt forms. Microbiology and Immunology 28: 659-66.
Kido et al., (1985) Potent adjuvant action of lipopolysaccharides possessing the O-specific polysaccharide moieties consisting of mannans in antibody response against protein antigen. Cellular Immunology 91: 52-9.

(56) References Cited

OTHER PUBLICATIONS

Kleindienst et al., (2005) Simultaneous induction of CD4 T cell tolerance and CD8 T cell immunity by semimature dendritic cells. J Immunol 174: 3941-7.

Klinman DM. Adjuvant activity of CpG oligodeoxynucleotides. Int Rev Immunol. 2006;25:135-154.

Knutson et al, (2001) Immunization with a HER-2/neu helper peptide vaccine generates HER-2/neu CD8 T-cell immunity in cancer patients. J Clin Invest 107: 477-84.

Kortt AA, et al. Dimeric and trimeric antibodies: high avidity scFvs for cancer targeting. Biomol Eng. 2001;18:95-108.

Krieg AM (2006) Therapeutic potential of Toll-like receptor 9 activation. Nat Rev Drug Discov 5: 471-84.

Ladanyi et al., (2007) Density of DC-LAMP(+) mature dendritic cells in combination with activated T lymphocytes infiltrating primary cutaneous melanoma is a strong independent prognostic factor. Cancer Immunol Immunother 56: 1459-69.

Larsson et al., (2000) Requirement of mature dendritic cells for efficient activation of influenza A-specific memory CD8+ T cells. J Immunol 165: 1182-90.

Larsson, C. et al. In situ genotyping individual DNA molecules by target-primed rolling-circle amplification of padlock probes. Nat Methods , 2004, 1, 227-232.

Lund J, et al. DNA Networks as Templates for Bottom-Up Assembly of Metal Nanowires. 5th IEEE Conference on Nanotechnology. Nagoya, Japan; 2005:836-840.

Mallikaratchy P, et al. Aptamer directly evolved from live cells recognizes membrane bound immunoglobin heavy mu chain in Burkitt's lymphoma cells. Mol Cell Proteomics. 2007;6:2230-2238.

Mantovani et al., (1992) The origin and function of tumor-associated macrophages. Immunol Today 13: 265-70.

Minev BR, et al., (2000) Synthetic insertion signal sequences enhance MHC class I presentation of a peptide from the melanoma antigen MART-1. Eur. J. Immunol. 30: 2115-2124.

Minev et al., (1999) Cancer vaccines: novel approaches and new promise. Pharmacol Ther 81: 121-39.

Nchinda et al., (2008) the efficacy of DNA vaccination is enhanced in mice by targeting the encoded protein to dendritic cells. J Clin Invest 118: 1427-36.

Nguyen T, et al., (1999) Recognition of breast cancer-associated peptides by tumor-reactive, HLA-class I restricted allogeneic cytotoxic T lymphocytes. Int J Cancer 81: 607-15.

Nie S, et al. Nanotechnology applications in cancer. Annu Rev Biomed Eng. 2007;9:257-288.

Ninalga et al., (2005) CpG oligonucleotide therapy cures subcutaneous and orthotopic tumors and evokes protective immunity in murine bladder cancer. J Immunother 28: 20-7.

Pasqualini et al., (1996) Organ targeting in vivo using phage display peptide libraries. Nature 380: 364-6.

Pisetsky et al., (2001) The role of cpg sequences in the induction of anti-DNA antibodies. Clinical Immunology (Orlando, Fla.) 100: 157-63.

Rasmussen UB, et al., (2002) Tumor cell-targeting by phage-displayed peptides. Cancer Gene Ther 9: 606-12.

Richter J, et al. Construction of highly conductive nanowires on a DNA template. Applied Physics Letters. 2001;78:536.

Rosenberg et al., (1998) Immunologic and therapeutic evaluation of a synthetic peptide vaccine for the treatment of patients with metastatic melanoma. Nat Med 4: 321-7.

Sanchez-Perez et al., (2005) Potent selection of antigen loss variants of B16 melanoma following inflammatory killing of melanocytes in vivo. Cancer Res 65: 2009-17.

Sato et al., (2005) Intraepithelial CD8+ tumor-infiltrating lymphocytes and a high CD8+/regulatory T cell ratio are associated with favorable prognosis in ovarian cancer. Proc Natl Acad Sci U S A 102: 18538-43.

Satoh et al., (2003) Induction of lupus autoantibodies by adjuvants. Journal of Autoimmunity 21: 1-9.

Schuler et al., (2003) The use of dendritic cells in cancer immunotherapy. Curr Opin Immunol 15: 138-47.

Scott et al., Searching for peptide ligands with an epitope library. Science. 1990; 249: 386-390.

Siegel DL, et al., (1997) Isolation of cell surface-specific human monoclonal antibodies using phage display and magnetically-activated cell sorting: applications in immunohematology. J Immunol Methods 206: 73-85.

Singh et al., (1999) Advances in vaccine adjuvants. Nature Biotechnology 17: 1075-81.

Smith et al., Libraries of peptides and proteins displayed on filamentous phage. Methods Enzymol., 1993, 217, 228-257.

Steinman RM (2003) The control of immunity and tolerance by dendritic cell. Pathol Biol (Paris) 51: 59-60.

Steward-Tull Des (1989) Recommendations for the assessment of adjuvants (immunopotentiators). In: G. Gregoriadis ACA, G. Poste (ed). Immunological adjuvants and vaccines. Plenum Press, New York. pp. 213-226.

Telusma G, et al. Dendritic cell activating peptides induce distinct cytokine profiles. Int Immunol. 2006;18:1563-1573.

Trumpfheller et al., (2008) The microbial mimic poly IC induces durable and protective CD4+ T cell immunity together with a dendritic cell targeted vaccine. Proc Natl Acad Sci U S A 105: 2574-9.

Tuerk C, Gold L. Systematic evolution of ligands by exponential enrichment: RNA ligands to bacteriophage T4 DNA polymerase. Science. 1990; 249: 505-510.

Verdegaal et al., (1999) Isolation of broadly reactive, tumor-specific, HLA Class-I restricted CTL from blood lymphocytes of a breast cancer patient. Hum Immunol 60: 1195-206.

Whitehouse et al., (1974) Freund's adjuvants: relationship of arthritogenicity and adjuvanticity in rats to vehicle composition. Immunology 27: 311-30.

Wilson et al., In vitro selection of functional nucleic acids. Annu. Rev. Biochem, 1999,. 68, 611-647.

Xia et al., (2005) Induction of immune tolerance across major histocompatibility complex barrier by transfusion of ultraviolet B-irradiated immature dendritic cells. Transfusion 45: 181-8.

Xiong et al., (2008) Effective CpG immunotherapy of breast carcinoma prevents but fails to eradicate established brain metastasis. Clin Cancer Res 14: 5484-93.

Zanchet D, et al. Electrophoretic Isolation of Discrete Au Nanocrystal/DNA Conjugates. Nano Letters. 2001;1:32-35.

Zhang C, et al., Conformational flexibility facilitates self-assembly of complex DNA nanostructures. Proc Natl Acad Sci U S A, 2008, 105: 10665-9.

Zou W (2005) Immunosuppressive networks in the tumour environment and their therapeutic relevance. Nat Rev Cancer 5: 263-74.

* cited by examiner

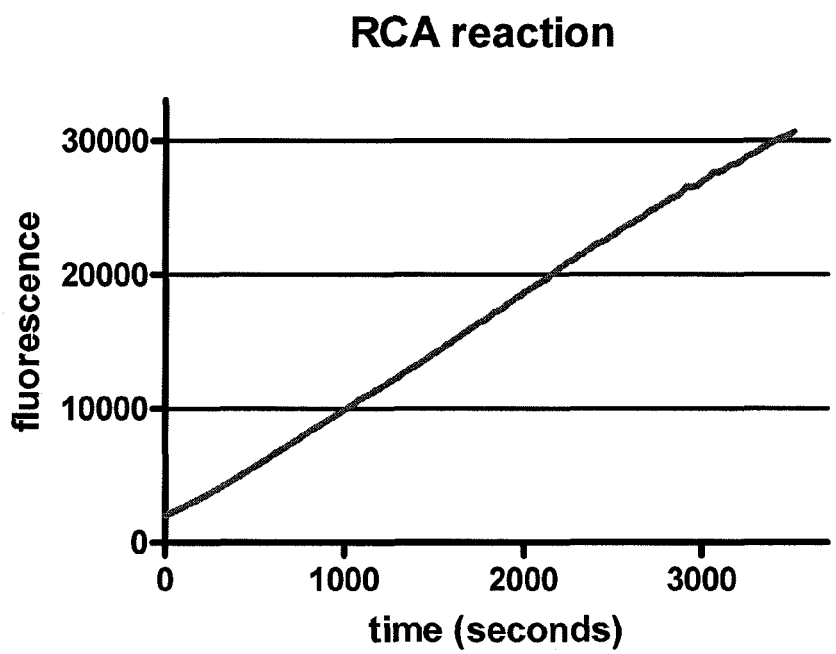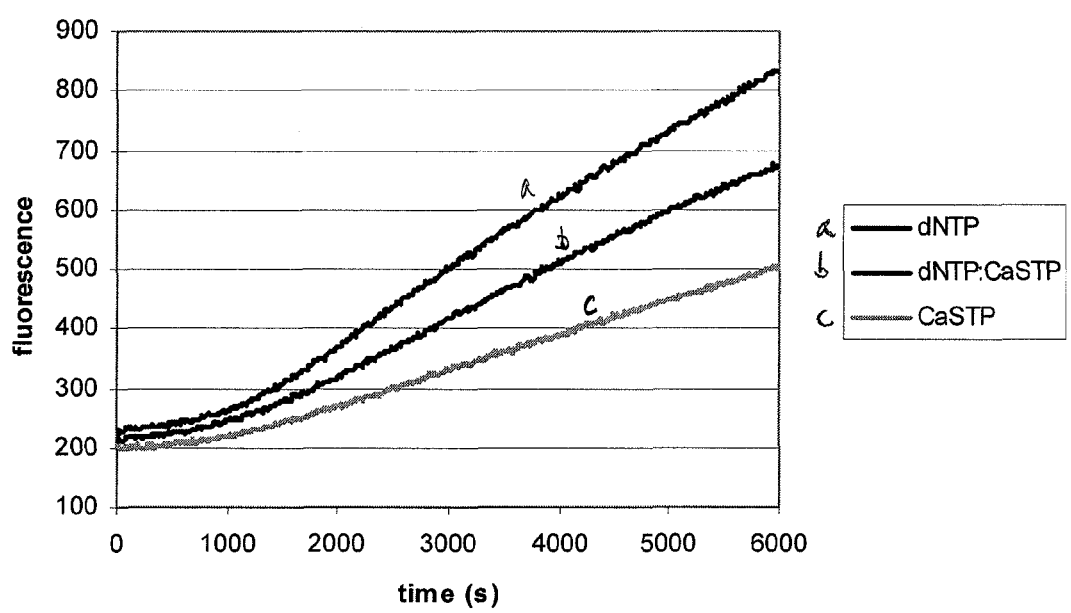
FIG. 15

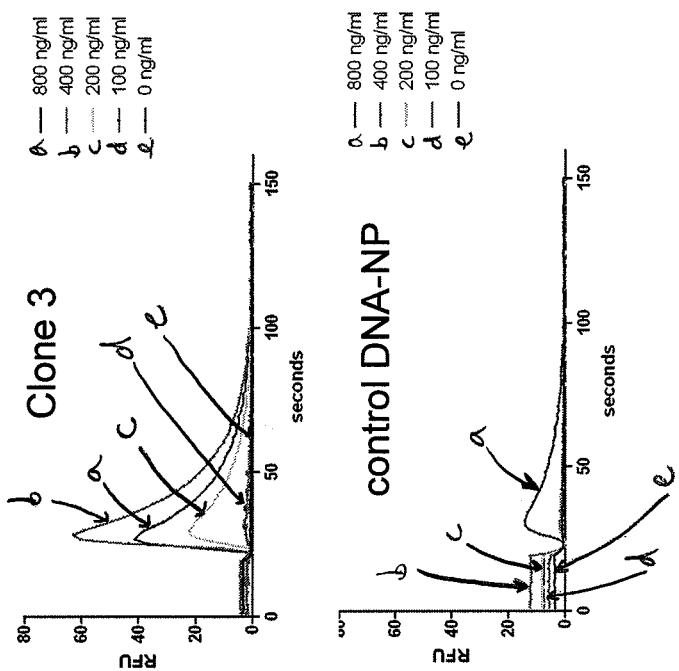
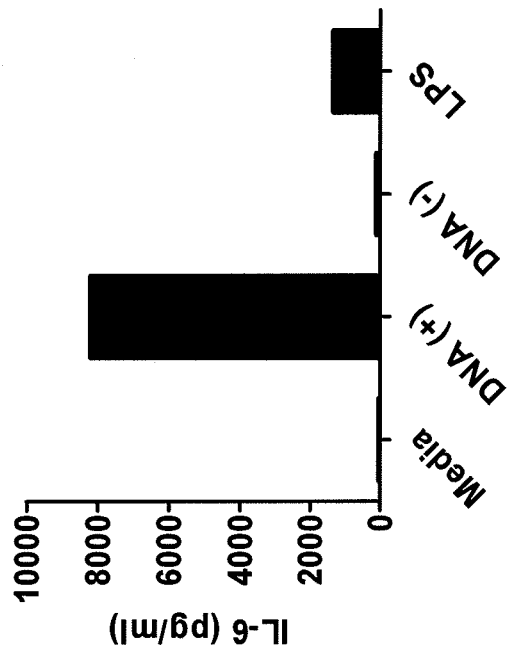
FIG. 20

A. Library generation
B. Screening strategy
C. Amplification & regeneration
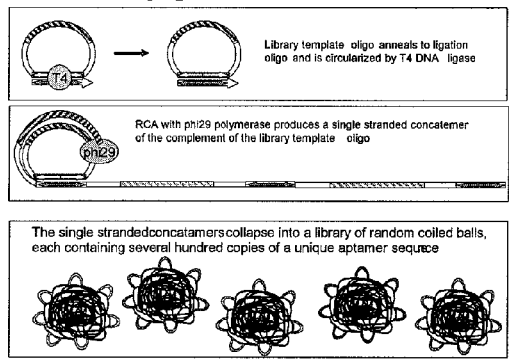
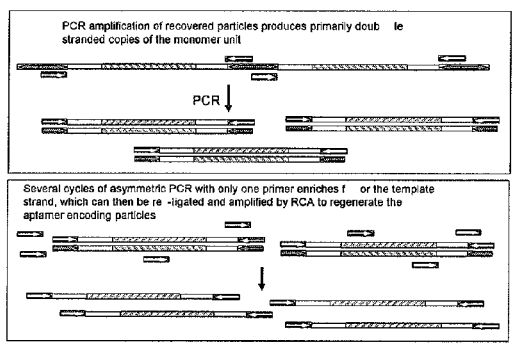
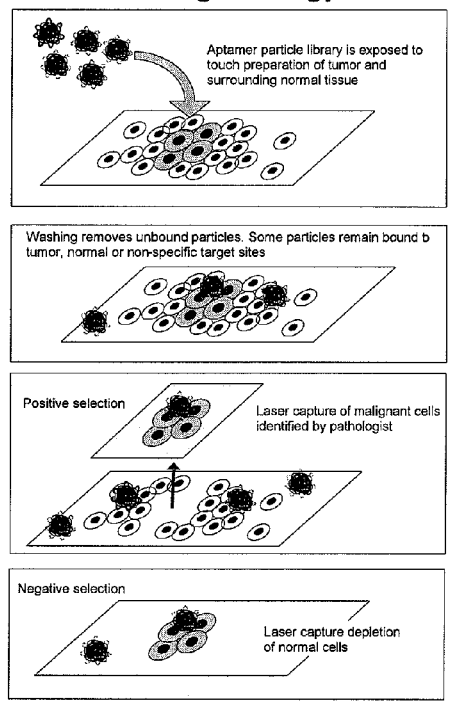
FIG. 29

SINGLE MOLECULE NUCLEIC ACID NANOPARTICLES

RELATED APPLICATIONS

This application is the U.S. National Phase of International Application No. PCT/US2010/053270 entitled SINGLE MOLECULE NUCLEIC ACID NANOPARTICLES, filed Oct. 19, 2010 and published in English on Apr. 28, 2011 as WO 2011/050000, which claims priority to U.S. Provisional Application No. 61/279,408 filed on Oct. 20, 2009, the contents of which is incorporated by reference in its entirety.

STATEMENT REGARDING FEDERALLY SPONSORED R&D

This invention was made with government support under NIH Grant/Contract Numbers U54CA119933501 and U54CA119335 awarded by the National Institutes of Health of the United States of America. The government has certain rights in the invention.

STATEMENT REGARDING FEDERALLY SPONSORED R&D

The present application is being filed along with a Sequence Listing in electronic format. The Sequence Listing is provided as a file entitled UCSD025.TXT, created Oct. 19, 2010, which is approximately 3.2 KB in size. The information in the electronic format of the Sequence Listing is incorporated herein by reference in its entirety

FIELD OF THE INVENTION

The present technology relates to the fields of molecular biology, biochemistry, medicine, and cancer therapeutics. In particular, methods and compositions for making and utilizing nanoparticles comprising nucleic acids are provided.

BACKGROUND

DNA is one of the most thoroughly characterized molecules with regard to structure, chemistry, and modification, and has the capability to serve a wide variety of functions. It can be, and has been, used as a scaffold for the integration of varying entities due to its well defined ability to base-pair hybridize. With the discovery of aptamers and the realization that DNA has the capability to structurally and chemically recognize other molecules with near anti-body specificity at a fraction of the difficultly of synthesis, a new field of DNA based targeting molecules was born. Today there are FDA approved therapeutics based solely on DNA, such as the VEGF aptamer.

Current nanoparticle-based approaches to treating cancer include constructs composed of polymer, silica, or gold nanoparticles, liposomes, and less frequently such platforms as carbon nanotubes and viral capsids. These structures are coated with a variety of functionalizing entities such as polyethylene glycol (PEG) for biocompatibility, various targeting peptides, antibodies, small molecules, or aptamers and some form of therapeutic.

SUMMARY

The present technology relates to a nanoparticle platform based on the unique and varied properties of DNA. Circular DNA can be replicated using a strand displacing polymerase to generate long linear concatamers of controllable length that spontaneously fold into a ball conformation due to internal base-pairing. These balls of DNA are discreet particles that can be made in variable sizes on a nanometer size scale in a scalable manner. The particles can be used in a variety of manners, discussed herein, including specific targeting, drug delivery to cancer cells, and diagnostics. Nanoparticles may also serve as multifunctional platforms for the integration of many currently used cancer therapeutic techniques.

Some embodiments described herein include methods of making a nanoparticle including contacting a circular single-stranded nucleic acid template with a nucleic acid polymerase, wherein the nucleic acid template encodes an aptamer; and amplifying said template with said polymerase to produce said nanoparticle, wherein said nanoparticles comprises a concatemer of the sequence of said template. In such embodiments, the nucleic acid template can be DNA or RNA. In more embodiments, the nucleic acid polymerase is a strand displacing polymerase, such as a DNA polymerase, and can be selected from the group consisting of phi29 polymerase, Klenow fragment, VENT® (Exo) DNA polymerase, 9° $N_m$ DNA polymerase, Bst DNA polymerase, M-MuLV reverse transcriptase, and AMV reverse transcriptase. In some embodiments, the amplifying step has a duration of more than about 1, 5, 10, 25, 30, 50, and 120 minutes. Some methods of making a nanoparticle can also include circularizing a linear nucleic acid template to produce the circular nucleic acid template. The linear nucleic acid template can be more than 10, 50, 100, or 1000 bases in length.

Some embodiments described herein include a nanoparticle made according to the methods described herein. In such embodiments, the nanoparticle can include DNA. The DNA can be more than 1 kb, 10 kb, 100 kb, 1 Mb, 10 Mb, 100 Mb, and 500 Mb in length. The DNA can encode a sequence selected from a siRNA, reporter gene, therapeutic protein, and CpG sequence. Some embodiments include nanoparticles containing a nucleic acid intercalating drug. Such drugs can include Doxorubicin, Daunorubicin, and Dactinomycin. More embodiments include nanoparticles containing an oligonucleotide-linked entity including an aptamer, drug, peptide, and siRNA.

Some embodiments include liposomes containing nanoparticles. More embodiments include pharmaceutical compositions containing nanoparticles. Particular embodiments include methods of treating cancer including administering the pharmaceutical compositions described herein to a subject in need thereof. Even more embodiments include kits containing the pharmaceutical compositions described herein and instructions for use of the kit.

Some embodiments include methods for identifying nanoparticles containing aptamers including generating a library of nanoparticles comprising putative aptamers; and screening the library. The screening can include contacting the library to a capture probe; and selecting for a nanoparticle that binds the capture probe. The capture probe can include a tumor cell.

Some embodiments include nanoparticles containing a single-strand nucleic acid including a concatemeric sequence encoding an aptamer. In some embodiments, the nanoparticle can include DNA. For example, the DNA can be more than 1 kb, 10 kb, 100 kb, 1 Mb, 10 Mb, 100 Mb, and 500 Mb in length. The DNA can encode a sequence selected from a siRNA, reporter gene, therapeutic protein, and CpG sequence. Some embodiments include nanoparticles containing a nucleic acid intercalating a drug. Such drugs can include Doxorubicin, Daunorubicin, and Dactinomycin. More embodiments include nanoparticles containing an oligonucleotide-linked entity including an aptamer, drug, peptide, and siRNA.

Some embodiments include methods to identify tumor cells. Such methods can include contacting a tumor cell with a nanoparticle in which the aptamer selectively binds to the cell; and identifying binding of the aptamer to the cell. More embodiments include the identifying binding of the aptamer to the cell to include identifying a reporter moiety associated with the nanoparticle. The reporter moiety can include a radioactive probe, a reporter protein, a reporter gene, and a fluorescent molecule.

BRIEF DESCRIPTION OF THE DRAWINGS

FIG. 2A shows a photomicrograph of DNA nanoparticles produced by a 30 minute RCA reaction. The particles were labeled after synthesis with Sybr Green dye and imaged at 100× in a fluorescent microscope. FIG. 2B shows a graph of sorted DNA-NP. DNA nanoparticles were made by RCA reactions of varying times, labeled with Oligreen dye, and run on a flow cytometer. The fluorescence intensity correlates with the size of the particles consequent to the reaction time. (Graph a: unlabeled beads; graph b: 7.5 min DNA-NP; graph c: 30 min DNA-NP; graph d: 60 min DNA-NP). FIG. 2C shows a graph relating to DNA nanoparticles produced with Alexa488 labeled nucleotides and run on a flow cytometer. FIG. 2D shows a graph relating to unlabelled DNA nanoparticles hybridized with a complementary oligonucleotide probe labeled with Alexa-647.

FIG. 3A provides DLS data showing increasing size with RCA reaction time. The particles rapidly (10 minutes) obtain a mean size of ~200 nm. After one hour they are ~300 nm FIG. 3B demonstrates monoexponential autocorrelation decays indicating significant monodispersity. All data was collected on a Zetasizer Nano-ZS.

FIG. 15 provides data relating to RCA reaction kinetics. Upper panel: 1 nM ligated oligonucleotides were used as a template for phi29 polymerase to perform RCA and produce single stranded particles. Lower panel: incorporation of phosphorothioate nucleotide. The rate of an RCA reaction was monitored by oligreen fluorescence. Reactions contained dATP, dGTP, dTTP, and either dCTP, a 50:50 mixture of dCTP and 2'-deoxycytidine a-thiotriphosphate, or only 2'-deoxycytidine a-thiotriphosphate. The reaction proceeds 50% slower when only modified nucleotides are used for that one base.

FIG. 16A shows a photomicrograph of DNA nanoparticles produced by a 30 minute RCA reaction. The particles were labeled after synthesis with Sybr Green dye and imaged at 100× in a fluorescent microscope. FIG. 16B relates to DNA nanoparticles that were made by RCA reactions of varying times, labeled with Oligreen dye, and run on a flow cytometer. The fluorescence intensity correlates with the size of the particles consequent to the reaction time. FIG. 16C shows a WETSEM image of DNA-NP produced from a 30 min reaction. The particles are imaged while bound to a poly-lysine coated membrane in aqueous solution.

FIG. 17A provides DLS data showing increasing size with RCA reaction time. The particles rapidly (10 minutes) obtain a mean size of ~200 nm. After one hour they are ~300 nm. FIG. 17B provides data showing monoexponential autocorrelation decays indicating significant monodispersity. All data was collected on a Zetasizer Nano-ZS.

FIG. 19A relates to Clone 3 DNA-NP synthesized with alexa488 nucleotides and incubated with DC and cell lines P815 (mouse mastocytome) and THP1 (human acute monocytic leukemia). Flow cytometry was performed with clone 3, it's reverse complement particle, and DCs incubated with just the nucleotide mix. The same samples were assessed by fluorescent microscopy. The incubations were done on ice. FIG. 19B relates to DC incubated with clone 3 particles at 37° C. No fluorescence was seen in P815 or THP1 incubated with clone 3, nor was any observed in DC incubated with the control reverse complement particle (not shown).

FIGS. 20A-20B provide data relating to clone 3 DC binding DNA-NP elicits cytokine secretion and $Ca^{2+}$ flux. FIG. 20A relates to DCs exposed to DC-binding DNA-NPs (DNA (+)) or control DNA-NPs that do not bind to DCs (DNA(−)), LPS, or media control for 48 h and the amount of Il-6 secreted into the cell culture supernatants was determined by ELISA. DC binding DNA-NP elicited the most IL-6 production. FIG. 20B relates to $Ca^{2+}$ flux followed in real time after exposure of the cells to either clone 3 (top panel) or the control (bottom panel) DNA-NP. The FLIPR Calcium 5 assay was used in conjunction with the FlexStation 3 scanning plate reader, both from Molecular Devices. DC binding nanoparticles that have been purified by dialysis into cell culture grade PBS are added to cell/dye suspensions in a 96 well plate and fluorescent readings are monitored continuously for approximately 150 seconds following administration of nanoparticles. Fluorescent signals indicate increased concentrations of intracellular calcium that is released upon stimulation by DNA nanoparticles.

FIGS. 29A-29C relate to library generation and screening. FIG. 29A shows a schematic diagram of some embodiments that include of a library generation strategy. FIG. 29B shows a schematic of a screening strategy for use on touch preparations of primary tumor samples. FIG. 29C shows a schematic of an amplification and regeneration method for repeated screenings and enrichment of target binders.

FIG. 47A relates to DNA nanoparticles are produced by circularizing a 100 nM concentration of a 94 base ssDNA template with T4 Ligase and a 300 nM concentration of a 31 base templating primer. Polymerization was done with phi29 DNA polymerase at 30° C. for 30 minutes and terminated with EDTA. Discrete particles are stained with SYBR Green and viewed under a 100× oil objective. FIG. 47B Nanoparticles created for various reaction times are measured with Dynamic Light Scattering to validate size and demonstrate positive correlation of hydrodynamic radius with reaction time.

FIG. 48 provides data relating to a comparison of the $9^{th}$ round selection population with the whole and negative control. In this case, it was observed that the population exhibited a net shift over an individual member indicating that, while not complete, the selection had enriched for nanoparticles with enhanced binding capabilities. It is important to note that the incorporation efficiency of Alexa488 OBEA-dCTPs by phi29 polymerase was calculated to be only ~1.5%. While it did not appear to significantly slow the reaction, the poor incorporation is likely the cause of the smaller shifts in the flow peaks.

DETAILED DESCRIPTION

Figure 1A:
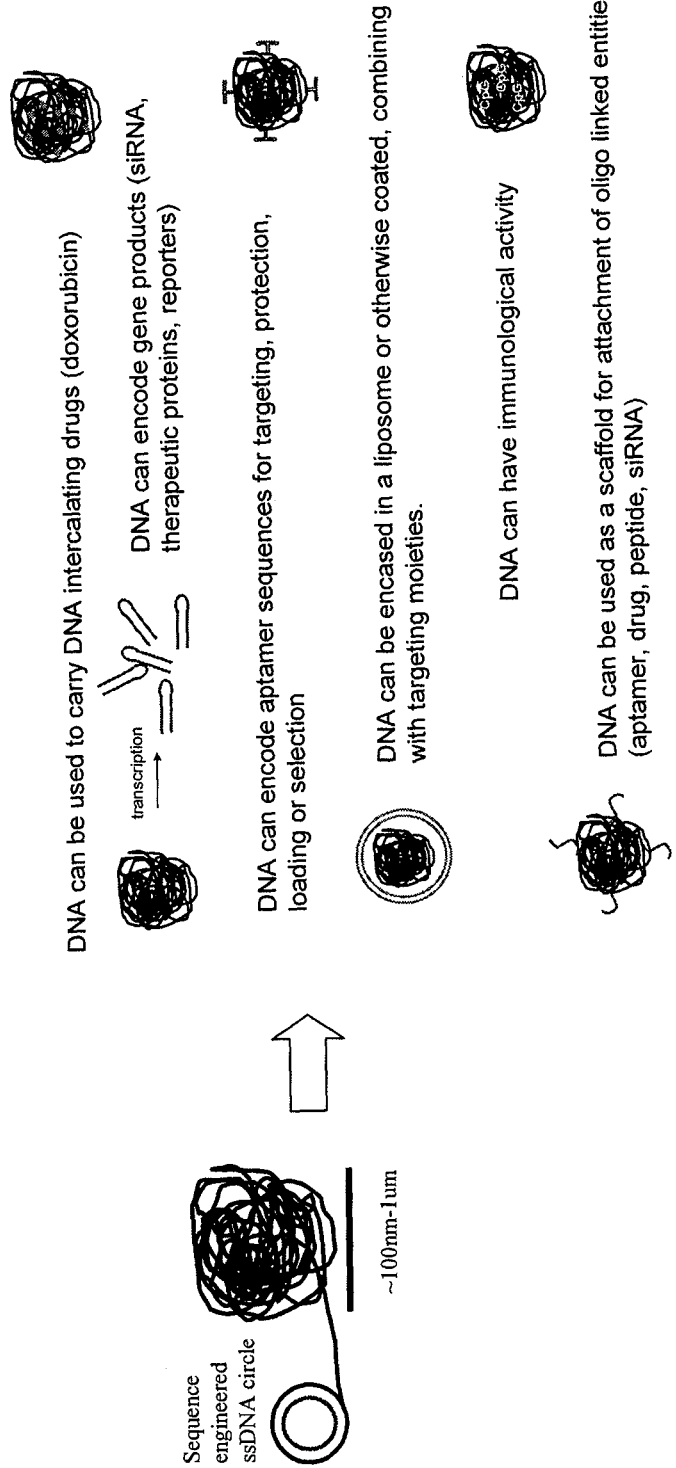
FIG. 1A shows a schematic diagram for uses of DNA nanoparticles.

Some embodiments of the present invention include nucleic acid based nanoparticles comprising multi-kilobase long concatamer copies of a defined aptameric sequence. These can display a sequence several hundred times throughout the particle, as well as on the surface of the nanoparticles. These nanoparticles have the advantage of a significant increase in the strength of binding over current aptamer approaches.

Recent advancements in the understanding of immunity has brought to light the immunological properties of certain sequences of DNA, such as CpG sequences, can greatly stimulate the immune system. CpG sequences can be used as an adjuvant for the delivery of DNA based vaccines. A DNA based nanoparticle can easily incorporate these sequences to be displayed hundreds of times on a single particle potentially increasing the potency several orders of magnitude.

More embodiments include nanoparticles comprising small molecules, for example, drugs such as chemotherapeutics. Many of the most common cancer chemotherapeutics are natural DNA binding molecules. Delivery of chemotherapeutics bound to DNA is a method to sequester such chemotherapeutics for transport to a delivery site. DNA is also easily modified through altered base composition to control such parameters as degradation, salt, and pH responsiveness.

More embodiments include nanoparticles comprising nucleic acid encoding sequence information. For example, DNA is an information carrier that could be utilized for applications such as gene therapy and siRNA delivery. More embodiments can include DNA encoding therapeutic proteins and reporter genes.

One major advantage of this approach includes the ability to avoid complex conjugation chemistries for targeting specificity, biocompatibility, and drug incorporation of nanoparticles. Also, clinical testing may be simpler for nucleic acid based nanoparticles. For example, whereas the addition of any addition to other types of nanoparticles may create a new entity for clinical testing, here, a single particle of DNA can incorporate many therapeutic functions and remains one type of molecule, namely, DNA, a molecule that has been already approved for in vivo human use.

DNA nanoparticles can be made cheaply in a volumetric scalable way with simple techniques. Once validated for function and developed they would most likely meet regulatory guidelines quickly and be translated into clinical use. In addition to clinical use, DNA nanoparticles can be used in diagnostics, for example, as sensing agents utilizing DNA's ability to react to its microenvironment.

The basic creation of DNA nanoparticles begins with a padlock probe of single stranded DNA. The sequence of this probe can be engineered for a variety of purposes, non-limiting examples can include, immunogenic stimulation, enzymatic degradation, and specific hybridization. This probe can vary in length from at least about 2 bases, at least about 5 bases, at least about 10 bases, at least about 50 bases, at least about 100 bases, at least about 500 bases, at least about 750 bases, at least about 1000 bases, at least about 1 kb, at least about 5 kb, at least about 10 kb, at least about 50 kb, and longer.

First, the probe is ligated endwise to form a closed loop circle via a templating primer complementary to the ends of the probe. The templating primer then serves as a primer for polymerization with a strand displacing polymerase with the circle acting as an endless template in Rolling Circle Amplification (RCA) (FIG. 1A).

The polymerization can proceed for a period of time, after which a certain length of single stranded DNA is created comprising concatamer repeats of the original padlock probe. The concatamer can spontaneously form a globular shape based on internal base pairing. The size of the nanoparticles can be controlled by, for example, the polymerization time of the reaction, the type of polymerase used, and reaction conditions such as salt concentration and pH. In some embodiments, the polymerization can proceed for a length of time according to the length of product desired, where a longer time can produce a longer product.

Non-limiting examples for functions of the nanoparticles are shown in FIG. 1A. The DNA nanoparticle has multiple copies of the original sequence both internally base-paired as well as displayed on the surface which can serve as hybridization sites for DNA conjugated entities or as a multivalent display of an aptameric sequence that can be used for targeting. They might also be coded to contain immunostimulatory sequences such as certain CpG sequences. Furthermore, it may be possible to encode genetic information in the RCA product and/or encase the DNA nanoparticles in other nanostructures such as liposomes.

Some embodiments include nanoparticles with aptamers for use in therapy. These particles have several advantages. For example, DNA is essentially non-toxic, biocompatible, and can used as a scaffold for the attachment of other agents. Also, DNA particles can be easily loaded with DNA binding chemotherapy agents, such as Doxorubicin and, if targeted by an aptamer sequence, may represent an ideal targeting mechanism for such drugs.

Chemically diverse libraries are a rich source of potential ligands for biomolecules and cellular targets of interest. When modular biopolymers such as nucleic acids or polypeptides are used, the combinatorial diversity of these libraries can become astronomical and well beyond the capabilities of systemic high throughput screening methods. Combing these libraries then requires iterative schemes that couple a selection step with an amplification step. For peptides, display of a given peptide on a bacteriophage, virus, or bacteria allows amplification by growth of the host organism (Scott J K, Smith G P. Searching for peptide ligands with an epitope library. Science. 1990; 249: 386-390). Nucleic acids are typically amplified by some variation of PCR (Tuerk C, Gold L. Systematic evolution of ligands by exponential enrichment: RNA ligands to bacteriophage T4 DNA polymerase. Science. 1990; 249: 505-510). These tools have been used to select peptides and short nucleic acid sequences (aptamers) that can bind to a wide variety of proteins and cellular targets.

However, peptide and aptamer libraries have some distinct limitations. Many peptide display formats, such as phage, present many copies of each peptide per particle. This can allow the recovery of relatively low affinity interactions that benefit from the high avidity of the presentation format. However, it may be difficult to maintain the desired binding avidity and specificity when the selected peptides are moved to another particle or molecule. Aptamer libraries can suffer from the reverse complication since they are usually presented in a monovalent format. Aptamers have been most clinically useful when a high affinity interaction can function in an antagonist manner, though they have been used as targeting moieties attached to nanoparticle drug delivery vehicles (Farokhzad O C, et al. Targeted nanoparticle-aptamer bioconjugates for cancer chemotherapy in vivo. Proc Natl Acad Sci USA. 2006; 103:6315-6320; Bagalkot V, et al. An aptamer-doxorubicin physical conjugate as a novel targeted drug-delivery platform. Angew Chem Int Ed Engl. 2006; 45:8149-8152). However, when aptamers that were selected in a monovalent format are attached to particles in a multivalent way, specificity can be lost as low affinity interactions gain avidity. In addition, there is always a concern that the transfer or attachment of a peptide or aptamer to a new molecule or particle may alter its conformation and binding affinity for the target of interest. Thus for targeting moieties on particles, it would be ideal to select the optimal ligand in the very context in which it will be used.

A methodology has been developed for the construction of large libraries of DNA nanoparticles and a process for the iterative selection of particles with the desired properties. When coupled with the other structural, functional, chemical, and informatic properties of DNA these selectable particles allow the creation of multifunctional particles for biomedical and therapeutic use.

Molecular Evolution

Specific molecular recognition is the basis for most of life's biological processes, but in the clinic and laboratory the tools for such are limited to monoclonal antibodies, peptides, aptamers, small molecules or natural biomolecule ligands. These tools have not matched well with the problem of specific recognition of neoplastic cells from their normal counterparts for several reasons. The primary reason is that unique molecular structures common to neoplastic cells of a given type but distinct from normal cells are rare and all of the methods above, in their simple forms, target only a single molecular shape. Bi-specific or multi-specific versions have been described, for example diabodies and bi-specific antibodies, but these are difficult to produce and not widely used (Kortt A A, et al. Dimeric and trimeric antibodies: high avidity scFvs for cancer targeting. Biomol Eng. 2001;18:95-108). High affinity binding moieties can also suffer a loss of specificity when combined because already high affinity interactions do no benefit much from coupled or multi-valent interactions, but previously low affinity interactions can gain avidity and compromise selectivity.

Chemically diverse libraries are a rich source of potential ligands for biomolecules and cellular targets of interest. When modular biopolymers such as nucleic acids or polypeptides are used, the combinatorial diversity of these libraries can become astronomical and well beyond the capabilities of systematic high throughput screening methods. Combing these libraries requires iterative schemes that couple a selection step with an amplification step. For peptides, display of a given peptide on a bacteriophage, virus, or bacteria allows amplification by growth of the host organism (Scott J K, Smith G P. Searching for peptide ligands with an epitope library. Science. 1990; 249:386-390). Nucleic acids are typically amplified by some variation of PCR. Subtractive and in vivo selection schemes have been developed for aptamer and phage displayed peptide libraries that can enhance the cell specificity of recovered targeting ligands. Cellular targeting has been demonstrated by libraries of peptides and oligonucleotide aptamers (Siegel D L, et al. Isolation of cell surface-specific human monoclonal antibodies using phage display and magnetically-activated cell sorting: applications in immunohematology. J Immunol Methods. 1997; 206:73-85; Rasmussen U B, et al. Tumor cell-targeting by phage-displayed peptides. Cancer Gene Ther. 2002; 9:606-612; Hicke B J, et al. Tenascin-C aptamers are generated using tumor cells and purified protein. J Biol Chem. 2001; 276:48644-48654).

However, peptide and aptamer libraries have some distinct limitations. Most peptide display formats, such as phage, present many copies of each peptide per particle. This can allow the recovery of relatively low affinity interactions that benefit from the high avidity of the presentation format. However, it may be difficult to maintain the desired binding avidity and specificity when the selected peptides are moved to another particle or molecule. Aptamer libraries can suffer from the reverse complication since they are usually presented in a monovalent format. Aptamers have been most clinically useful when a high affinity interaction can function in an antagonist manner, though they have been used as targeting moieties attached to nanoparticle drug delivery vehicles (Farokhzad O C, et al. Targeted nanoparticle-aptamer bioconjugates for cancer chemotherapy in vivo. Proc Natl Acad Sci USA. 2006; 103:6315-6320; Bagalkot V, et al. An aptamer-doxorubicin physical conjugate as a novel targeted drug-delivery platform. Angew Chem Int Ed Engl. 2006; 45:8149-8152). However, when aptamers that were selected in a monovalent format are attached to particles in a multivalent way, specificity can be lost as low affinity interactions gain avidity. In addition, there is always a concern that the transfer or attachment of a peptide or aptamer to a new molecule or particle may alter its conformation and binding affinity for the target of interest. Thus for targeting complex targets like cells where specificity is a greater concern than raw affinity, it would be ideal to select the optimal ligand in the very context in which it will be used.

Furthermore, while aptamer and phage display technologies are occasionally referred to as evolutionary processes (one of the earliest aptamer papers described the process as SELEX—Systematic Evolution of Ligands by Exponential Enrichment), they are usually a sequential combing process (thus the term "biopanning") and lack a key component of Darwinian evolution—the generation of variants. Even if point mutation is introduced in each round through error prone PCR or growth in mutator bacteria, the evolutionary potential is limited (Tuerk C, Gold L. Systematic evolution of ligands by exponential enrichment: RNA ligands to bacteriophage T4 DNA polymerase. Science. 1990; 249:505-510; Scott J K, Smith G P. Searching for peptide ligands with an epitope library. Science. 1990; 249:386-390; Gram H, et al. In vitro selection and affinity maturation of antibodies from a naive combinatorial immunoglobulin library. Proc Natl Acad Sci USA. 1992; 89:3576-3580; Irving R A, et al. Affinity maturation of recombinant antibodies using E. coli mutator cells. Immunotechnology. 1996; 2:127-143). Rapid evolution in natural systems occurs when large units of information can re-assort and recombine, as is the case during meiosis.

Cell affinity agents are needed in many areas of cancer research and clinical study. Monoclonal antibodies are the workhorse of cell labeling, but are mostly useful when a given cell surface molecule is know. For cancer cell detection in blood or tissue or for cancer cell capture, single monoclonal antibodies are rarely sufficient to distinguish cancer cells from neighboring tissue or other normal cells. Clinically, this can be a problem for evaluating surgical resection margins and for pathological analysis of small samples (Blair S L, et al. Enhanced touch preps improve the ease of interpretation of intraoperative breast cancer margins. Am Surg. 2007; 73:973-976; Cortes-Mateos M J, et al. Automated microscopy to evaluate surgical specimens via touch prep in breast cancer. Ann Surg Oncol. 2009; 16:709-720). There as been considerable interest of late in circulating tumors cells, but these are present in very low numbers and require highly processive and efficient capture methods to be obtainable in sufficient numbers for down stream analyses. In vivo imaging with cancer targeted contrast agents would be of obvious utility, and there is considerable interested and development of tumor targeted nanoparticles for drug delivery (Nie S, et al. Nanotechnology applications in cancer. Annu Rev Biomed Eng. 2007; 9:257-288). In vivo applications require biocompatible materials, and DNA is obviously one such polymer.

Figure 1B:
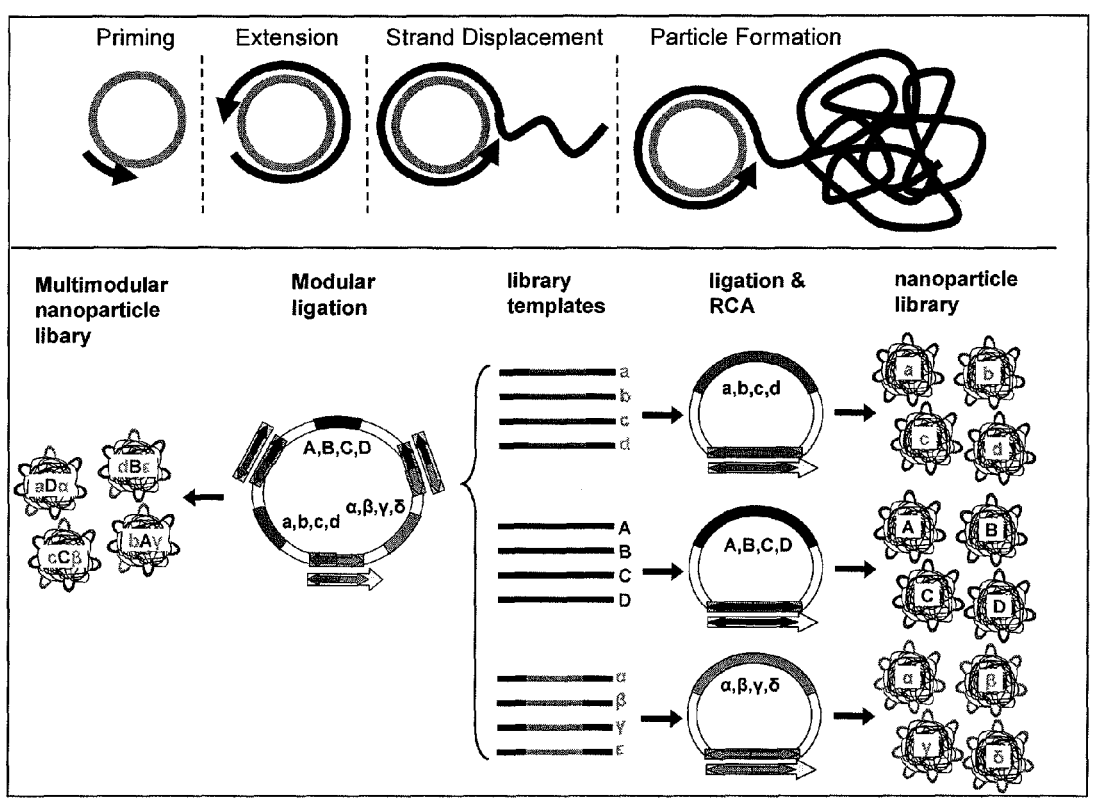
FIG. 1B shows a schematic overview of DNA nanoparticle synthesis and modular DNA particle library creation. Single module libraries can be biopanned, whereas the modules within the multimodule libraries can be re-assorted from round to round, creating particles with novel combinations of modules.
Figure 2:
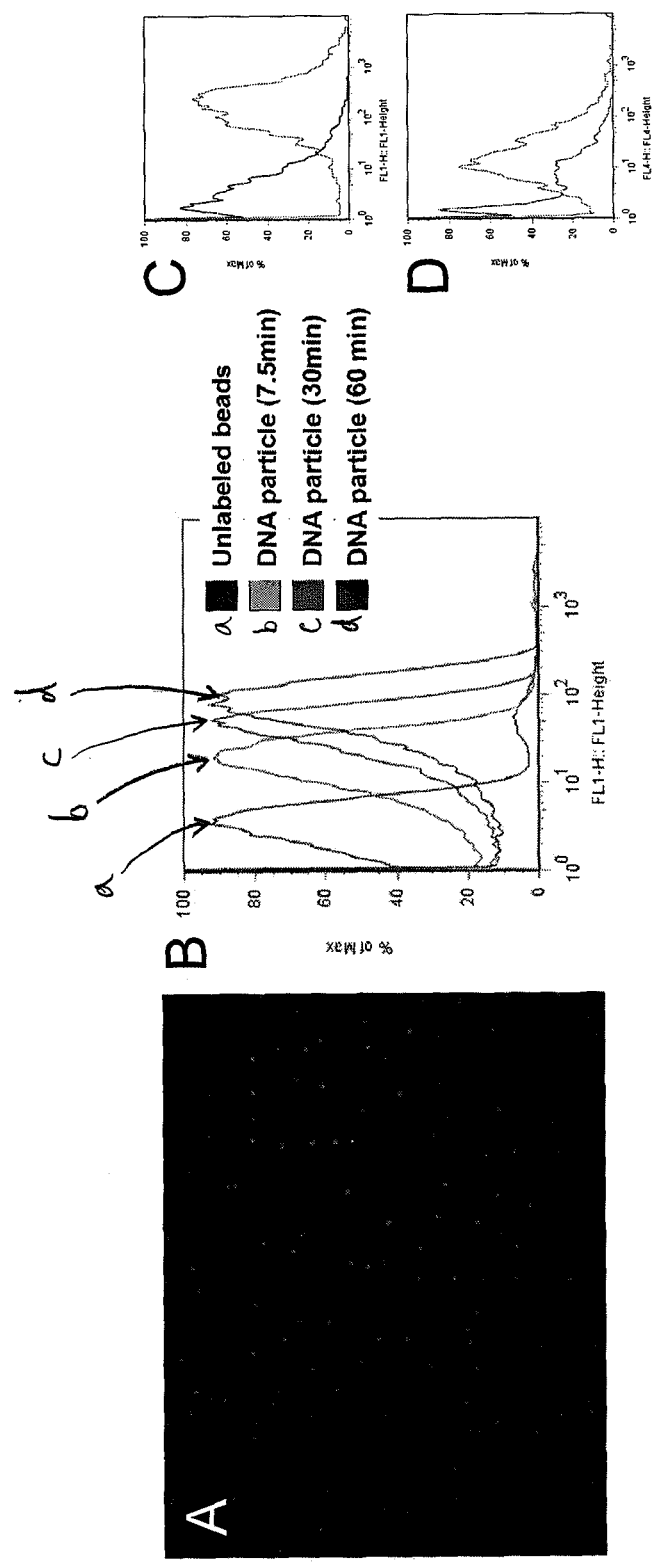
FIGS. 2A-2D relate to a visualization of DNA nanoparticles.

Accordingly, a DNA nanoparticle library technology has been developed that uses rolling circle amplification (RCA) of circular oligonucleotide templates to produce libraries of single stranded DNA nanoparticles that can be selected for cell binding properties. By including random nucleotide sequences in the template oligonucleotide, libraries can be produced and desired functions selected. In some embodiments multimodal DNA nanoparticles can be created that specifically bind to cancer cells. In more embodiments, methods to optimize the creation of multimodal DNA nanoparticles are described. The desired particles are "bred" by a novel iterative selection and re-assortment method to create modular DNA nanoparticles that contain multiple distinct recognition elements (FIG. 1B).

A challenge in many areas of cancer research and treatment is the production of cancer cell specific binding agents. In a few cases truly cancer cell specific antigens can be targeted by antibodies or other affinity ligands, but more often cancer cells distinguish themselves by altered levels of multiple surface molecules. The multimodal particles proposed here are capable of multiple interactions with the target cell of interest and can potentially overcome the limitation of single target agents such as antibodies, peptides, and aptamers.

Some embodiments include methods to validate and optimize combinatorial selection for multi-module particles. Data demonstrates the selection of cell binding particles from a library where each DNA nanoparticle contains a single recognition sequence module. Using a leukemia (K-562) and a non small cell lung cancer line (NCI-H23) as model systems, the optimal combinatorial strategy are identified.

Some embodiments include methods to create particles that bind to lung cancer and leukemia cell lines. Several different cells lines derived from each of the two tumor types are used to select particles with broad specificity to that tumor type. Cell lines from non-neoplastic origins are used in subtractive screening strategies if non-specific binders are recovered.

Some embodiments include methods to demonstrate cancer specific cell binding of selected particles. Fluorescently labeled particles are used on tissue arrays for fluorescent microscopy and on suspension cells for flow cytometry. Particles tagged with biotin or iron oxide are used for magnetic cell separation.

While this technology is similar to aptamer technology in that it uses nucleic acid libraries as the basis for molecular recognition, it differs in several important ways. Each particle contains many copies of the sequence elements so there is intrinsic multivalent display of the modules, allowing avidity to compensate for low monovalent affinity. The modular nature of the particle template construction allows multiple distinct recognition elements to be assembled into a single molecular entity. Furthermore, the combinatorial selection method allows the optimal particle with multiple recognition elements to be evolved in the same molecular context in which it will be used, rather than grafting them on to some other framework or particle for application. The combinatorial method also adds an element of true molecular evolution in which novel combinations of modules can be created by re-assortment, akin to recombination in meiosis.

It should be noted that there are many potential clinical applications of these nanoparticles since DNA can have several functions in addition to the formation of specific ligands. DNA can be immunogenic if it contains unmethylated CpG motifs, it can act as a scaffold for hybridizing other oligonucleotide conjugates, it can have enzymatic activity, it is easily chemically modified to allow small molecule or metal ion attachment and metals can be directly deposited onto DNA, it can carry DNA binding drugs, and it can carry genetic information (Klinman D M. Adjuvant activity of CpG oligodeoxynucleotides. Int Rev Immunol. 2006; 25:135-154; Breaker R R, Joyce G F. A DNA enzyme that cleaves RNA. Chem Biol. 1994; 1:223-229; Berti L, et al. DNA-Templated Photoinduced Silver Deposition J. Am. Chem. Soc. 2005; 127:11216-11217; Richter J, et al. Construction of highly conductive nanowires on a DNA template. Applied Physics Letters. 2001; 78:536; Lund J, et al. DNA Networks as Templates for Bottom-Up Assembly of Metal Nanowires. 5th IEEE Conference on Nanotechnology. Nagoya, Japan; 2005: 836-840; Zanchet D, et al. Electrophoretic Isolation of Discrete Au Nanocrystal/DNA Conjugates. Nano Letters. 2001; 1:32-35). Thus the particles selected using methods provided herein can serve as the basis for multifunctional nanoparticles for imaging, drug delivery, or immunotherapy. DNA has a long clinical history and a favorable toxicity and biodegradability profile (Fichou Y, Ferec C. The potential of oligonucleotides for therapeutic applications. Trends Biotechnol. 2006; 24:563-570).

Methods and compositions provided here are potentially transformative in the area of cancer cell study and detection because they couple the power of random libraries and biopanning selections with molecular breeding concepts to create multifunctional molecules for cell binding. In addition to the conceptual advantages of this approach, discussed herein, once a particle has been selected and sequenced, other laboratories can easily create that particle from bacteria containing the cloned sequence or a synthetic oligonucleotide and a few simple molecular biology steps. The RCA reaction is scale-able and far less complicated than hybridoma technology. The pioneering approach of creating a single molecule nanoparticle with modular functionality is groundbreaking in its flexibility and potential for development as a platform for applications beyond just those discussed in detail here. Some embodiments provided herein are unique and innovative in at least three major ways. First, the module designs are unlike any other library format in flexibility and ease of implementation. Second, selection formats are the same as the application format meaning the selected particles can be used immediately without the need to chemically alter or conjugate them to another molecule or particle. Finally, compared to other nanoparticle materials, DNA is non-toxic and antisense oligonucleotides, aptamers, gene therapy, and CpG oligonucleotides have all been used in human trials.

Production and Characterization of DNA Nanoparticles by RCA

DNA nanoparticles are produced by enzymatic DNA synthesis using a strand displacing DNA polymerase, phi29, and a circular oligonucleotide template. The oligonucleotide circle is typically produced by ligation of a 100-200 base pair linear oligonucleotide with a short (30 bp) oligonucleotide complementary to the ends. The ligation oligonucleotide also serves as the initiating primer for the RCA reaction. Phi29 polymerase is highly processive (~70 kb) and produces a linear increase in single stranded DNA for over an hour in a typical reaction.

The resulting RCA products are concatemers complementary to the template circular oligonucleotide. These long single stranded products collapse into randomly coiled nanoparticles, a property that has been exploited for counting individual RCA events (Jarvius J, et al. Digital quantification using amplified single-molecule detection. Nat Methods. 2006; 3:725-727). The size of the particles is a function of the time and efficiency of the RCA reaction. The reaction can be stopped by the addition of EDTA or heat inactivation of the phi29 polymerase, though the latter may lead to aggregation of the DNA particles. The particles can be visualized with either single stranded or double stranded fluorescent DNA binding dyes due to the double stranded character that results from internal base pairing. For analytical purposes the particles can be made fluorescent by the inclusion of fluorescently labeled nucleotides during the synthesis. Alternately a fluorescently labeled oligonucleotide probe can by hybridized to the particles (FIG. 2A-D).

Figure 3:
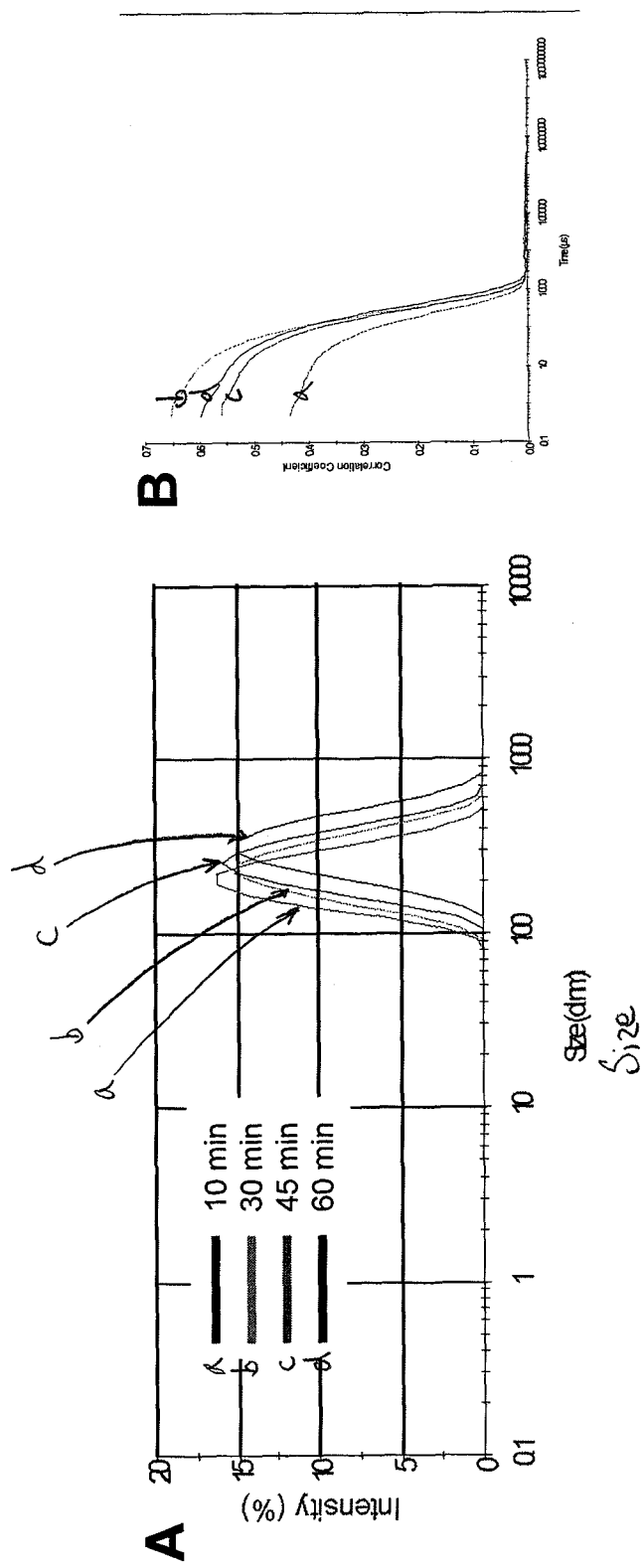
FIG. 3A and FIG. 3B relate to DNA nanoparticles sized by Dynamic Light Scattering (DLS).

It is difficult to size the particles by conventional or denaturing gel electrophoresis due to their large size and single stranded character. Dynamic Light Scattering (DLS) is a common technique for measuring the properties of nanoparticles such as size and zeta potential. DLS uses the time autocorrelation of a signal of scattered light to determine the polydispersity and average diffusion coefficient, which through the Stokes-Einstein equation is related to the average dynamic radius. RCA reactions were carried out for four time points (10, 30, 45, 60 minutes) and were stopped by the heat inactivation of the polymerase at 65° C. for 10 minutes. The samples are then immediately measured by DLS. For a monodisperse sample the autocorrelation plots should show a single exponential decay, the exponent coefficient of which is known as the first moment and is used to calculate a Z-average size. The second moment is used to calculate the deviation from monodisperse and is known as the polydispersity index (PdI), which is a measure of relative peak width of the Gaussian size distribution. In general if the PdI is greater than 0.25 it is recommended to use a secondary algorithm called Non-Negative Least Squares (NNLS) which models the autocorrelation curve as a contribution of several size samples and extracts individual peak data (FIG. 3A-3B).

Single Component DNA Nanoparticle Library Construction and Testing

Figure 4:
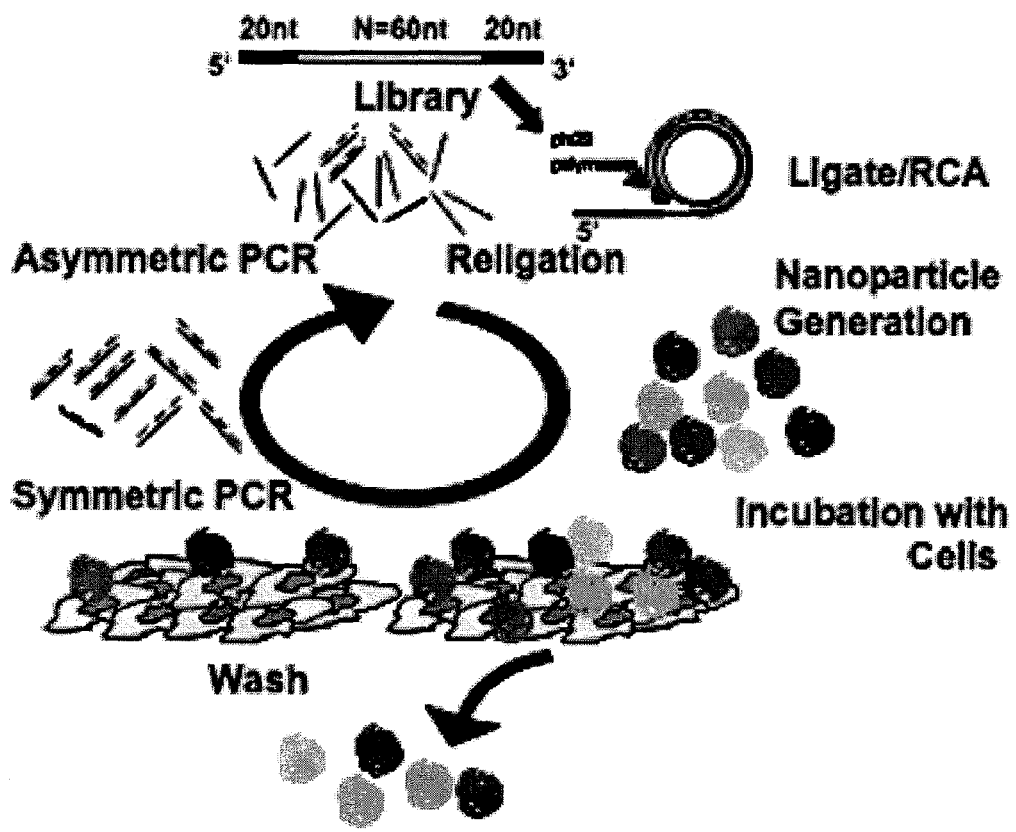
FIG. 4 shows a schematic of the flow of selection scheme for DNA nanoparticles that bind human dendritic cells. A 100 base library with a 60 base random region flanked by 2 20 base primer sites is ligated and amplified with Rolling Circle Amplification to produce nanoparticles. The nanoparticles are incubated with the target cells and washed. Remaining nanoparticles are amplified by PCR and then asymmetrically PCR (using only one primer) to generate an excess of the desired strand. The desired strand is re-ligated and the cycle is repeated.

A method to generate high diversity libraries of DNA nanoparticles and select for those with desired features through an iterative screening and re-amplification method is summarized in FIG. 4.

The library is generated from a template oligonucleotide that has a random stretch of bases in the middle, flanked by PCR primer sites. These ends also bind to the ligation oligonucleotide to circularize the template for RCA amplification. The random sequence is 60 nucleotides long and is flanked by defined sequences that can be used to hybridize fluorescent or otherwise labeled probes for visualization or purification. Using this design ~10 billion unique DNA nanoparticles can be produced in a small volume (e.g., 50 μl) RCA reaction. The particles are screened for the desired binding activity and the binders amplified by PCR using the Stoffel fragment of Taq polymerase that lacks 5' to 3' exonuclease activity. The use of Stoffel fragment greatly increased the amplification efficiency, presumably due to the concatemeric nature of the DNA nanoparticles. Following amplification several rounds of asymmetric PCR are performed to increase the copy number of the template strand that is then circularized by ligation and subjected to RCA to regenerate the DNA particles. The cycle of screening, amplification, and particle regeneration is repeated for several (e.g., 5-10) rounds.

Figure 5:
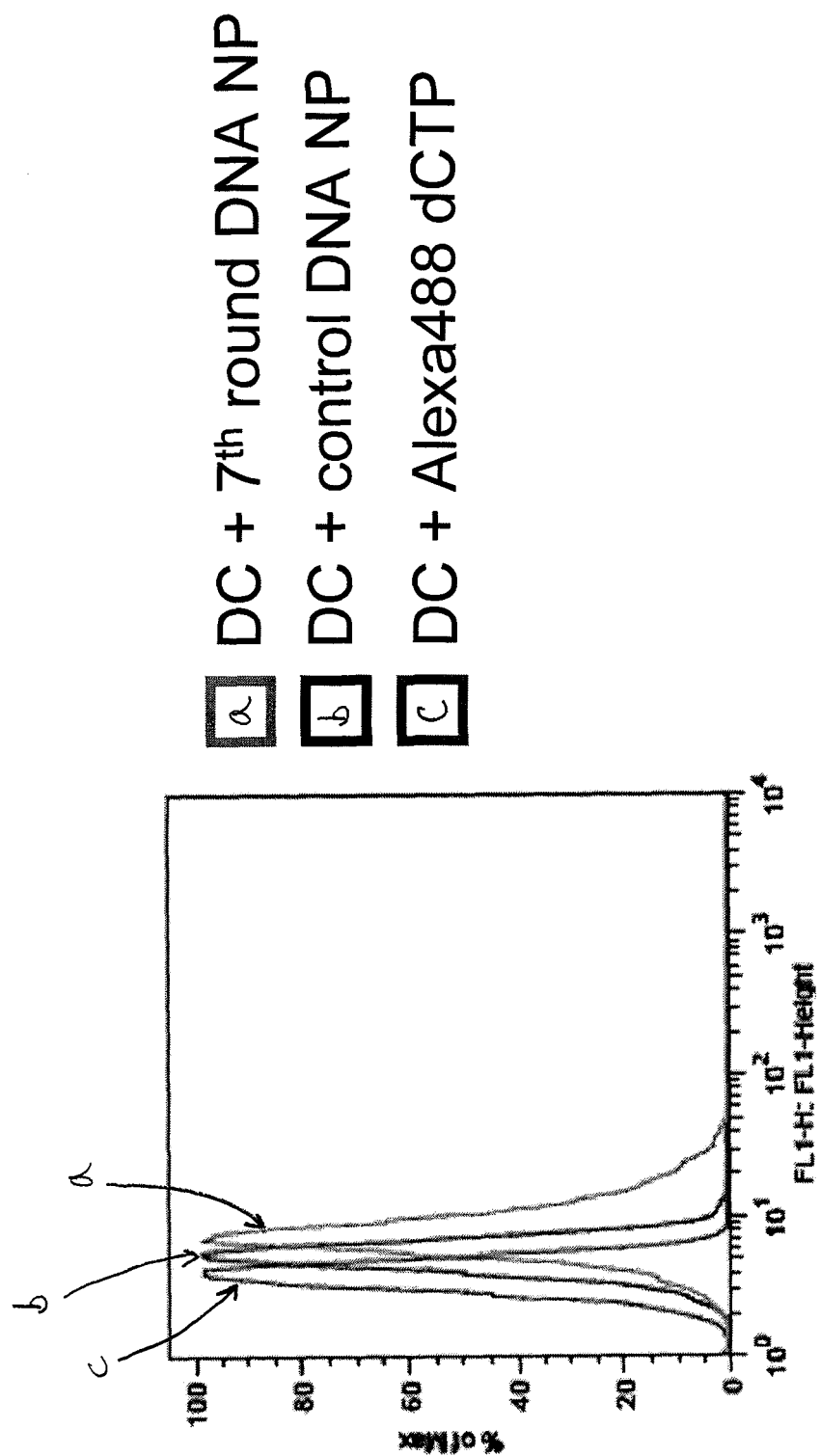
FIG. 5 shows a graph of fluorescence and indicates the selection of DNA nanoparticles that bind to human dendritic cells (DCs). The pool of DNA nanoparticles after 7 rounds of selection was regenerated with fluorescent nucleotides and compared to a similarly labeled non-specific control DNA nanoparticle. The red curve shows DCs with free labeled nucleotides. There is a clear shift in the labeling intensity with the selected particles.

The scheme described herein has been used to select DNA nanoparticles that bind to human dendritic cells (DCs). DCs were generated from peripheral blood monocytes. After 5-7 days of culture, DC were incubated for 1 hour with the DNA nanoparticle library, and washed several times with cold PBS. After 7 cycles of selection and re-amplification aggregation of the DCs during the washing steps was observed, suggesting that binding particles had been enriched for that were causing agglutination. Flow cytometry analysis indicated that the population of particles contained in the 7$^{th}$ round pool was enriched for particles that bound to DCs (FIG. 5).

Figure 6:
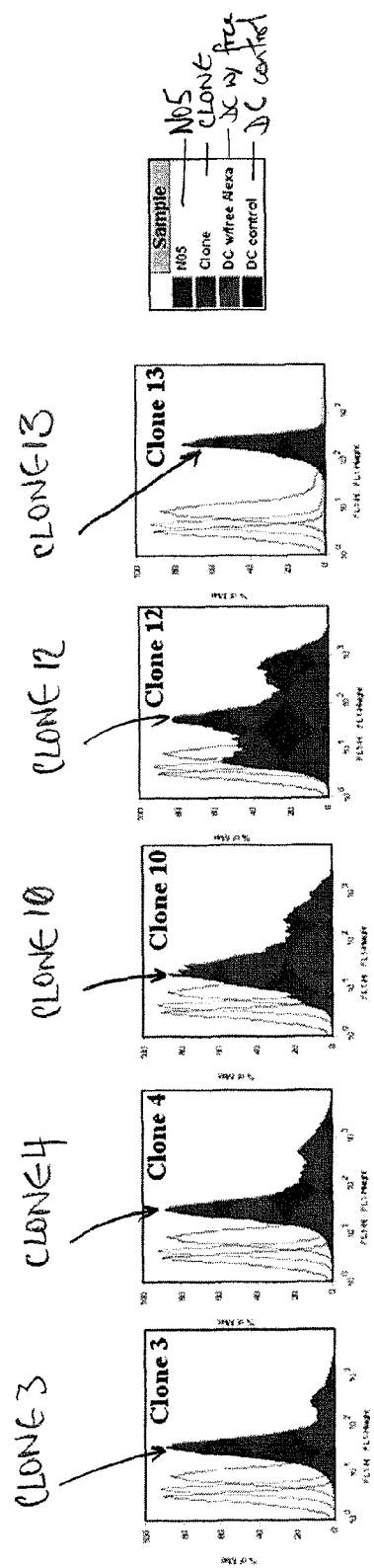
FIG. 6 provides flow cytometry data for 5 positive clones sequenced from round 7 of selection protocol. Controls included a DNA nanoparticle that did not bind (N05), dendritic cells alone and dendritic cells with free Alexa488-dCTP used to label the DNA.

Individual particles were obtained by cloning the PCR amplification products from the 7$^{th}$ round of selection. 15 clones were sequences and all but one were unique. Each clone was used to generate fluorescently tagged DNA nanoparticles and these were tested for DC binding by flow cytometry. Several of the clones showed good binding to the DCs (FIG. 6).

Further characterization of these DC binding particles is underway, but the data to date demonstrates the feasibility of the DNA nanoparticle library selection strategy. In addition, non-specific uptake or immune activation of non-targeted particles has not been observed, suggesting that selection of particles with binding affinity for the target cell type is essential and that non-specific cell binding is minimal.

The DNA nanoparticles are stable over the time of the experiments. However, the particles are fairly resistant to exonuclease and endonuclease degradation. Since the particles are formed from a continuous single stranded DNA molecule, each particle has only one 3' and one 5' end which may account for their resistance to exonuclease digestion. Most endonucleases, including DNase, prefer double stranded DNA as a substrate. The nuclease resistance could increase by polymerizing nucleotides with altered backbone chemistries. The phi29 polymerase can incorporate phosphorothioate backbone nucleotides, although the rate of polymerization is marginally slower.

Research Design and Methods

Some embodiments provided herein include methods and compositions to develop multimodal particles that bind to a target cell type through combinatorial "breeding" of DNA nanoparticles. The overall strategy is to first optimize the selection methodology, then apply the method to a panel of cell lines from each of two cancer types and confirm their usefulness in several cell binding applications. The rationale for using multiple cell lines from a couple of cancer types is to allow the selection of particles that are tumor specific but not cell line specific and to then be able to cross compare. If necessary, subtractive screening methodologies are employed to prevent the recovery of non-specific cell binding particles. Cell lines or normal lines (e.g. NIH-3T3) are used for subtraction.

Methods to Validate and Optimize Combinatorial Selection

Figure 7:
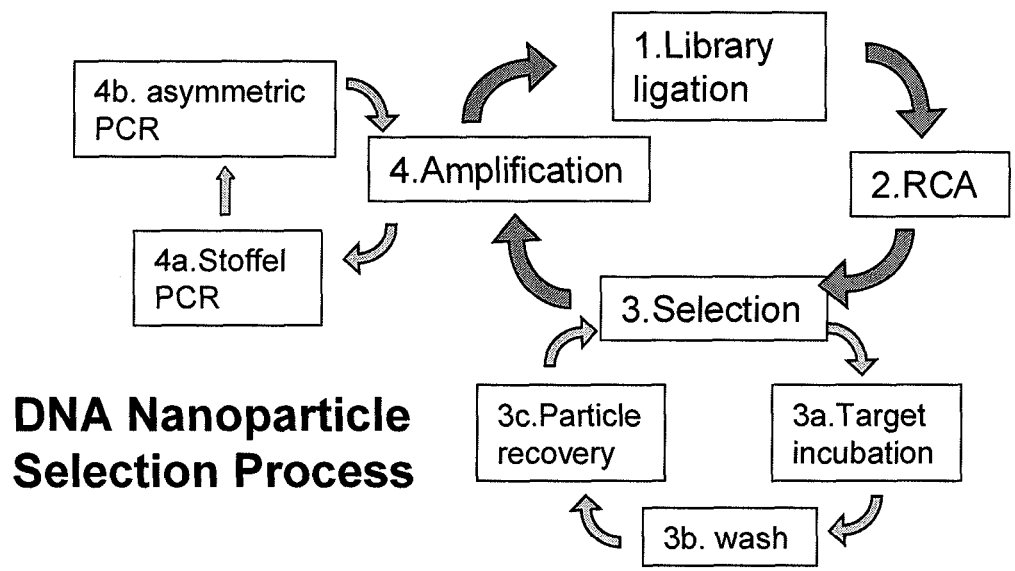
FIG. 7 relates to a DNA nanoparticle selection process.

Two cell lines, K-562 and NCI-H23, are used to test and optimize the multimodal DNA nanoparticle selection methods. Each round of selection consists of 4 essential steps and the molecular biology is the same regardless of selection scheme (FIG. 7).

Library Ligation

The template oligonucleotide is mixed with the ligation primer in T4 ligase buffer to final concentrations of 100 nM and 300 nM respectively. The mixture is heated to 95° C. and allowed to cool slowly to room temperature. T4 ligase is added and the reaction incubated for 1 hour at 37° C. For multimodal libraries, there are multiple ligation primers, and all but one primer are dideoxy terminated so that each multimodal template circle is primed at only one location.

RCA

Figure 8:
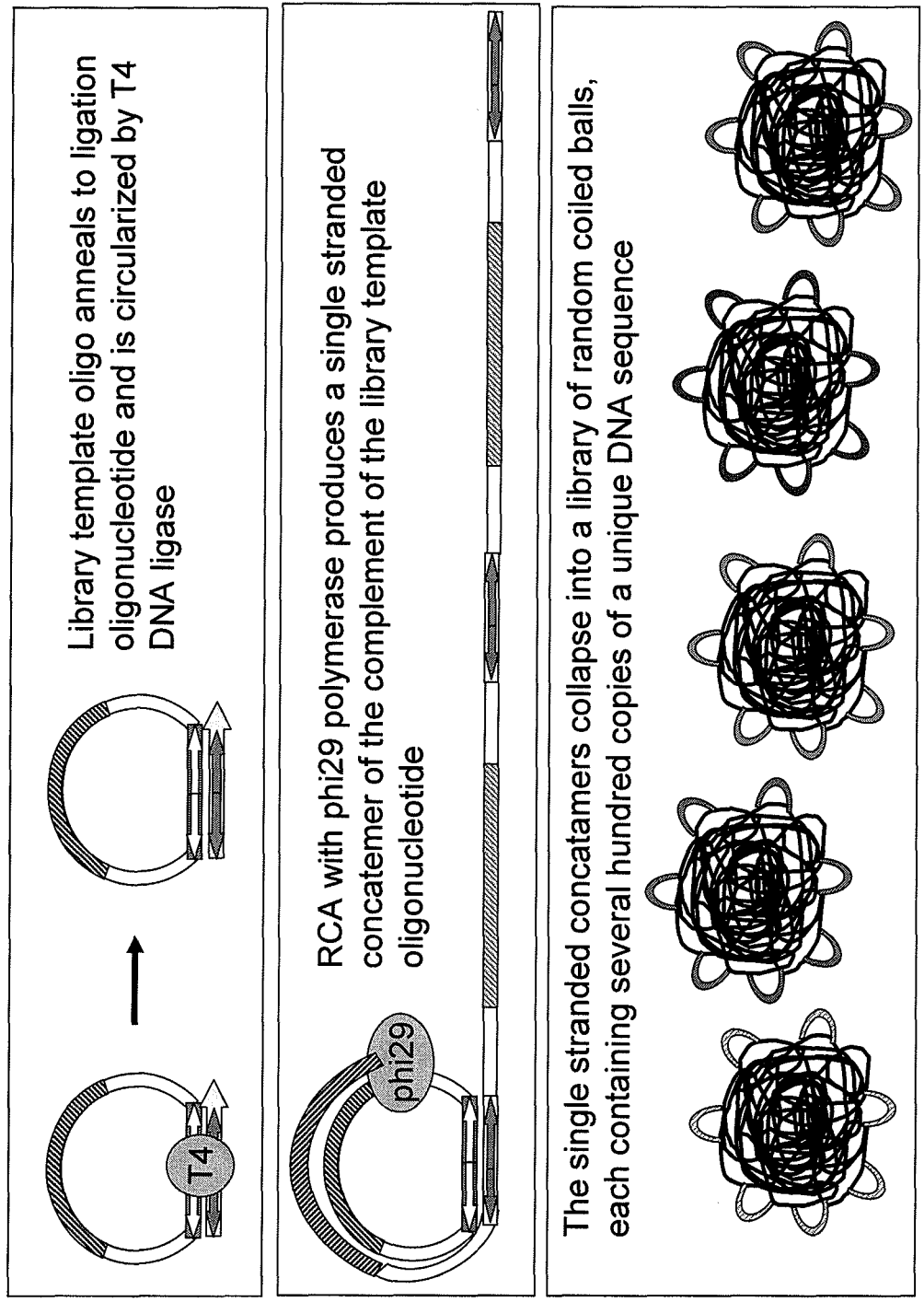
FIG. 8 relates to an embodiment that includes library generation, ligation, and RCA.

The ligation mixture is added to an RCA reaction mix containing phi29 polymerase. The final concentration of the ligated template oligonucleotides is 1 nM, meaning that in a 100 μl reaction ~6×10$^{10}$ DNA nanoparticles are created. When the initial library is made each of these particles will contain a unique sequence. The reaction proceeds for 30 minutes at 30° C. and is terminated with EDTA. This produces particles ~250 nm in size. The RCA reactions are monitored in real time with Oligreen, a single and double stranded DNA binding fluorescent dye, to confirm linear amplification. Since the amount of template DNA ligated and amplified is the same round to round, this rate should be constant and thus serves as a quality control checkpoint (FIG. 8).

Selection

Step A. The selection step can be performed in several ways, depending on the application. In one embodiment, the particles are incubated with the cell target of choice. If non-specific cell binding is recovered, subtractive approaches can be used in which the library is first or concurrently counter selected against an irrelevant cell target to remove non-specific cell binding. This can be done by preincubating the library with the irrelevant cell to absorb non-specific binding or, if the target and irrelevant cells can be easily separated, the library can be added to a mixture of both with the target cells then later removed. Typical incubation times are 30 minutes to an hour at either room temperature or 37° C. 10$^5$ cells are mixed with the entire RCA reaction from step 2. Step B. Washing is performed by centrifuging the cells and aspirating the liquid, then resuspending the cells and transferring to a new tube for the next wash. Three to five wash steps will be performed. Transferring to new tubes at each steps minimizes the recovery of plastic binding particles. Step C. Particle recovery. Since each particle is a concatemer of several hundred copies of the basic unit sequence, PCR amplification of single particles or even particle fragments is possible. Therefore, the particles can be recovered by lysing the washed cells followed by 1 hour treatment with proteinase K. The cell lysate is added to the PCR reaction in the next step, ensuring recovery of both external bound particles as well as particles that may have been internalized by the cells.

Amplification

Figure 9:
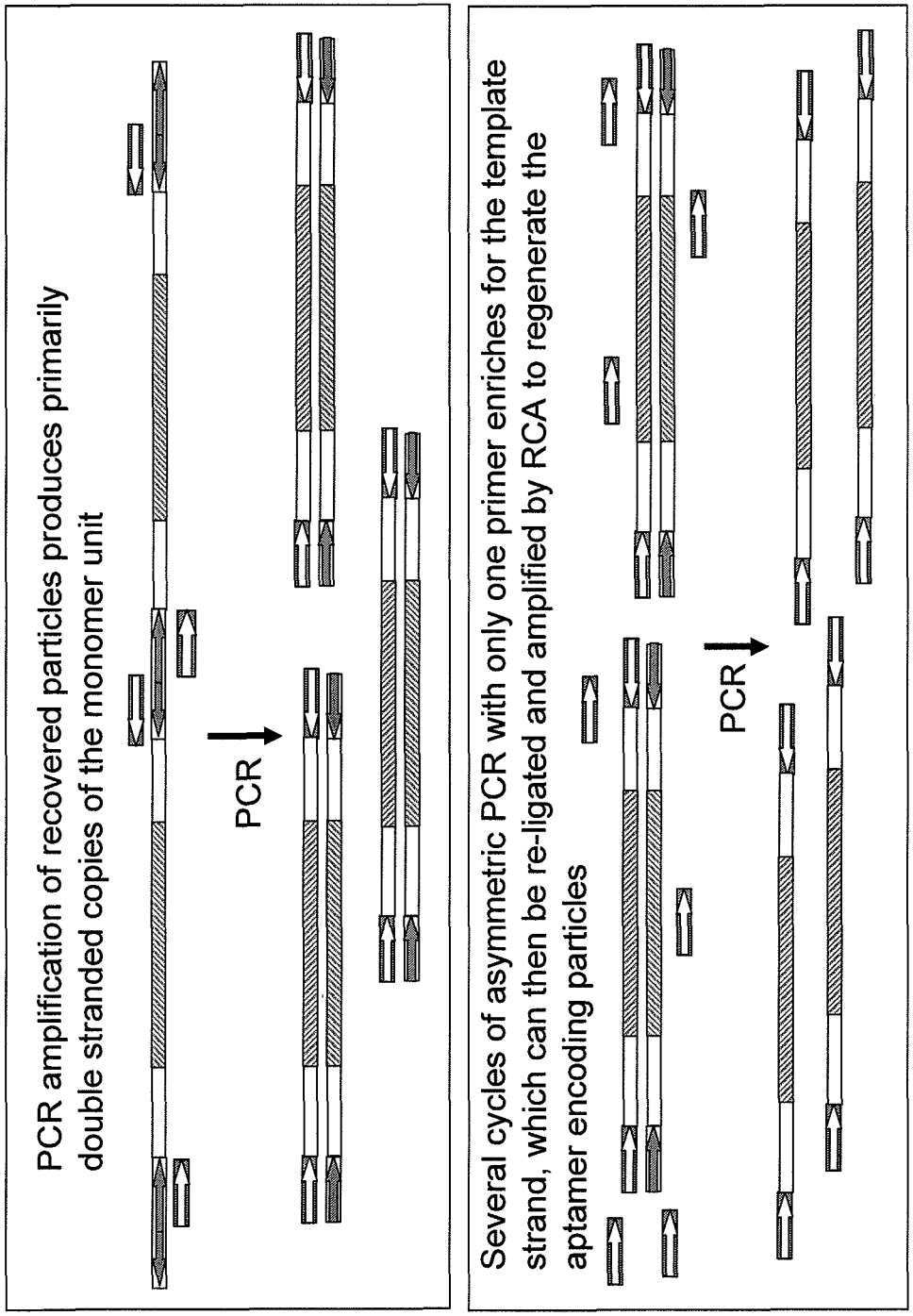
FIG. 9 relates to an embodiment that includes PCR amplification and asymmetric PCR.

One aim of the amplification step is to regenerate the population of template oligonucleotides that can be ligated and used to generate a pool of particles reflective of the particles recovered in the selection step. The main amplification is by PCR and the desired template DNA strand is secondarily enriched over the complement by asymmetric PCR using only the primer for the desired strand. a) Stoffel PCR. PCR amplification of these DNA nanoparticles is much more efficient when the Stoffel fragment of Taq polymerase, which lacks 5'-3' exonuclease activity, is used instead of conventional Taq polymerases, which has 5'-3' exonuclease activity. This may be because of the concatameric nature of the DNA particle strand, which could bind many primers in the initial rounds of PCR. The extending polymerase would run into the primed strand downstream of it and begin digesting, leading to very inefficient polymerization from the particle strand. The PCR reactions are monitored in real time with Sybr green and stopped once the production of PCR product plateaus. The real time plots also allow quantitative estimates of the relative amount of DNA, and by inference the number of particles, recovered in each round. b) asymmetric PCR. The PCR product is diluted into a new reaction mixture that contains only the primer that will produce the ligatable template strand. This primer has a 5' phosphate. The reaction is run for 10 cycles (FIG. 9).

After a successful selection, candidate particles are further analyzed from the final pool. To obtain individual particles, the final pool are amplified by Stoffel PCR and cloned into a plasmid sequencing vector. Once cloned, 10-20 candidates are sequenced to determine the extent of sequence diversity in the final pool. Each candidate can be regenerated by PCR/asymmetric PCR amplification from the plasmid.

Library Design and Selection Considerations

The design of each random module can be subject to some constraints. The minimum length of an oligo that can effectively circularize is reported to be around 80 bp. Since the flanking PCR/ligation primers sites are 30-40 bp, the randomized region can be at least about 40 bp. The potential diversity of any such library is much greater than the sample size. For example, a 60 bp library has $4^{60}$ different possible sequences, $\sim 1 \times 10^{36}$. Since typically $10^{10}$-$10^{11}$ particles can be created in a reasonable volume, only a tiny fraction is sampled of the possible number, and any particular batch of the library is a unique subset of the possible with each individual sequence represented by a single molecule. However, $10^{10}$ particles will likely contain any given 19 bp motif at least once and smaller motifs will be well represented within the sampled population.

When multimodal particles are created there is an additional combinatorial element. If 3 libraries of the size above are randomly combined into multimodal particles, then there would be $10^{30}$ different combinations, treating each module as a discrete entity. Since there may be limits to $10^{10}$ particles due to the physical constraints of particle synthesis, it may not be ideal to combine libraries in the first few rounds of selection. In fact, it is unlikely that any particular combination recovered in the first round would reform in the second while the remaining diversity is still high. On the other hand, if particular combinations of modules would be optimal together but are not particularly good on their own, then delaying combination of the library may result in the desirable modules disappearing from the population before they have a chance to team with the others for selective advantage. However, in the absence of a rigorous model of selection kinetics and fitness landscapes, an empirical approach can be used.

Figure 10:
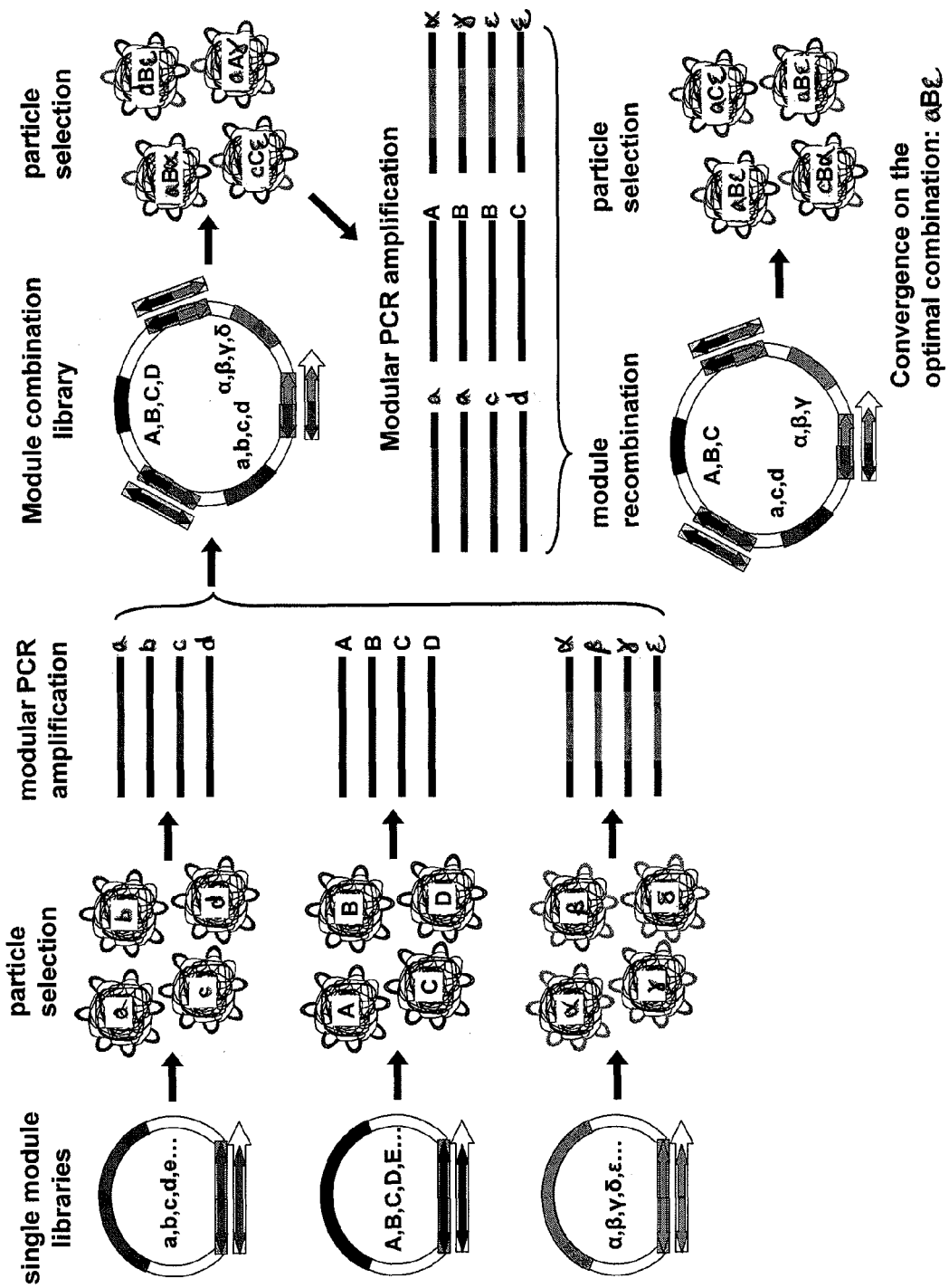
FIG. 10 relates to an embodiment that includes multimodule particle creation from single module libraries.

The overall concept of the modular library screening method can be divided into a "panning" phase, where binders within the population are selectively enriched, and a "breeding" phase in which the multimodal particles are re-assorted in each cycle so that novel combinations can be generated and the optimal combinations enriched (FIG. 10).

Figure 11:
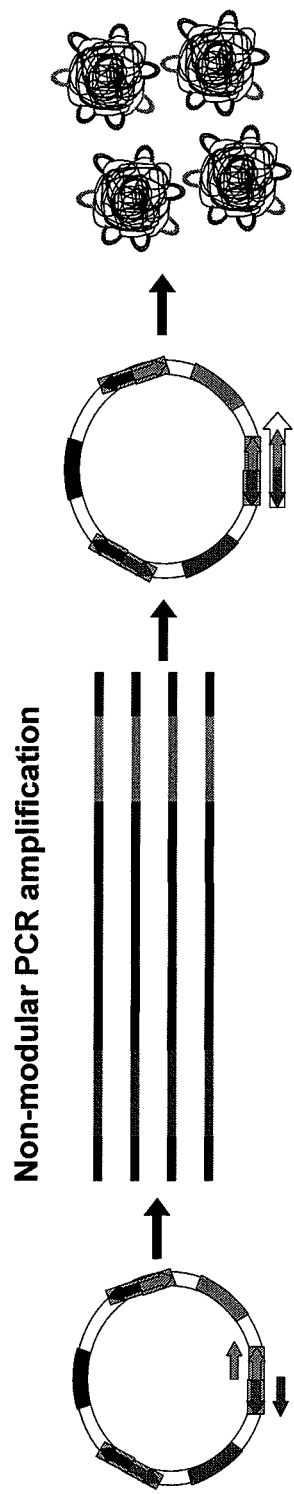
FIG. 11 relates to an embodiment that includes non-modular PCR amplification of multimodule particles to preserve module combinations.

Three selection schemes can be tried. In the first, the libraries are assembled into the multimodal format prior to the first round and in all subsequent rounds. However, for the first three rounds the particles are amplified as a single unit and the modules are not be re-assorted (FIG. 11).

Non-modular PCR ensures that any particular combination of modules that comes through the first round will be amplified to higher copy number before the re-assortment process begins. For subsequent rounds, the recovered particles are split and some amplified as a single unit by the non-modular method and the rest amplified as modules and recombined, ensuring representation of the selected combinations as well as generating new combinations of modules.

The second selection scheme attempts to pre-enrich the modular pool for desired activity by screening the single component libraries for several rounds prior to combination in multimodal format. The individual libraries are screened for 5-10 rounds until there is evidence in each of enrichment for binding clones (indicated by an increased in the number of particles recovered in each round as determine quantification from the real time PCR amplification step). The combinatorial strategy is then be pursued for several rounds. The final strategy is a hybrid of the first two. Three to five rounds of selection are performed with each of the component libraries, and then the following rounds are done using only the combinatorial approach.

Protocols can be optimized against K-562 and NIH-H23 cell lines. Single module library selections can be run in parallel. To determine the optimal method, the particles can be evaluated for cell binding affinity and specificity. The affinity can be measured by adding equal numbers of particles to the cells and quantitating the bound number by quantitative PCR after stringent washing. Specificity can be assessed by performing the same experiment against the reciprocal cell line and taking the ratio of the two. If specificity is not achieved, then the selections can be repeated with a subtractive step using the other line included. Finally, the individual modules of any multimodule particles can be independently amplified, ligated, and tested in the single module particle format to determine if each module is contributing to the overall binding of the multimodule particle.

While the library selection schemes do not require a priori knowledge of the particular molecules on the target cells surface, particles that are specific for the cell target of interest can be used to identify the cell surface molecules. The particles can be used in pull down experiments with target cell extracts and the bound proteins identified by mass spectrometry (Mallikaratchy P, et al. Aptamer directly evolved from live cells recognizes membrane bound immunoglobin heavy mu chain in Burkitt's lymphoma cells. Mol Cell Proteomics. 2007; 6:2230-2238).

Methods to Create Particles that Bind to Lung Cancer and Leukemia Derived Cell Lines.

Figure 12:
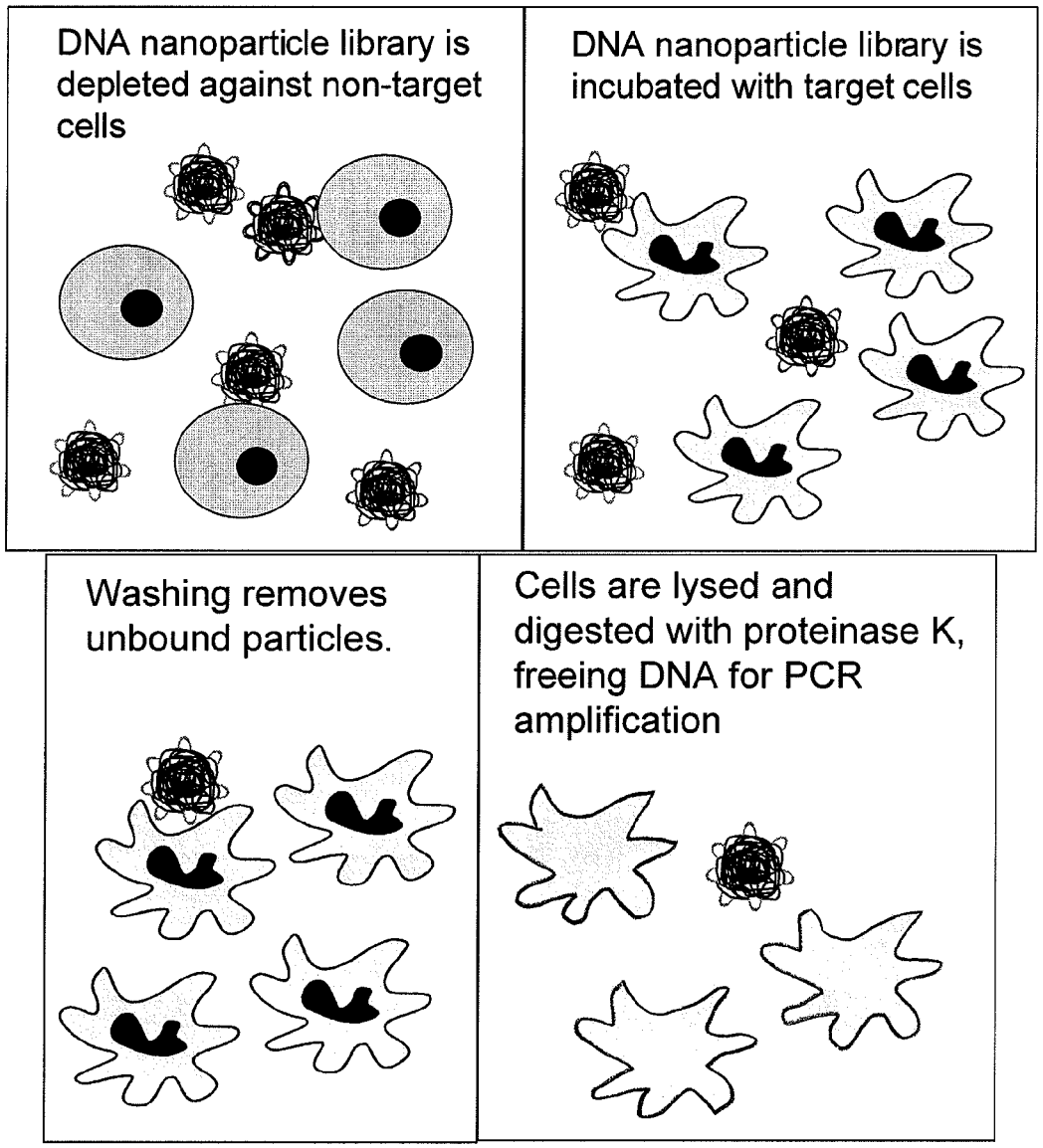
FIG. 12 relates to an embodiment that includes subtractive screening. An irrelevant cell line is used to absorb non-specific cell binding particles.

The optimal selection strategy described herein can be applied to four additional lung cancer cell lines such as NIH-226, NCI-H322M, NCI-H460, and NCI522, and four additional leukemia derived lines, such as, CCRF-CEM, HL-60, Molt-4, and RPMI-8226L. These cell lines are members of the NCI-60 panel of well defined cancer cell lines. Since a desirable particle for many applications can be one that binds broadly to tumors of a particular type, these panels can be used in two ways. First, selections against each with subtraction against a normal line or one of the other tumor lines can be performed (FIG. 12).

Candidate particles from each of those can be tested against the other cell lines of the same cancer type to identify cases where broad selectivity may have been achieved by serendipity. Conversely, broad specificity can be selected for in the selection protocol by pooling cell lines and/or alternating the target cell line or target cell pools in each round, thus providing a selective advantage to particles that bind to all of the cell lines used. This approach is applicable to lung cancer lines.

The leukemia derived lines come from several different types of leukemia, including acute and chronic myeloid, acute lymphoid, and plasma cell myeloma. In addition to devising selections that will favor broad specificity to all of the lines, particles that recognize the lymphoid derived but not the myeloid derived lines may be recovered (and vice versa).

Methods to Demonstrate Cancer Specific Cell Binding of Selected Particles

Particles selected for using the methods described herein can be evaluated in at least three formats: flow cytometry, histology by fluorescent microscopy, and cell capture. These three techniques are generally reflective of most ex vivo applications of cell affinity reagents.

Flow Cytometry

DNA nanoparticles can be coupled to fluorophores in at least three ways. 1) Fluorescent nucleotides can be used during the synthesis step, 2) DNA binding fluorescent dyes can be added after synthesis (though these must be cell impermeant for the applications here), or 3) fluorescently labeled oligonucleotides can be hybridized to the particles after synthesis. The first of these, labeled nucleotides, is has been done successfully with Alexa488 labeled nucleotides (see data herein).

Labeled DNA particles can be used in the same way as labeled antibodies. The particles are incubated with the fixed cells, the cells washed, and the sample run on a flow cytometer (see data herein). The particles do not affect the forward or side scatter of the cells and unbound particles, while detectable by their fluorescence, do not scatter sufficiently on their own and can be gated out. Multiple particles can be used if they labeled with compatible fluorophores.

Histology/Fluorescent Microscopy

The fluorescently labeled particles can be assessed in fluorescent microscopy. Initially, the particles can be tested against the cognate cell lines that have been cytospun onto slides. Specificity can be assessed by creating slides with mixtures of the cognate and other cells at defined ratios. Standard cell staining protocols can be used and the various parameters (incubation times, DNA nanoparticle concentration, etc) optimized.

Figure 13:
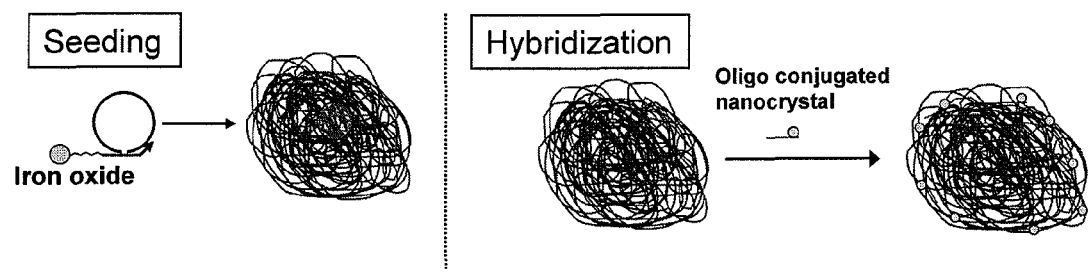
FIG. 13 relates to two methods of introducing paramagnetic properties to the DNA nanoparticles via iron oxide-oligonucleotide conjugates.

Commercial tissue arrays (MaxArray, Invitrogen) can be used to determine the specificity of the particles that bind to lung cancer derived lines. Multi-tumor and normal arrays can be screened first to determine the specificity, and then lung cancers arrays can be used to determine the sensitivity against many different samples. It is possible, if not likely, that different particles can have different profiles when so compared. For histological applications it may be useful to use a pool of particles to ensure the broadest binding to a given cancer type Cell Capture The DNA nanoparticles can be used to capture and isolate their target cells in several ways. The particles can be labeled with biotin by either incorporation of biotinylated nucleotides during the synthesis or by hybridization of a biotinylated oligonucleotide after the synthesis, as for the fluorophores described herein. Biotinylated particles can often be captured along with the cells they are stuck to using streptavidin coated magnetic beads. Alternately, the particles themselves can be made magnetic through the coupling of iron oxide nanoparticles. An iron oxide nanoparticle can be conjugated to the seeding primer in a 1:1 ratio such that when the reaction proceeds the iron oxide will be embedded inside the DNA nanoparticle. The 1:1 conjugated oligo-iron oxide structures can be used as hybridizing oligonucleotides to a DNA nanoparticle scaffold (FIG. 13).

To assess capture efficiency, the target cell lines can be mixed with irrelevant cell line and the capture efficiency determine. The cells can be incubated with the DNA nanoparticles then, in the case of the biotinylated particles, mixed with magnetic streptavidin coated beads.

Some embodiments include methods to validate and optimize combinatorial selection of libraries. Some embodiments can demonstrate that 10 DNA nanoparticles each containing 3 unique recognition elements can be amplified and reassorted to create more than 50% increase in library diversity i.e. the sequences of more than 10 out of 20 resorted clones will be different from the original 10. Some embodiments can identify at least 1 multimodal particle that binds to the target cell line 10-fold better than a random control particle. Binding can be defined by quantitation of recovered DNA by quantative PCR (QPCR) after incubation with the target cells and washing as in the selection protocol.

Some embodiments include methods to select particles against a panel cancer cell lines. Some embodiments can utilize at least 6 of the 10 cell lines, and select at least one binding particle. Some embodiments can select at least 1 particle that has a 3 fold increased binding to a targeted cancer cell line relative to the normal cell line. Some embodiments can select at least 1 particle that exhibits 3-fold increased binding to 3 or more cell lines from the same cancer relative to the normal line Some embodiments include methods to demonstrate cancer specific cell binding of selected particles. Some embodiments include utilizing particles that results in a mean fluorescent intensity 5 fold greater when used against the target cell line compared to an irrelevant cell line. Some embodiments include demonstrating at least one particle or pool of particles that results in a fluorescent intensity at least 2 fold greater on the targeted cell line vs a control cell line. Some embodiments include demonstrating at least one particle or pool of particles that fluorescently stains lung cancer tissue with a 2 fold greater intensity than normal tissue. Some embodiments include demonstrating capture of 1 cell in 100 using a leukemia specific particle.

Immunotherapy and Targeting Cancer

Immune therapy of cancer seeks to activate the body's own immune system to destroy both primary and disseminated tumors. This attractive idea has not met with much success in the clinic in part because of the lack of good immune adjuvants. A novel selectable DNA nanoparticle library technology has been developed. DNA nanoparticles (DNA-NP) are generated by rolling circle replication (RCA) of a circular template oligonucleotide. The resulting complementary single stranded concatemer collapses into a random coiled nanoparticle. Using this approach, DNA-NP have been identified that, by virtue of their sequence, bind specifically to DC, are taken up, and induce $Ca^{2+}$ flux and IL-6 secretion. DC binding DNA-NP can be further refined and tested for their ability to activate immune responses in a mouse melanoma model. DNA and other nucleic acids have a long clinical history and offer a streamlined path to the clinic.

Some embodiments include methods to develop a DNA-NP capable of inducing an immune response to an existing tumor. Without wishing to be bound to any one theory it is believed that targeted DNA nanoparticles that bind to and stimulate dendritic cells (DC) can cause immune activation and lead to anti-tumor immune responses.

Some embodiments include methods to screen and rank DNA-NP that activate DC. Data shows the selection of DNA-NP that selectively bind to and stimulate DCs. The hypothesis that DCs stimulated with DNA-NP mature into antigen presenting cells capable of T cell stimulation in vitro can be tested. One of the strengths of the methods described herein is that multiple distinct sequences can be easily combined to make combinatorial hybrid particles. Combinations of DC binding particles can likely cause greater DC activation than each given individually or in combination as distinct particles. The most active particle can proceed to in vivo tests.

Some embodiments include methods to relating to direct injection of DNA-NP into tumors that can activate tumor infiltrating DC. The mouse B16-OVA melanoma model can be used. DNA-NP can be injected into established tumors and the activity on tumor infiltrating lymphocytes determined by histology (CD11c & T) and cytokine analysis. If robust responses are observed the particles can be optimized for size and backbone composition and the effect on tumor growth determined.

Some embodiments include methods that relate to immunization with DNA-NP and model tumor antigens elicit antigen specific responses and tumor rejection. The mouse B16-OVA melanoma model can be used. The hypothesis that immunization with ovalbumin or peptides derived from it together with the DNA-NP produces an antigen specific immune response in normal healthy mice can be tested. If robust responses are observed immunized tumor bearing mice can be tested. If systemic immune responses are weak, the hypothesis that intra-tumoral immunization will produce anti-tumor responses can be tested. The dependence of those responses on T cells will be analyzed in mice depleted of $CD4^+$ or $CD8^+$ cells.

Methods and compositions provided herein can provide pre-clinical data important to begin planning human clinical trials. Possible toxicity of the DNA nanoparticles can be carefully monitored, particularly excessive inflammatory or autoimmune responses and, where possible, pharmacodynamics can be evaluated.

Background and Significance

Immune therapy in cancer has a long history marked by striking anecdotal successes but few generally successful strategies. Anton Chekhov and William Coley noted the relationship between infection and cancer regression in the late 1800s, with the latter developing "Coley's Toxin", a mixture of killed *Streptococcus pyogenes* and *Serratia mercescens* as a treatment for cancer (Gresser I (1987) A. Chekhov, M.D., and Coley's toxins. N Engl J Med 317: 457). Modern approaches seek to activate the immune system using defined stimulators of immune cells such as cytokines or toll-like receptor (TLR) agonists, in place of bacterial preparations (though Bacillus Calmette-Guerin (BCG) is still used in the clinical treatment of bladder cancer) (Herr HW, Morales A (2008) History of bacillus Calmette-Guerin and bladder cancer: an immunotherapy success story. J Urol 179: 53-6).

Immunotherapies have shown promising results in several cancers (Figdor C G, et al., (2004) Dendritic cell immunotherapy: mapping the way. Nat Med 10: 475-80). Cytotoxic T lymphocytes (CTLs) play a major role in eliminating malignant cells by specifically recognizing antigenic peptides presented on MHC class I molecules by dendritic cells (DC) (Nguyen T, et al., (1999) Recognition of breast cancer-associated peptides by tumor-reactive, HLA-class I restricted allogeneic cytotoxic T lymphocytes. Int J Cancer 81: 607-15). Peptides derived from tumor-associated antigens (TAA) have been identified for some forms of human cancers (Minev BR, et al., (2000) Synthetic insertion signal sequences enhance MHC class I presentation of a peptide from the melanoma antigen MART-1. Eur. J. Immunol. 30: 2115-2124). Thus far, however, effective peptide vaccination of cancer patients has been limited to very few trials and for most cancers the antigens are not identified. DCs are the most potent antigen presenting cells. In addition to taking up the antigen, DCs also need to receive a maturation signal in order to activate CTLs to perform their cytotoxic functions. If DCs take up antigen without receiving a stimulus, they can induce tolerance. Two central hurdles in immunotherapy are: (1) In many instances tumor-specific CTLs though present in patients, are in a tolerant/nonresponsive state. One of the major challenges for tumor immunotherapeutic approaches is to break this tolerance to achieve CTL-mediated killing of tumor cells. (2) For most tumors the antigens are unknown and possibly patient and tumor specific. Consequently, methods to overcome these obstacles should lead to a marked improvement in antigen presentation and induction of potent anti-tumor CTL.

Certain immunostimulatory molecules, from TLR agonists such as CpG DNA and poly(I:C), to cytokines, have been tried in one form or another, but general principles have been difficult to elucidate and the need for more potent immune adjuvants remains acute. Interferon alpha and interleukin 2 are approved for the treatment of melanoma. Systemic administration of CpG oligonucleodies has been moderately successful in mouse models and clinical trials, suggesting that specific tumor antigens need not be included in a successful therapy.

The immune system may be far more sensitive to stimulation with multivalent and multifunctional particle delivery mechanisms, perhaps mimicking virus and bacteria. The primary cell responsible for initiating and directing an anti-tumor cytotoxic T cell response is the dendritic cell, though B cells can also serve in that role to some extent. Dendritic cells uptake antigen by endocytosis and pinocytosis, but they must also encounter an immune stimulus to mature into robust antigen presenting cells. Therefore, targeting adjuvant activity to DCs is an obvious route to enhance the potency of an adjuvant. This has been attempted in in several ways, including antibodies that bind to DC restricted membrane antigens such as DEC-205. Targeting antigen to DCs in lymphoid tissue using antibodies against DEC-205 in conjunction with an adjuvant led to increased induction of immune responses. Thus using molecules that target DC is a very promising approach to enhance immune response to cancer. However, antibodies, need to be humanized and are expensive to produce.

Chemically diverse libraries are a rich source of potential ligands for biomolecules and cellular targets of interest. When modular biopolymers such as nucleic acids or polypeptides are used, the combinatorial diversity of these libraries can become astronomical and well beyond the capabilities of systematic high throughput screening methods. Combing these libraries requires iterative schemes that couple a selection step with an amplification step. For peptides, display of a given peptide on a bacteriophage, virus, or bacteria allows amplification by growth of the host organism. Nucleic acids are typically amplified by some variation of PCR (Tuerk C, Gold L (1990) Systematic evolution of ligands by exponential enrichment: RNA ligands to bacteriophage T4 DNA polymerase. Science 249: 505-10). Subtractive and in vivo selection schemes have been developed for aptamer and phage displayed peptide libraries that can enhance the cell specificity of recovered targeting ligands (Siegel D L, et al., (1997) Isolation of cell surface-specific human monoclonal antibodies using phage display and magnetically-activated cell sorting: applications in immunohematology. J Immunol Methods 206: 73-85). Cellular targeting has been demonstrated by libraries of peptides and oligonucleotide aptamers (Rasmussen U B, et al., (2002) Tumor cell-targeting by phage-displayed peptides. Cancer Gene Ther 9: 606-12; Hicke B J, et al., (2001) Tenascin-C aptamers are generated using tumor cells and purified protein. J Biol Chem 276: 48644-54).

However, peptide and aptamer libraries have some distinct limitations. Many peptide display formats, such as phage, present many copies of each peptide per particle. This can allow the recovery of relatively low affinity interactions that benefit from the high avidity of the presentation format. However, it may be difficult to maintain the desired binding avidity and specificity when the selected peptides are moved to another particle or molecule. Aptamer libraries can suffer from the reverse complication since they are usually presented in a monovalent format. Aptamers have been most clinically useful when a high affinity interaction can function in an antagonist manner, though they have been used as targeting moieties attached to nanoparticle drug delivery vehicles. However, when aptamers that were selected in a monovalent format are attached to particles in a multivalent way, specificity can be lost as low affinity interactions gain avidity. In addition, there is always a concern that the transfer or attachment of a peptide or aptamer to a new molecule or particle may alter its conformation and binding affinity for the target of interest. Thus for targeting moieties on particles, it would be advantageous to select the optimal ligand in the context in which it will be used.

Figure 14:
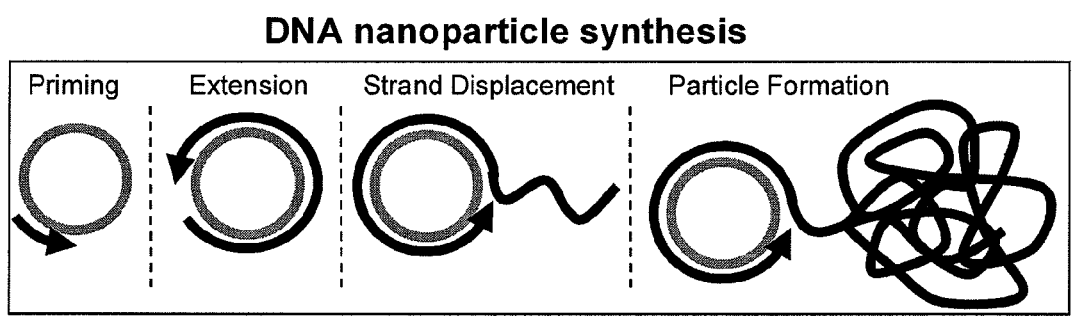
FIG. 14 relates to an embodiment of DNA-NP synthesis by rolling circle amplification.

The paradigm of nanotechnology for applications in the medical field has been oriented around the framework of bottom-up construction. Generally, a scaffold of polymer or metal serves as a basis for the addition of functional moieties to lend the nanomaterial the desired capabilities such as selective targeting, transport of therapeutic and imaging agents, and immune evasion. When biopolymers such as DNA are used, they are often rationally designed to form a predetermined structure (Zhang C, et al., (2008) Conformational flexibility facilitates self-assembly of complex DNA nanostructures. Proc Natl Acad Sci USA 105: 10665-9). However, this approach has overlooked a powerful tool of molecular biology: the simple creation and efficient combing of libraries with diversity of $10^9$ or more. Small nucleic acid aptamer sequences have been identified with binding and enzymatic properties, but their use in nanoparticle based applications has mostly involved grafting them onto other materials. An overview of methods of diverse library selection with nanoparticles to create libraries of DNA nanoparticles by rolling circle replication of randomized circular templates and selecting for particles that bind to a target cell type is shown in FIG. 14.

Production, Characterization, and Purification of DNA Nanoparticles by Rolling Circle Amplification DNA nanoparticles are produced by enzymatic DNA synthesis using a strand displacing DNA polymerase, phi29, and a circular oligonucleotide template.

The oligonucleotide circle is typically produced by ligation of a 100-200 base pair linear oligonucleotide with a short (30 bp) oligonucleotide complementary to the ends. The ligation oligonucleotide also serves as the initiating primer for the RCA reaction. Phi29 polymerase is highly processive (~70 kb) and produces a linear increase in single stranded DNA for over an hour in a typical reaction. Phi29 can also incorporate phosphorothioate backbone nucleotides, although the rate of polymerization is slower (FIG. 15).

Figure 16:
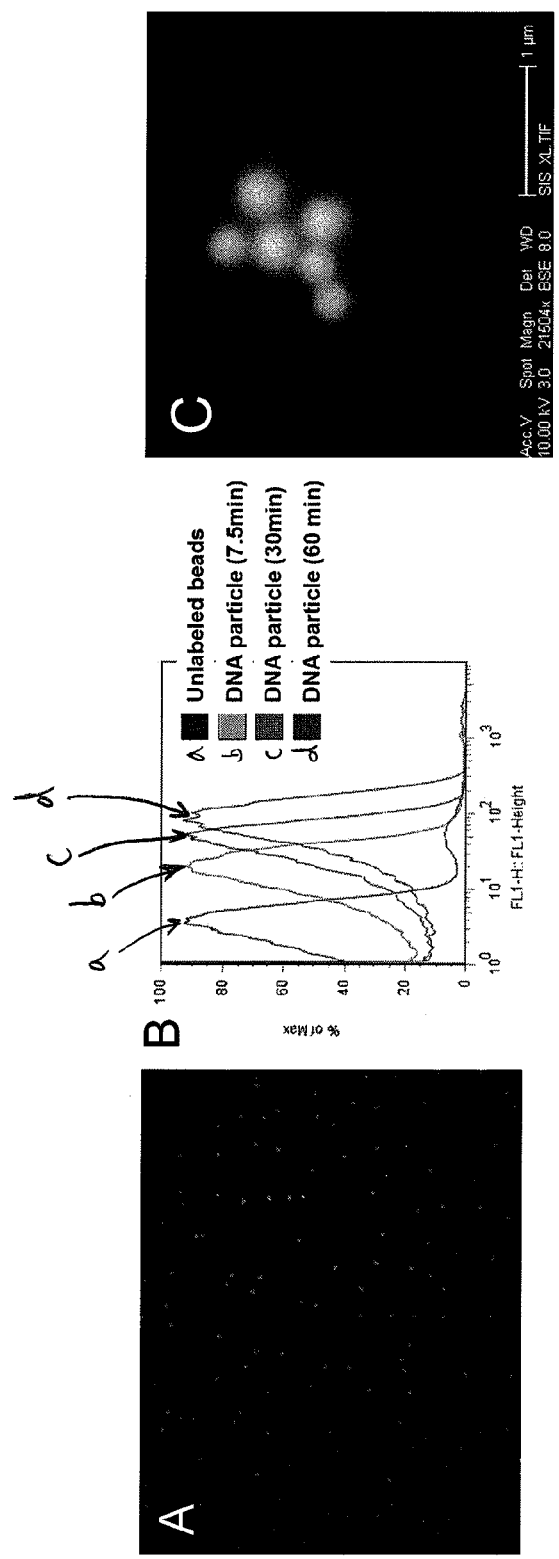
FIGS. 16A-16C provide data relating to a visualization of DNA nanoparticles.

The resulting RCA produces are concatemers complementary to the template circular oligonucleotide. These long single stranded products collapse into randomly coiled nanoparticles, a property that has been exploited for counting individual RCA events (Jarvius J, et al., (2006) Digital quantification using amplified single-molecule detection. Nat Methods 3: 725-7). The size of the particles is a function of the time and efficiency of the RCA reaction. The reaction can be stopped by the addition of EDTA or heat inactivation of the phi29 polymerase, though the latter may lead to aggregation of the DNA particles. The particles can be visualized with either single stranded or double stranded fluorescent DNA binding dyes due to the double stranded character that results from internal base pairing. For analytical purposes the particles can be made fluorescent by the inclusion of fluorescently labeled nucleotides during the synthesis. Alternately a fluorescently labeled oligonucleotide probe can by hybridized to the particles (FIGS. 16A-16C).

It is difficult to size the particles by conventional or denaturing gel electrophoresis due to their large size and single stranded character. Dynamic Light Scattering (DLS) is a common technique for measuring the properties of nanoparticles such as size and zeta potential. DLS uses the time autocorrelation of a signal of scattered light to determine the polydispersity and average diffusion coefficient, which through the Stokes-Einstein equation is related to the average dynamic radius. RCA reactions were carried out for four time points (10, 30, 45, 60 minutes) and were stopped by the heat inactivation of the polymerase at 65° C. for 10 minutes. The samples are then immediately measured by DLS. For a monodispersed sample the autocorrelation plots should show a single exponential decay, the exponent coefficient of which is known as the first moment and is used to calculate a Z-average size. The second moment is used to calculate the deviation from monodisperse and is known as the polydispersity index (PdI), which is a measure of relative peak width of the Gaussian size distribution.

Figure 17:
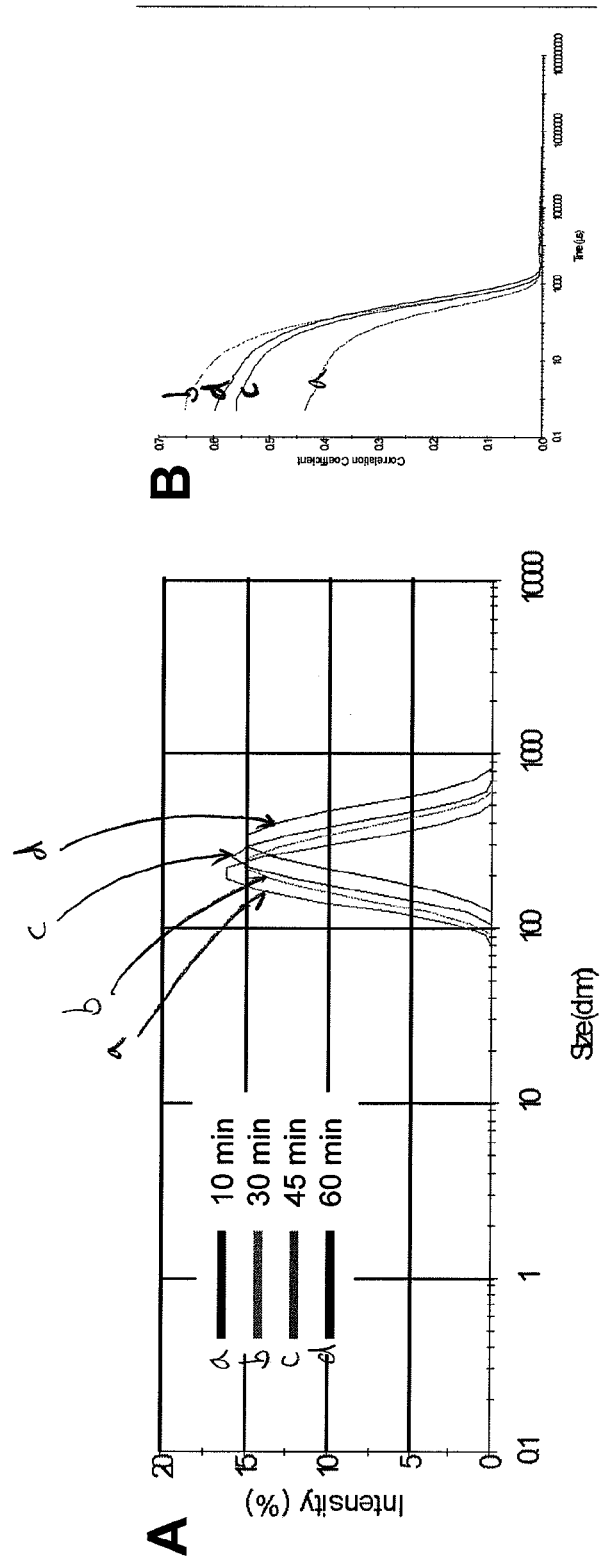
FIGS. 17A-17B relate to DNA nanoparticles sized by Dynamic Light Scattering (DLS).

As seen with flow cytometry, the average particle size increases as the reactions are allowed to proceed for longer. We have noticed in other batches that the size seems to peak around 300 nm, even with longer reaction times. These measurements are in good agreement with a freely joined chain model of polymer condensation which estimates a 60 kb ssDNA strand to have a hydrodynamic radius of 379 nm. It is suspected that the size of the particles may be limited by the processivity of the phi29 enzyme and steric hindrance as the particle grows. However, once reaction conditions are fixed, the size of the particles is reproducible batch to batch and can be tuned from roughly 100-300 nm. The optimal size for a given application must be determined experimentally, and the notion of "size" may be somewhat of an anachronism for a flexible polymer condensate. Electron microscopy is underway to obtain a higher resolution image of the particles at various stages of growth (FIGS. 17A-17B).

DNA-NP are purified by size exclusion chromatography and dialysis, and concentrated by centrifugal membrane concentration. After the RCA reaction there are significant excess free nucleotides that should be removed before the particles are used for other experiments. Special care is taken to avoid any possible LPS contamination, including the use of dedicated glassware and columns. Negative control particles are always purified in the same way on the same apparatus with the same buffers.

DNA Nanoparticle Library Selection Method

A method to generate high diversity libraries of DNA nanoparticles and select for those with desired features through an iterative screening and re-amplification method has been developed. See Examples.

Individual particles were obtained by cloning the PCR amplification products from the 7$^{th}$ round of selection. 15 clones were sequences and all but one were unique. Each clone was used to generate fluorescently tagged DNA nanoparticles and these were screened against DCs by flow cytometry. Several of the clones showed good binding to the DCs. Clone 3 was chosen for further evaluation. Particles that bind to breast cancer, ovarian cancer, and pancreatic cancer derived cell lines as well as particles that bind to adenovirus have been selected.

Specificity DC Binding DNA-NP

Figure 18:
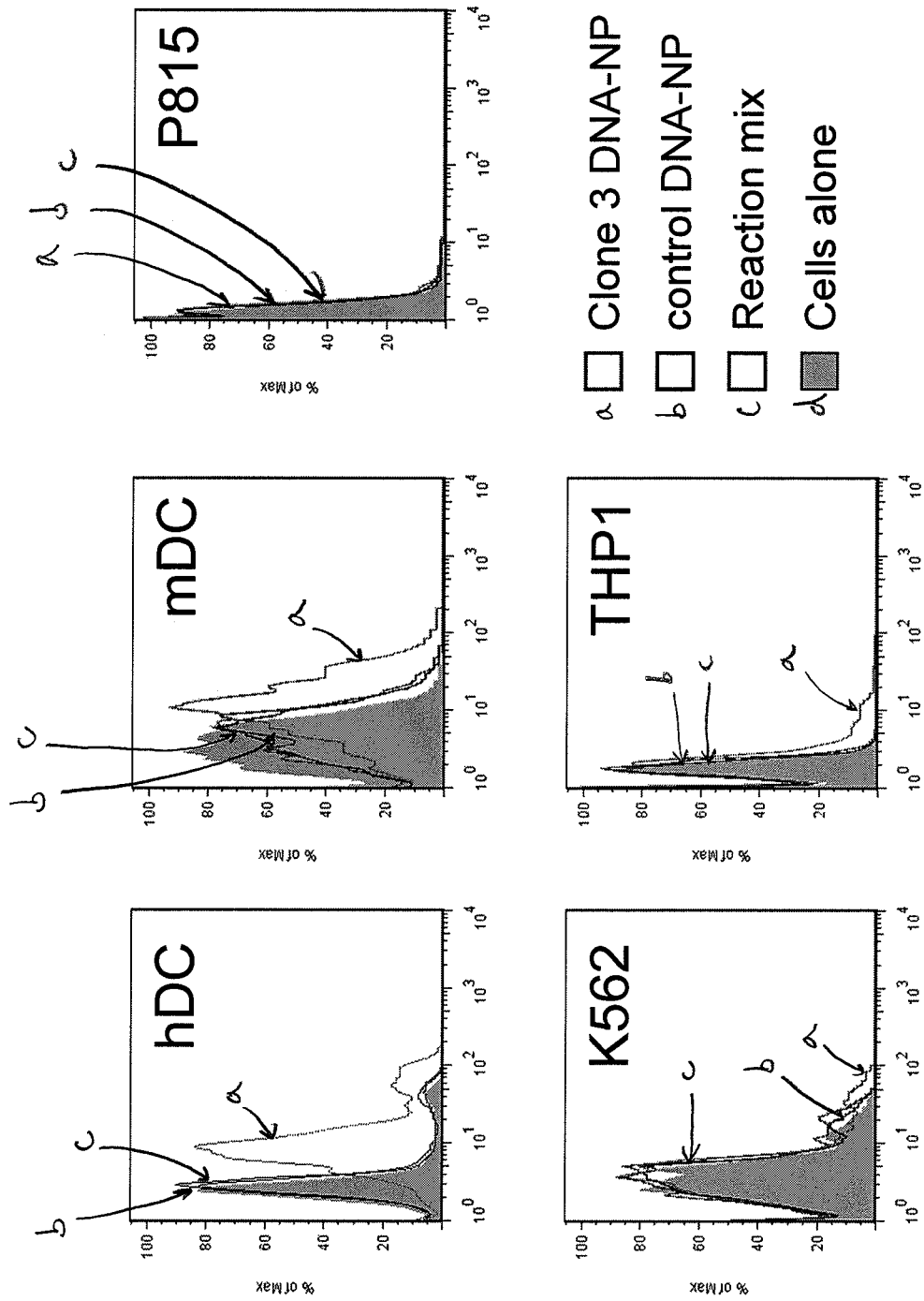
FIG. 18 relates to the specificity of DC binding clone 3. Particles were labeled and tested as described herein.

Further characterization DC binding clone 3 was undertaken. The specific of the cell binding was investigated with several other cell type and cell lines. DNA-NP were made fluorescent by the incorporation of alexa488 tagged nucleotides during the synthesis. Controls include a particle with the reverse complement sequence to clone 3 and the reaction mix with the labeled nucleotides. In addition to the cell types shown in the figure, we have seen no binding to primary Chronic Lymphocytic Leukemia cells or the RAMOS cell line. We have observed binding of clone 3 to human monocytes and macrophages, albeit it at a lower level for the former. Significantly, the clone 3 DNA-NP binds to mouse as well as human DC (FIG. 18).

Figure 19:
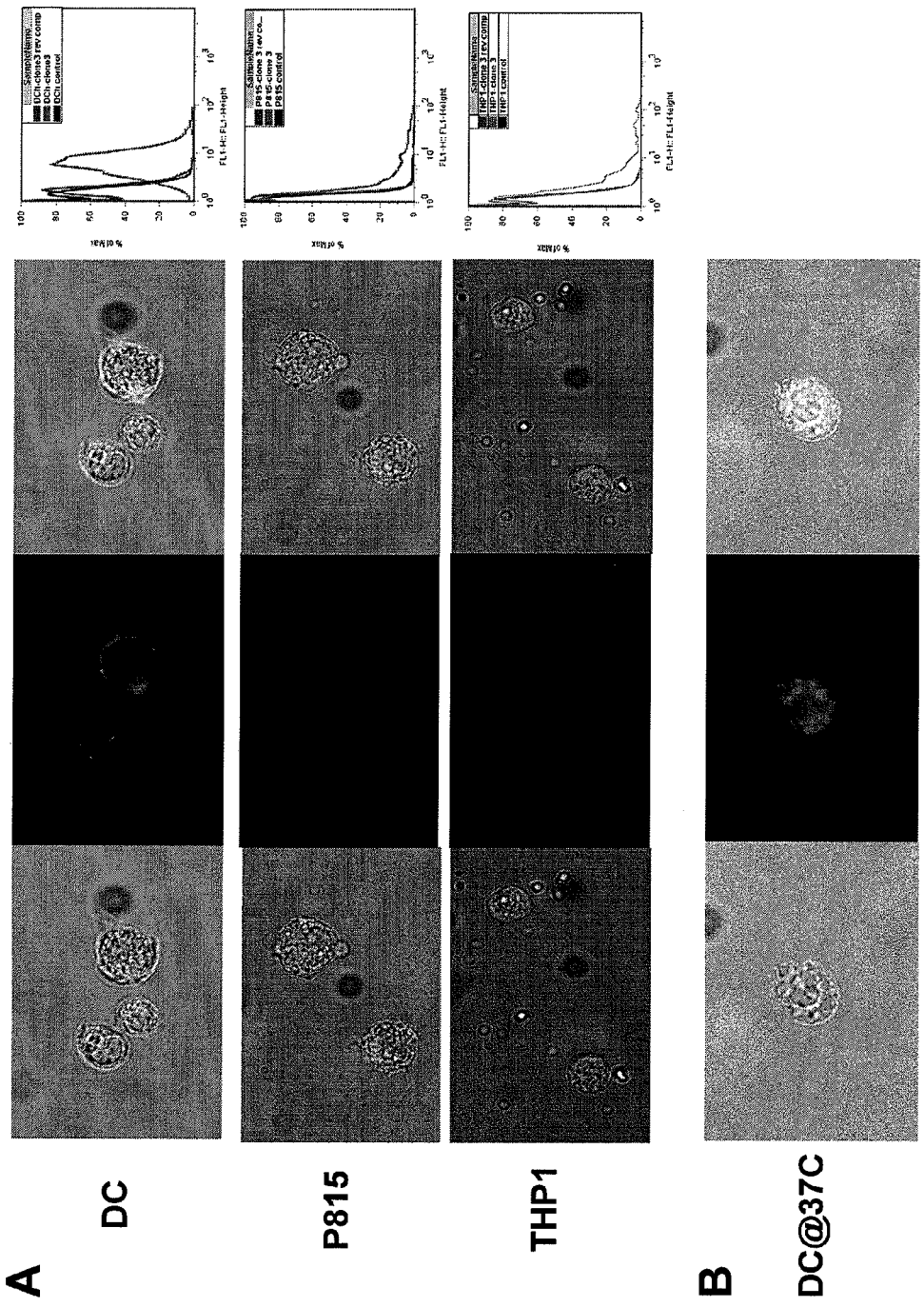
FIGS. 19A-19B provide data relating to specific binding and uptake of Clone 3 by DC.

The results above were confirmed by fluorescent microscopy (FIGS. 19A-19B). Since all selections and binding experiments to this point were performed on ice, it was confirmed that the clone3 DNA-NP bound DC at 37° C. by flow cytometry (data not shown). Furthermore, when DC were incubated with clone 3 DNA-NP at 37° C., the pattern of staining suggested that the DNA-NP had been taken up. Preliminary confocal microscopy has supported this interpretation but has not been confirmatory to date.

It was confirmed that clone 3 reproducibly binds by using separate batches of particles and synthesizing particles from both the original clone (PCR from bacteria colonies harboring the clone, followed by assymetric PCR with a 5' phosphate on only the desired primer for subsequent strand ligation and RCA) or from a synthetic oligonucleotide template with the same sequence. In addition, it was tested that the stability of particles kept at −20° C. and 4° C. for several weeks; no loss of activity has been observed.

DC Binding DNA-NP Activate DC

DC binding DNA-NP may cause DC activation through changes in cytokine secretion, signaling, and surface marker expression. IL-6 secretion is a commonly used indicator that DC have matured into immune activating cells, though a full cytokine secretion profile is ultimately desirable to confirm this point. It has been shown that DC incubated with the clone 3 DC binding DNA-NP secrete IL-6 (representative experiment shown in FIGS. 20A-20B). In addition, it has been measured Ca$^{2+}$ flux 20 seconds after DC are exposed to clone 3, but not after exposure to control DNA-NP.

In general, non-specific uptake or immune activation of non-targeted particles was not observed, suggesting that selection of particles with binding affinity for the target cell type is essential and that non-specific cell binding is minimal.

Hybrid Particle Formation

Figure 21:
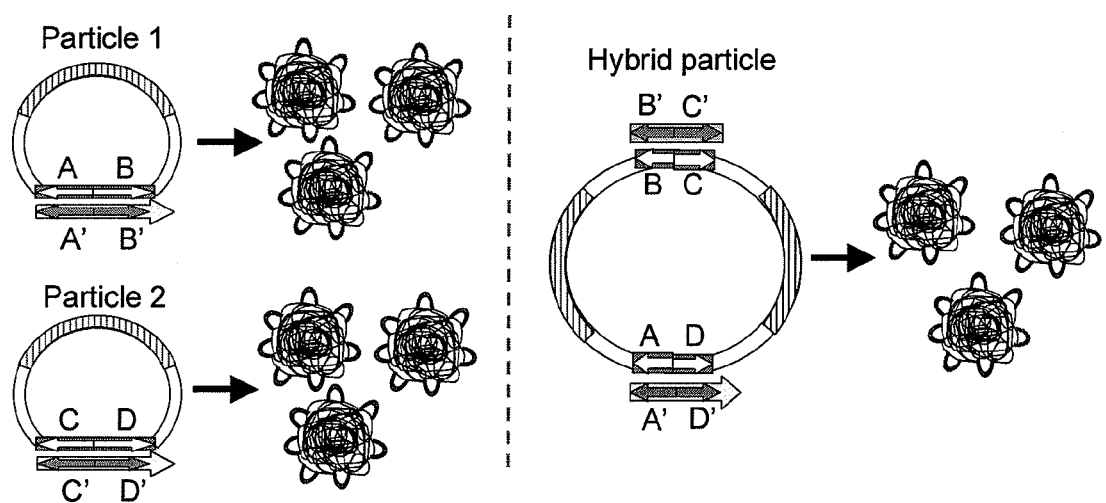
FIG. 21 relates to hybrid DNA nanoparticle formation. Templates for two particles can be fused by ligation. One ligation primer is dideoxy terminated so that it can not prime the RCA. The resulting DNA-NP contains many copies of each sequence, at a precise 1:1 ratio. If desired the ratio could be tuned by altering the number of copies of one or the other in the template construction.

A powerful feature of the DNA-NP methods includes the template sequence from which the particles are generated can be easily manipulated. One or more synthetic oligonucleotides can be used to build the template and beyond a minimum size of 60-80 bases, the RCA reaction proceeds equally well on templates regardless of size. Therefore, once discrete particle sequences are identified it is quite straightforward to prepare a hybrid template by coupling the templates at the ligation step (FIG. 21).

One concern was that hybrid DNA nanoparticle may lose the properties of the individual components. To test this, the clone 3 sequence was ligated step-wise into a continuous circle with an equal length random sequence. The progress of these step-wise reactions was verified by gel and the final products were observed to undergo RCA as previously observed with single sequence ligations. The hybrid nanoparticles still bounding DCs and a hybrid control did not. This data supports the feasibility of developing multifunctional DNA nanoparticles from either defined sequences or during the selection.

Immunostimulatory Peptide Hp91

A short immunostimulatory peptide, Hp-91, was identified that causes activation of human and mouse DCs. These peptides will be used if the DNA-NP do not have sufficient immune activating properties on their own, either in vitro or in vivo.

Figure 22:
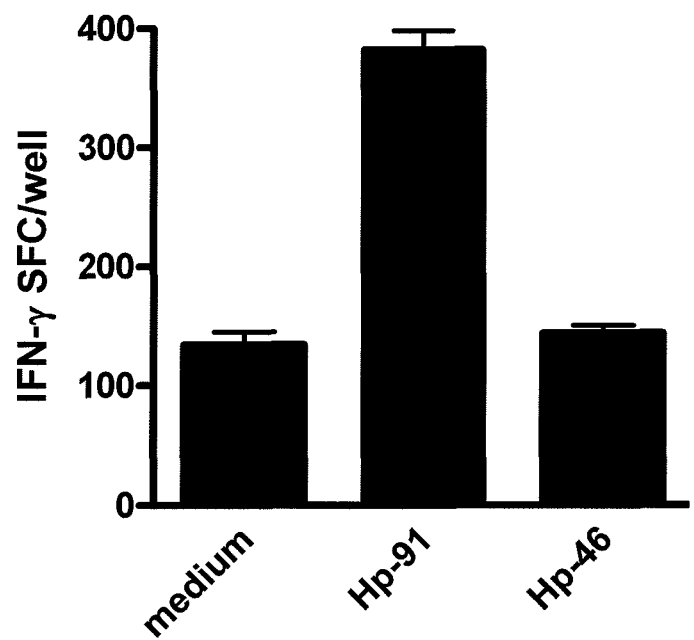
FIG. 22 provides data relating to $10^5$ immature human DCs generated from HLA.A2. Positive donors were cultured in the presence of Hp-91 or a control peptide Hp-46 (200 µg/mL), or left untreated (medium) for 48 h. DCs were washed and cultured with the melanoma peptide gp100 (500 ng/ml) and gp100-specific responder cells at a DC to responder ratio of 1:2 overnight. The number of IFN-γ secreting cells was determined 24 h later. The plate was scanned and the spots were counted automatically using the image analysis system ELISPOT reader. The data shown is the number of IFN-γ-spot-forming cells/well, are means (+/−SEM) of two independent experiments using DCs from different donors.

Hp-91 treated DCs induce antigen-specific T cells responses as measured by IFN-γ secretion in an ELISPOT assay. Hp-91 treated human DCs induced strong melanoma antigen-specific CD8$^+$ T cell responses, demonstrating the immunostimulatory capacity of the peptide Hp-91 (FIG. 22). Similar results were obtained in the mouse system, where BM-DCs pulsed with OVA-peptide and exposed to Hp-91, induced strong proliferation of OVA-specific CD8$^+$ OT-I cells.

Intra-Tumoral Injection of Hp-91 Peptide Causes Recruitment of T Cells and Dendritic Cells to the Tumor.

Figure 23:
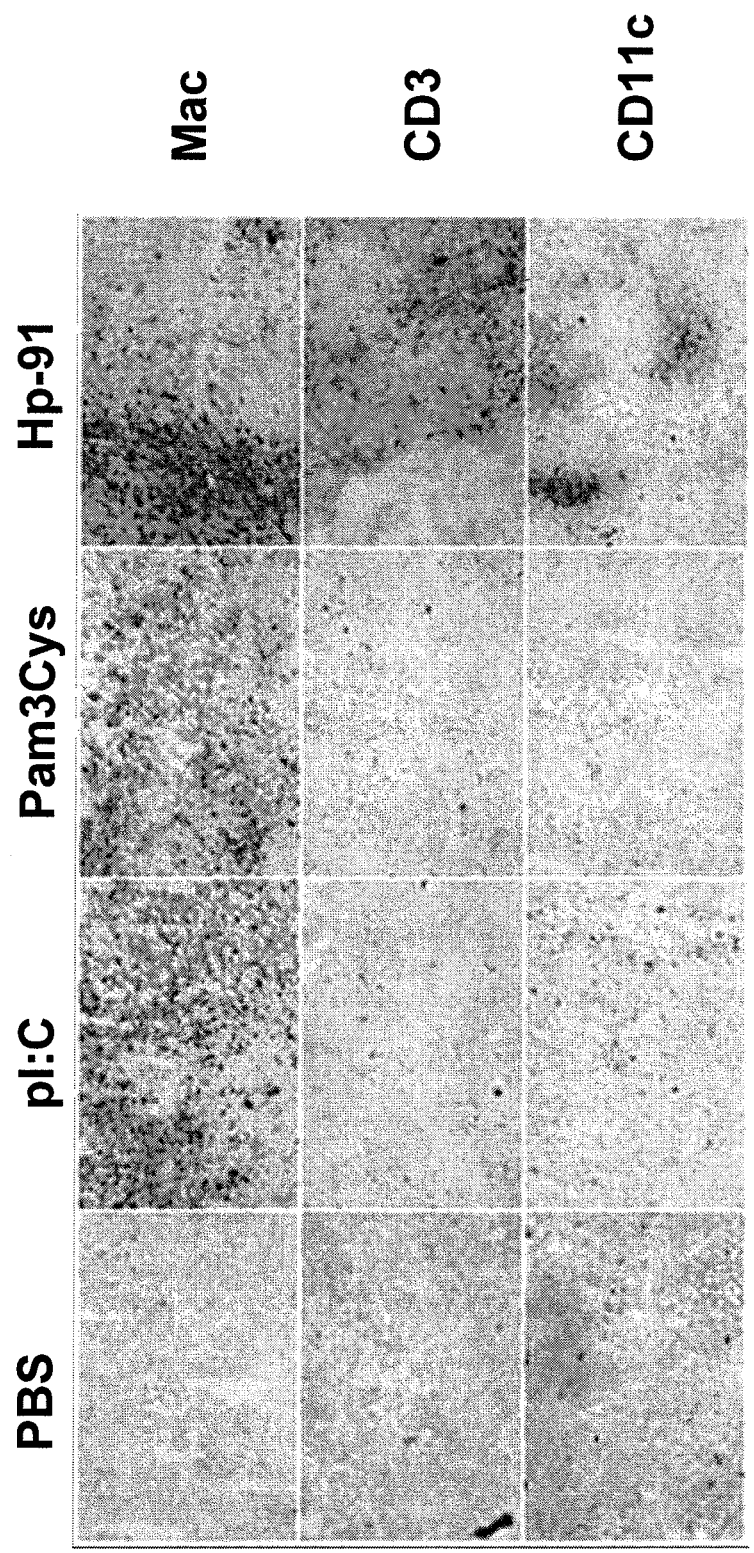
FIG. 23 provides data relating to Hp-91(270 µg), pI:C (125 µg), or Pam3Cys (125 µg) injected into B16 melanoma and the mice were sacrificed 24 h after the injection. The tumor was embedded in OCT and frozen sections were stained for Mac 1 (macrophages), CD11c (DCs), and CD3 (T cells) by immuno-histochemistry. Pictures were taken in brightfield at 20×. Higher doses of pI:C and Pam3Cys (500 µg) still showed no T cell and DC recruitment (data not shown).

The number of lymphocytes and DCs within tumor has been shown to correlate with good prognosis. In certain subsets of breast tumors the presence of tumor-associated macrophages is associated with better prognosis. Thus, in order to maximize the anti-tumor immune response we tested two TLR agonists; pI:C (TLR3 agonist) and Pam3Cys (TLR2 agonist), and our immunostimulatory peptides for their ability to recruit immune cells to the tumor. Hp-91, pI:C, or Pam3Cys were injected into B16 melanoma, the mice were sacrificed 24 h after the injection and the tumor was frozen and sections stained for the indicated markers. Although all three adjuvants caused recruitment of macrophages (MadI+) into the tumor, only Hp-91 also caused the recruitment of DCs (CD11c+) and T cells (CD3+) (FIG. 23). Further characterization using cell type specific antibodies, suggests that these are CD8+ cells. No CD4+ T cells or FoxP3+ cells (Treg) were detected (data not shown). This is a very promising result as Hp-91 will not only contribute to the recruitment of DCs, but also mature the arriving DCs. Thus in the context of antigen release by concurrent local cytotoxic therapy, we expect to create a very favorable environment for the uptake of tumor antigen by DCs and their subsequent activation. In addition, CD8 T cells after being primed in the draining lymph nodes are expected to be recruited in higher numbers to the tumor site via the peptide leading to a strong immune response and tumor killing.

Coupling of Hp91 to DNA-NP

A method to attach peptides to DNA-NP has been developed. The peptide is synthesized as a c-terminal conjugate to a 15 base oligonucleotide that is complementary to the sequence of the DNA-NP ligation or priming site. A Cy5 labeled Hp91-oligo conjugate was synthesized with a complementary sequence to clone 3. An estimation of the number of potential hybridization sites on the DNA nanoparticles was made from the total DNA quantitation. The nanoparticles were then hybridized at 37° C. for 30 minutes with increasing concentrations of the conjugate. After hybridization, the mixture was purified by low pressure size exclusion chromatography for which the elution profiles of the DNA nanoparticles and the free Cy5 labeled peptide-oligo conjugate had been previously established. At high ratios of Cy5 peptide-oligo conjugate to DNA nanoparticles, a significant fraction of the conjugate remained unhybridized as indicated by a strong peak at the free conjugate retention time. As the ratio of the labeled conjugate to the estimated hybridization sites on the DNA nanoparticles dropped, the free conjugate elution peak began to drop, eventually disappearing at a ratio of 1:2 (labeled conjugate:DNA nanoparticle sites) indicating that the DNA nanoparticles can be loaded to saturation by hybridization when 50% of their available sites are occupied.

Research Design and Methods

Some embodiments will utilize existing DC binding DNA-NP to find those that best stimulate DCs into antigen presenting cells as measured by T cell activation. If none of the existing particles are sufficient new ones can be selected by several strategies or, if that fails, combine DC binding DNA-NP with the potent peptide adjuvant Hp91. A unique feature of the technology can be exploited to make hybrid particles and determine if they offer improved performance over single sequence particles. Once the most promising candidate particle is identified it can be tested in the B16-OVA mouse melanoma model by both intra-tumoral and systemic administration, with and without the model tumor antigen. Initial studies of immune responses can direct pilot studies of anti-tumor responses, with success leading to larger, statistically powered studies.

Methods to Screen DNA-NP that Activate DC.

Five DNA-NP that bind to DC have been identified. These can be compared for their ability to activate DC. The DC stimulatory capacity of DNA-NPs can be assessed on myeloid (CD11c+) bone marrow-derived DCs (BM-DCs) in vitro, as these are known to function similarly to human monocyte-derived DCs.

DC activation and maturation is characterized by altered surface expression of characteristic molecules, production of large amounts of cytokines and enhanced T cell stimulatory capacity. Therefore, the dendritic cell stimulatory capacity of the DC-binding DNA-NPs can be evaluated in three ways: 1) their ability to alter the expression of surface molecules on immature dendritic cells that are classically up or down regulated upon maturation; 2) their ability to induce secretion of inflammatory cytokines, and finally 3) their ability to mature DCs into effective antigen presenting cells that activate naive antigen-specific T cells. The activity of the DNA-NPs can be compared to PBS (negative control) and LPS as positive control. Bone marrow DCs can be generated from primary mouse bone marrow cells depletion of other cell types and culture with GM-CSF (Inaba K, et al., (1993) Granulocytes, macrophages, and dendritic cells arise from a common major histocompatibility complex class II-negative progenitor in mouse bone marrow. Proc Natl Acad Sci USA 90: 3038-42). Each DNA-NP can be tested at final concentrations of 10 and 100 ng/ml, which corresponds to rough $10^9$ and $10^{10}$ particles per ml.

After 48 h, the CD11c$^+$CD11b$^+$B220$^-$ myeloid DCs can be analyzed for surface expression of MHC-II, CD86, CD40, and CD80 by flow cytometry. Furthermore, the cell culture supernatants can be assayed for the content of IL-12, IL-6, TNF-α, IL-8, IL-10, TGF-β and IL-1α by ELISA. To demonstrate functional maturation of DCs stimulated by the DNA-NPs, DCs can be tested for their capacity to activate antigen-specific syngeneic T cells. Bone marrow-derived DCs generated from C57BL6 mice will be stimulated with DNA-NPs, LPS (positive control) or PBS (negative control) for 24 h. The next day the DCs can be pulsed with OVA$_{257-264}$ peptides (for CD8 T cells) and OVA$_{323-336}$ (for CD4 T cells) and co-cultured with TCR transgenic OVA-specific OT-I and OT-II transgenic T cells for 38-50 h. C56BL/6 mice are chosen, because antigen presentation can be readily monitored using CD4+ and CD8+ OVA-specific OT-II and OT-I transgenic T cells. T cell activation can be assessed for a) proliferation by measuring the uptake of [$^3$H]-thymidine during the remaining 16 h of culture, and b) Th1 and Th2 cytokines by measuring IL-4, IL-2, IL-10 and IFN-γ levels of the cell culture supernatants by ELISA and intracellular IL-4, IL-2 and IFN-γ levels by flow cytometry. For intracellular staining of cytokines, the cells can be incubated with brefeldin A to prevent leakage of the cytokines before permeabilization.

Particle Ranking and Hybrids

The particles can be ranked according to their activity in the assays herein. Since T cell stimulation is the ultimate goal, significant weight can be given to those results, followed by up-regulation of co-stimulatory molecules. However, any particle that shows activity in any of the assays can be included in the hybrid particle matrix herein.

As described herein, methods for producing DNA-NP with two or more discrete sequence components are provided. Individual DC binding particles that show activity can be combined to further enhance their potency. The counter hypothesis would be that the particles all function via the same mechanism and that there will be no advantage to combining them. Hybrids pairs can be produced from all sequences that produced positive results above. If all five of the particles tested show activity, that would require 10 unique hybrids. These can be assayed and ranked as described above. These experiments can be the most interesting if different particles show a different spectrum of activation (ie. cytokine secretion but not phenotypic maturation, T cell stimulation in the absence of cytokines). However, if none of the hybrids shown superior activity to the composite monomers then only the monomers may be used.

Mechanism

Mechanistic studies are performed to address whether: 1) endocytosis is required for the DNA-NP activity, and 2) the DNA-NP activity occurs with TLR/MyD88. The first question is addressed using a panel of endocytosis inhibitors concurrent with DNA-NP, using cytokine secretion and phenotypic maturation as readouts. The inhibitors are brefeldin A and colchicine, both of which interfere with vesicle trafficking, filipin, which is known to inhibit caveolae-mediated endocytosis by binding to cholesterol and disrupting caveolae structure and function, and sucrose, which generates hyper-osmolarity that blocks membrane internalization and clathrin recycling via the coated-pit pathway. Confocal microscopy confirms the intracellular localization of the DNA-NP.

The potential role of TLR signaling is addressed by using DC from TLR 3,4,7, and 9 as well as MyD88 knockout mice. An hypothesis is that the DNA-NP bind to the surface of the DC by some DC specific protein or glycoprotein and are then internalized by endocytosis. While in the endosome they signal through TLR9 and, downstream, MyD88. However, it is possible that DC activation occurs by other mechanisms and the initial binding event could trigger MyD88 independent pathways. The rapid calcium flux would be consistent with this model. These experiments provide a basic working model for the DNA-NP activity.

In vitro Selection Against Mouse DC

A pool of DC binding particles were selected against human DC. While at least one clone also binds to mouse DC, activation of mouse DC was not confirmed. Bone marrow-derived DCs are generated from C57BL/6 mice. These bone marrow-derived DCs are generated in the presence of GM-CSF and yield only myeloid not plasmacytoid DCs (PDCs), since GM-CSF prevents the development of PDCs. Further purification are achieved by positively selecting CD11c+ cells from the day 6-8 cultured using magnetic beads. If non-specific cell binders are recovered, an adherent mouse fibroblast cell line is used for counter selection. The adherent cells absorb non-specific cell binders and are removed from the non-adherent DCs.

In vivo Selection

In vivo selection of targeting ligands has been well established with phage displayed peptide libraries. While seemingly a complicated and potentially difficult proposition, in vivo selections have two significant advantages. The first is that the selection is being performed in the very same environment that the ultimate product will be used. The second is that the rest of the animal acts as a subtractive substrate that will remove any non-specific particles. We will perform in vivo selections by injecting the DNA particle library subcutaneously and recovering the draining lymph nodes several hours later. The lymph nodes will be treated with collagenase to create single cell suspensions, and the MHC-class II+ antigen presenting cells (including DCs and B cells) will be isolated by magnetic bead separation. Subsequently the particle recovery, re-amplification, and ligation is as described herein.

Combinatorial Library Screening

Figure 24:
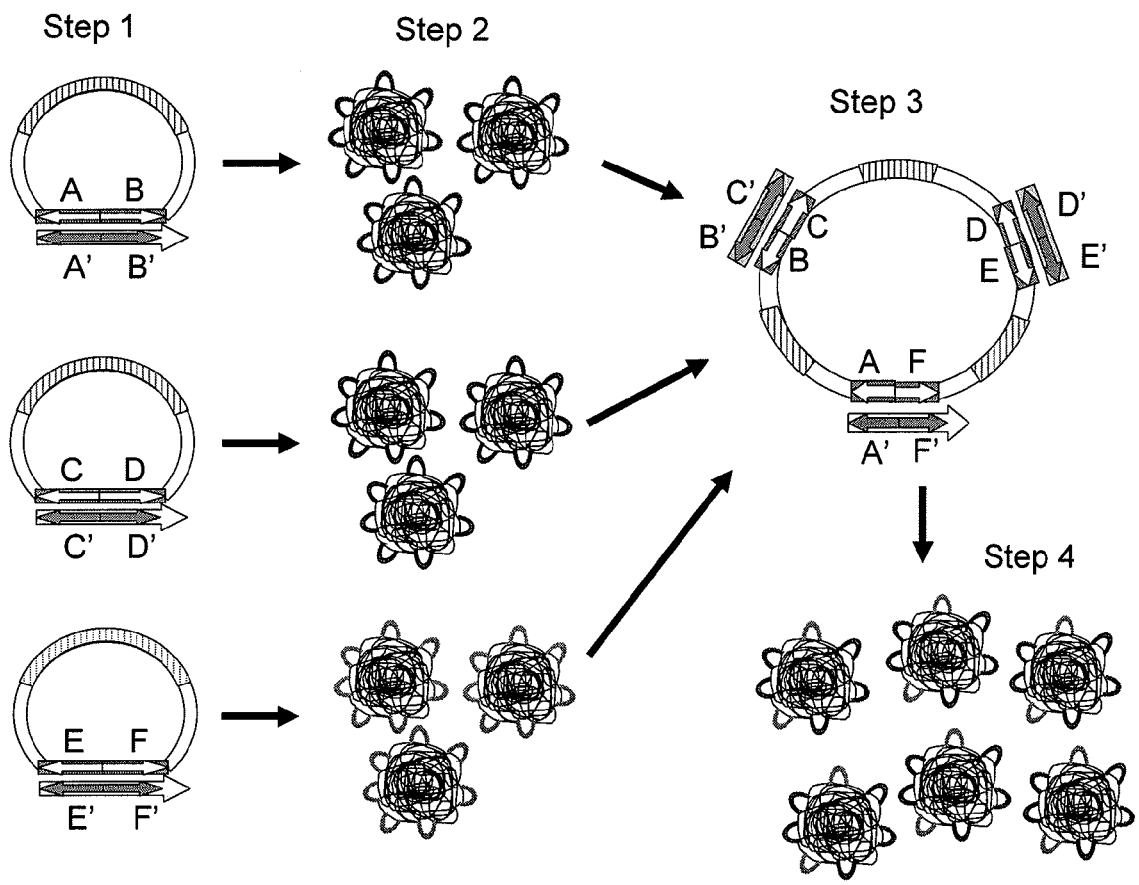
FIG. 24 relates to embodiments that include a strategy for selection and combinatorial breeding of multimeric polyvalent DNA nanoparticles. Step 1. Several libraries with unique ligation and PCR primers are generated. Step 2. Each library is independently screened for a few rounds against the target to create an initial enriched pool. Step 3. The products of the initial screenings are combinatorially assembled into multimeric templates and polyvalent DNA particles are generated. Step 4. The particles are subjected to subtractive screening to enrich the desired binding activity and eliminate unwanted crossreactivities as described herein. In each selection step the individual library components are re-assorted, creating additional combinatorial diversity from which optimal particles can be selected.

FIG. 24 shows a strategy for selection and combinatorial breeding of multimeric polyvalent DNA nanoparticles. Step 1. Several libraries with unique ligation and PCR primers are generated. Step 2. Each library is independently screened for a few rounds against the target to create an initial enriched pool. Step 3. The products of the initial screenings are combinatorially assembled into multimeric templates and polyvalent DNA particles are generated. Step 4. The particles are subjected to subtractive screening to enrich the desired binding activity and eliminate unwanted cross-reactivities as described herein. In each selection step the individual library components are re-assorted, creating additional combinatorial diversity from which optimal particles can be selected.

The hybrid particle concept can be introduced at the library screening step. The specificity of particles for cancer cells can be improved if more than one ligand is targeted, creating an "AND" type function for binding. This can be implemented by performing several selections against a given target cell population using libraries with different circularization and PCR primer sequences. The products of each selection can be combinatorially assembled by creating particles that consist of one unit from each library. In this way particles can be "bred" that optimize selectivity and exploit the potential that each DNA unit might recognize a distinct component of the target cell. In each round, the three component pieces are re-assorted so that the optimal combination enrich over several rounds of selection.

Candidate Particle Cloning and Binding to Target Cells

After a successful selection, candidate particles are further analyzed from the final pool. To obtain individual particles, the final pool are amplified by Stoffel PCR and cloned into a plasmid sequencing vector. Once cloned, 10-20 candidates are sequenced to determine the extent of sequence diversity in the final pool. Each candidate can be re-generated by PCR/asymmetric PCR amplification from the plasmid. The candidate particles from a selection are tested individually for target cell binding by making fluorescently tagged particles. The labeled clones are incubated with lymph node suspension cells on ice for 1 h and co-stained with antibodies against B220 (B cells), CD11c (myeloid DCs), and PDCA-1 (plasmacytoid DCs) to identify the bound target cells and demonstrate specificity. Labeled cells are analyzed cell binding by flow cytometry and fluorescent microscopy.

Addition of Immunostimulatory Peptide Hp91

If no particle is obtained with the ability to activate DC, the DC binding DNA-NP is used as a carrier for peptide Hp91 as described in the preliminary data. It is determine if the DNA-NP/Hp91 formulation retains or improves the activity of the DC stimulatory activity of the peptide. Even if there is not an improvement with the DNA-NP in the in vitro assays, in vivo experiments are performed as it is possible that the DNA-NP targeting could be far more relevant in the in vivo.

Methods to Test the Hypothesis that Direct Injection of DNA-NP into Tumors Activate Tumor Infiltrating DC Tumor Model All in vivo experiments are conducted in a transplantable mouse model of melanoma using the mouse melanoma cell line B16-OVA that expresses chicken ovalbumin, which serves as a tumor marker to monitor immune responses. When injected s.c. into C57/BL6 mice, B16-OVA produces a local tumor growth. The experiments are hierarchically designed to reveal that 1) the DC binding DNA-NP can perform that function in vivo, 2) that immune activation via DNA-NP within the tumor can awaken a tumor specific immune response, and 3) that immune response will lead to tumor rejection.

C57/BL6 mice (n=5 per group) are inoculated with $5\times10^5$ B16 cells s.c. Once the tumors reach 3-5 mm in size they receive intra-tumoral injection of: 50 µl of PBS, DC binding DNA-NP, or a control DNA-NP. DNA-NPs is injected at 1 and 10 ug/ml (~$10^{10}$ and $10^{11}$ particles) suspended in PBS. 24 hours later the mice are sacrificed and the tumor, draining lymph nodes, blood, liver, and spleen are collected.

Histology is performed on the tumor and the number of infiltrating lymphocytes compared (CD3+ and CD11c+) to controls. Single cell suspensions are made by treating the tissue with collagenase and the expression of IL-12, IFNγ, TNF alpha, and RANTES by sorted CD11c+ cells determined by RT-PCR. The particle characteristics are optimized.

Nanoparticle Optimization

The size of the DNA nanoparticles can be tuned by the RCA reaction time (see data herein). The DNA-NP are synthesized under reaction conditions that produce a mean size of 100, 200, and 300 nm as measured by dynamic light scattering. Aliquots are reserved for confirmation by WETSEM (see data herein for example image). The different size batches are equalized for total particle number and compared as described herein. The optimal size thus determined is used for all other experiments.

In addition, the nuclease sensitivity can be manipulated in several ways. The particles are inherently resistant to exonucleases since they are a continuous single strand with only one 5' and one 3' end. Furthermore, these ends can be made exonuclease resistant. The 5' end is created by the ligation primer and can therefore be made with an altered base (e.g. phosphorothioate) at the time of oligonucleotide synthesis. The 3' end can be made resistant by adding a modified dideoxy nucleotide triphosphate at the end of the RCA reaction, such that the growing strands are terminated by an exo resistant base. The particles are insensitive to endonuclease because of their primarily single stranded character. However, endonuclease resistance can be increased by the incorporation of phosphorothioate nucleotides during the RCA reaction. Furthermore, degradation independently increases activity of CpG oligonucleotides containing phosphorothioate backbones. Particles are synthesized that contain entirely a phosphorothioate backbone and are compared as described herein.

Tumor Regression Studies

A long term tumor monitoring study is performed. Groups of mice (n=5) are inoculated with tumor and injected with DNA-NP or controls as described herein. 7-14 days after the initial injection mice receive a second injection identical to the primary one. The mice are observed bi-weekly and the primary tumor size measured using a set of calipers: $AxB^2/2$ (A=long axis, B=short axis) over a period of 20 days. After 20 days or if the tumors reach 1.5 cm in diameter, whichever occurs first, mice are sacrificed. At time of euthanasia mice are monitored for potential pathological effects. The spleen and kidney are weighed and tissue analysis is performed.

Methods to Test the Hypotheses that Immunization with DNA-NP and Model Tumor Antigens Elicit Antigen Specific Responses and Tumor Rejection Co-injection of the most potent DNA-NPs identified herein with antigen can lead to the induction of an immune response. The potency of DNA-NPs as vaccine adjuvants is compared to alum to measure the quality as well as quantity of the immune response by using the same route of immunization. Ovalbumin (OVA) and influenza haemagglutinin (HA) have been suggested to study the adjuvanticity of new formulations. Since aluminum compounds do not exhibit an adjuvant effect when used with HA, whole OVA protein are used as antigen, to establish the adjuvanticity of the DNA-NP.

The adjuvanticity of the DNA-NPs is assessed and compared to aluminum hydroxide. Groups of C57BL/6 mice (n=10) receive s.c. injections of OVA/PBS (as negative control), OVA/aluminum hydroxide (Alhydrogel™, aluminum hydroxide, from Superfos Biosector, Vedbaek, Denmark) (positive control), or OVA/CpG (positive control), and 3 different doses of OVA/DNA-NPs (1-100 µg/mouse), that show DC activation in preliminary studies. Optimal formulations of antigen adsorbed to aluminum adjuvant are prepared to correctly evaluate new adjuvants. To minimize variation and to avoid non-reproducibility due to different preparations of aluminum components, a specific preparation of Alhydrogel™, aluminum hydroxide, from Superfos Biosector, Vedbaek, Denmark, are used. The complete absorption of the antigen on aluminum adjuvant is verified by measuring antigen/protein levels before and after adsorption in the supernatants. The conditions are optimized to reach the WHO recommended adsorption of 80%. Two to three weeks after immunization the animals receive a second "booster" immunization performed exactly as the first injections. Blood is obtained from mice at three time points: before immunization for base antibody levels, before the booster immunization and 1-2 weeks after the second "booster" immunization. Plasma IgG and IgM levels specific for the injected antigen are measured by direct ELISA using plates coated with antigen. The antibody results are determined in arbitrary units against an ELISA reference serum in order to reliable compare results obtained on different days. The type of immune response is further characterized by measuring the subclass antibody concentrations. In mouse, the production of IgG2a is recognized as characteristic of a Th1 response, whereas the production of IgG1 is characteristic of a Th2 response. Therefore, the assessment of the type of immune response is performed by measuring IgG1, IgG2a and IgG2b levels by ELISA. The ratio of IgG2a/IgG1 antibody titers is used as indicator of Th bias. A Th2 response is also characterized by the secretion of Th2 type cytokines, such as IL-4, IL-5, whereas a Th1 type response is characterized by the secretion of IL-2 and IFN-γ.

The in vivo induced T cell responses is detected in vitro using a variety of assays. 1) Proliferation assays are performed by adding $OVA_{257\text{-}264}$ peptides (to stimulate CD8 T cells) and $OVA_{323\text{-}339}$ (to stimulate CD4 T cells), PBS/no peptide (negative control) or ConA (positive control) to un-separated lymph-node cells from the draining lymph node, which contain T cells and antigen presenting cells, and measuring the uptake of $[^3H]$-thymidine after 4 d. To measure T cell responses, un-separated lymph-node cell cultures are set up as described herein, but the positive control will be phorbal myristate acetate (PMA) and soluble anti-CD3, since ConA is not a potent stimulus for Th2 cytokines. After 24 h the culture supernatants are assessed for IL-4, IL-2, IL-5, IL-10, TGF-β and IFN-γ levels by ELISA. IFN-γ ELISPOT and intracellular flow cytometry assays for IL-4, IL-2 and IFN-γ are used to measure the number of cytokine secreting T cells and double labeling for CD4 and CD8 to detect the type of T cells responding. For intracellular staining of cytokines, the cells are incubated with brefeldin A to prevent leakage of the cytokines.

Tumor Rejection Studies

C57/BL6 mice are inoculated with $5\times10^5$ B16 cells s.c. Once the tumors reach 3 mm in size, groups of mice (n=20) receive s.c. immunizations of Ovalbumin mixed with: PBS, or 10 µg DNA-NPs. 7-14 days after the initial injection mice receive a second injection identical to the primary one. Half the mice from each group (n=10) are sacrificed to analyze immune responses and the other half are monitored for tumor progression.

Ten days after the final immunization, half the mice from each group are sacrificed and tumor draining lymph nodes and spleens are harvested. Unfractionated lymph node cells and splenocytes are cultured in medium only and re-stimulated with mitomycin C-treated (50 µg/ml) B16-OVA cells. B16-OVA cells are exposed to mitomycin C for 20 min, washed and co-cultured with lymph node cells. As a positive control lymph node cells and splenocytes are stimulated with Concanavalin A (5 µg/ml). After 16-40 h the cell culture supernatants are assessed for IL-2, IL-4, IL-5, IL-10, TGF-β and IFN-γ levels by multiplex-luminex assay or ELISA. IFN-γ ELISPOT is used to measure the number of cytokine secreting T cells. To further investigate the contribution of CD8+ and CD4+ T cells to the cytokine secretion, each cell type is depleted from the splenocytes separately using specific antibodies prior to in vitro culture. To measure the generation of functional CTL responses, unfractionated lymph node cells and splenocytes are re-stimulated in vitro with the mitomycin C-treated (50 µg/ml) B16-OVA cells. The cells are expanded in 24-well plates for 6 days at a concentration of $3\times10^6$ cells in 1.0 mL of medium with the addition of recombinant mouse IL-2 (50 U/ml) after 24 h of culture. Cytolytic activity is assessed at day 6 by culturing expanded lymph node cells and splenocytes with B16-OVA target cells and B16 (=negative control target cells), using a standard 4 h LDH assay. The absorbance values from supernatants are recorded at OD 490 nm. The percent of specific lysis is calculated as follows: $(D_{Exp.}-OD_{spon.E}-OD_{Spon.T}/OD_{max.T}-OD_{spon.T})\times 100$, where $OD_{Exp}$ is the OD related to the experimental LDH relase, $OD_{spon.E}$ is the OD related to the spontaneous release of LDH from the effector cells only, $OD_{spon.T}$ is the OD related to the spontaneous LDH release from target cells only, and $OD_{MaxT}$ is the OD related to the maximum LDH release from target cells using lysis buffer.

The other half of mice from each group (n=5) are observed bi-weekly and the primary tumor size is measured using a set of calipers: A×B²/2 (A=long axis, B=short axis) over a period of 20 days. After 20 days or if the tumors reach 1.5 cm in diameter, whichever occurs first, mice are sacrificed. At time of euthanasia mice will also be monitored for potential pathological effects see below. The spleen and kidney will be weighed and tissue analysis will be performed by our molecular pathology core.

If there is a low frequency of melanoma-specific T cells a second round of in vitro activation of the lymph node cells might be necessary. Cells are cultured for 12-16 days with periodic re-stimulation of the cultures with tumor-lysate pulsed irradiated syngeneic BM-DCs. After 2-3 rounds of re-stimulation, the lymph node cells are mixed with target cells and assayed for their killing capacity as described herein. If no specific lysis of target cells is observed in the LDH assay, target cells are pre-treated with 20 ng/ml IFN-γ 24 hours prior to use in cytotoxicity assays, which is known to increase the HLA expression. HLA molecules are monitored by FACS.

Pharmacodynamics and Toxicity of DNA-NPs in vivo.

The immunization experiments provide an opportunity to gain insight into the in vivo distribution and half life of the DNA NPs, as well as any associated toxicity. Organs and blood are recovered from the sacrificed animals and tissue extracts prepared. An attractive feature of the DNA-NP is that they can be very sensitively and precisely quantified by real time PCR. rtPCR is used to surmise the biodistribution and circulating levels of the particles. DNA-NP were injected into mice intravenously and no ill effects were observed.

Groups of mice receive DNA-NPs, that show activity in the tumor model described herein, in 3 different doses s.c. (1-100 μg/mouse). All mice are monitored daily for necrotic areas at the site of injection and for signs of distress and death over the course of all experiment. Any mice that die or are euthanized due to distress or discomfort is evaluated. Furthermore, serum is assayed for anti-nuclear antibodies by standard immunofluorescence approaches, for anti-DNA antibodies by *L. crithidia* assays, and for rheumatoid factor and anti-HMGB1 antibodies by ELISA once every two weeks until 2-3 months after the injection of adjuvant. At time of euthanasia mice are also be monitored for potential pathological effects. The spleen and kidney will be weighed and tissue analysis will be performed.

It is possible that high levels of DNA-NPs could potentially cause side effects, such as local tissue necrosis or lead to the induction of anti-DNA antibodies. If tissue necrosis occurs it will likely be mild and transient, since the DNA-NPs are not administered chronically. If side effects occur, lower doses are tested.

Concurrent Cytotoxic Therapy

An hypothesis for antigen agnostic approach is that DNA-NP will stimulate the tumor infiltrating DC which will, in turn, awaken tumor specific CTLs. However, other immunotherapy studies in this system s have shown improved results when combined with cytotoxic therapy. If the DNA-NP alone do not induce tumor regression, experiments are repeated with concurrent treatment using 5-azacytidine (5-aza). 5-aza is given i.p. at a dose of 0.2 mg/kg for three cycles, each cycle consisting of a daily i.p. injection for 5 consecutive days followed by 2 days rest.

EXAMPLES

Example 1

Generation of Nanoparticles

Figure 25:
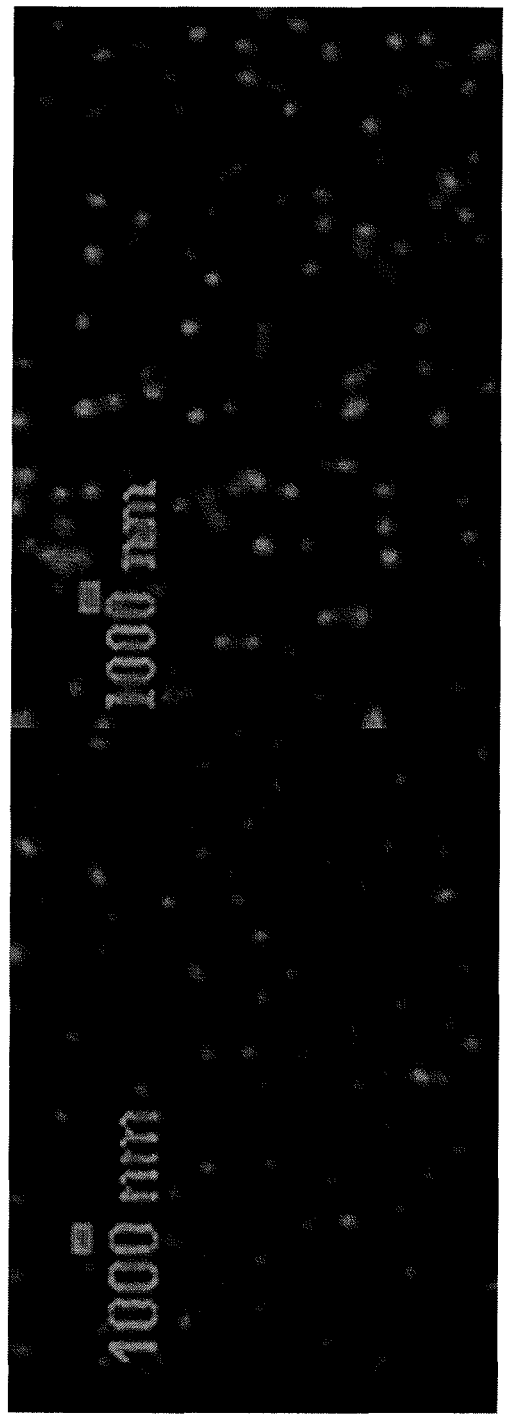
FIG. 25 shows a photograph of DNA nanoparticles made with reaction times of 5 and 30 minutes, respectively.
Figure 26:
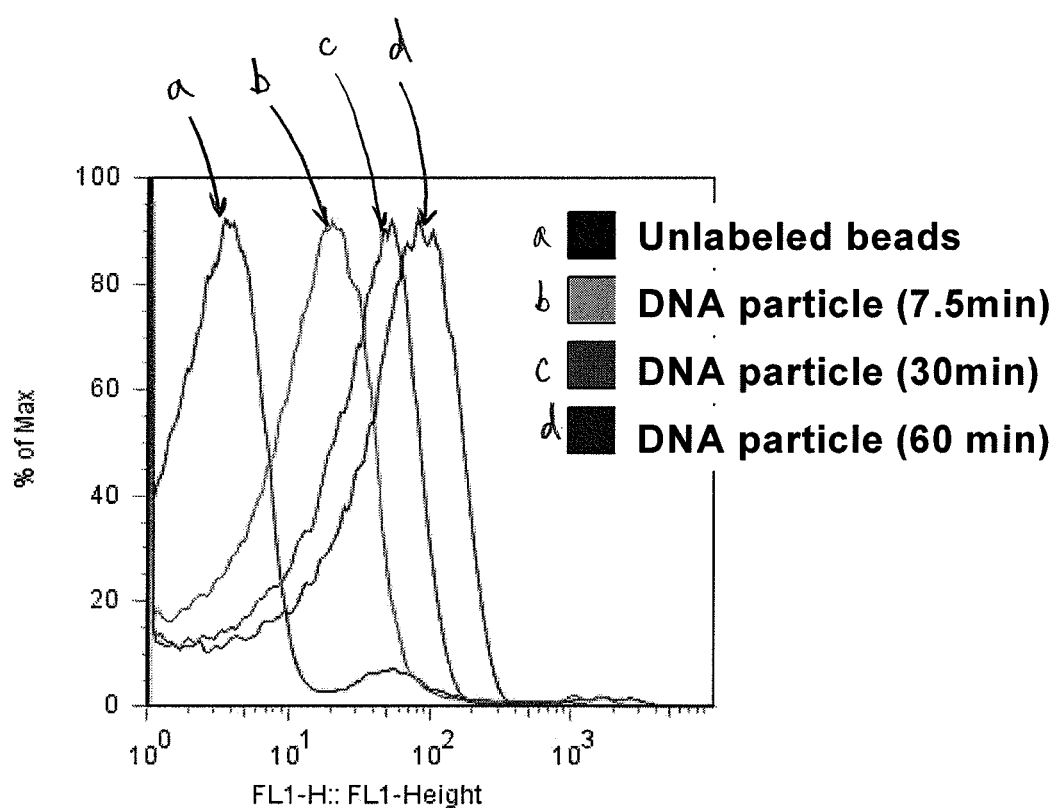
FIG. 26 shows flow cytometry data illustrating increasing fluorescence with increasing reaction time indicating larger particles.
Figure 27:
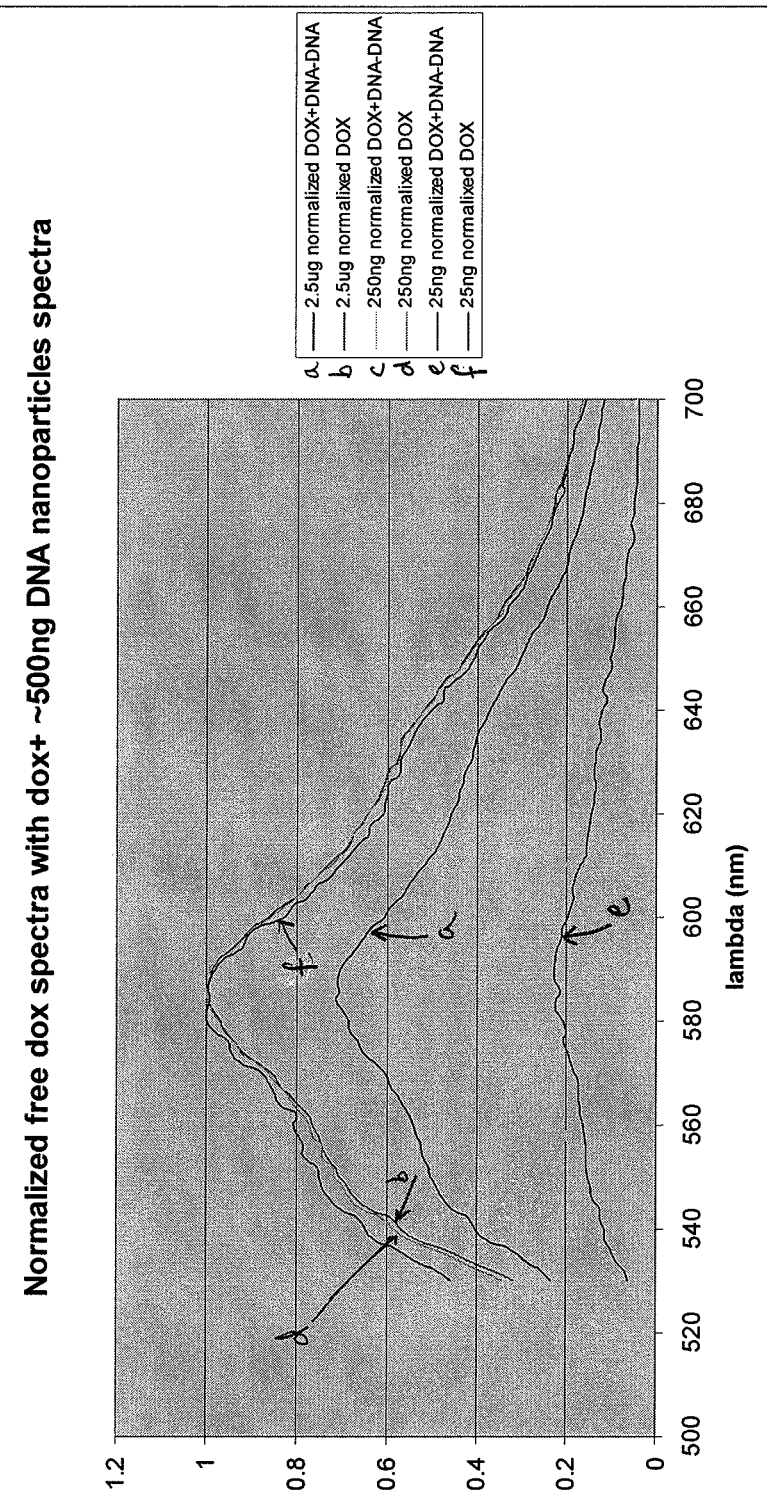
FIG. 27 shows a spectrograph of Doxorubicin and Doxorubicin with DNA nanoparticles. Doxorubicin is titrated into ~500 ng DNA nanoparticles and the fluorescence is quenched as binds. At low Doxorubicin concentrations nearly all fluorescence is quenched. With increasing concentration of Doxorubicin, the DNA nanoparticles become saturated and free Doxorubicin in solution can fluoresce.

This example demonstrates the characterization of the DNA nanoparticles. Nanoparticles were created through RCA with a variety of different encoding sequences. Nanoparticles were made into discreet particles as imaged by microscopy (FIG. 25) and were made in varying sizes as determined by DNA binding dyes in a flow cytometry setting (FIG. 26). Discreet DNA nanoparticles were made with modified fluorescent nucleotides as an internal labeling method with little to no background. In addition, the DNA binding drug Doxorubicin was loaded on the DNA nanoparticles (FIG. 27).

Example 2

Generation of Aptamer Particle Libraries

Figure 28:
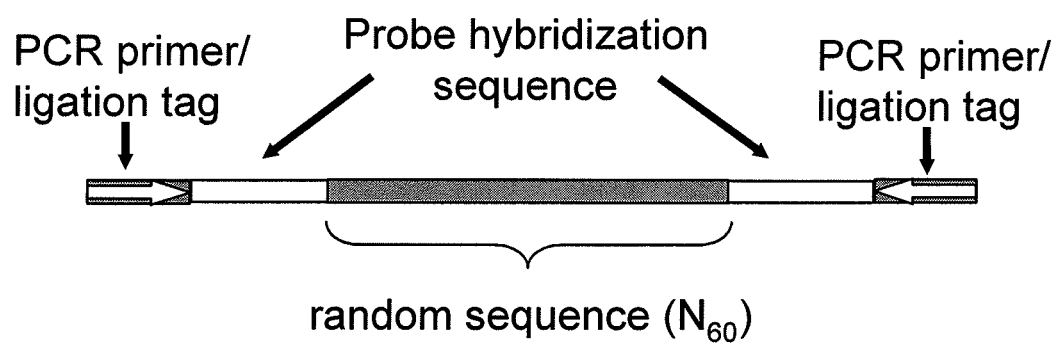
FIG. 28 shows a schematic diagram of an example library template oligonucleotide.

Multivalent aptamer containing particles will be generated from circular oligonucleotide templates by rolling circle amplification. FIG. 28 shows the library template oligonucleotide design. The ends contain PCR primer binding sites for the amplification of the library during rounds of selection. These ends also bind to the ligation template oligonucleotide to circularize the template for RCA amplification. The random sequence is 60 nucleotides long and is flanked by defined sequences that can be used to hybridize fluorescent or otherwise labeled probes for visualization or purification.

The generative library oligonucleotide templates will be circularized by annealing to a complementary ligation target. That target oligonucleotide will also serve as the primer to initiate rolling circle amplification (RCA) by phi29 polymerase. RCA produces a single stranded concatemer that is the complement of the library template oligonucleotide (FIG. 29A). The number of repeats contained in a given strand is a function of the size of the template and the amount of time the RCA reaction is allowed to proceed. Initially, 30 minute to one hour reactions will be used to produce strands containing several hundred repeats. These strands collapse into random coiled balls that are 100-1000 nm in diameter. Each particle should have many copies of the aptamer on or near the surface of the particle, enabling multivalent interactions with targets.

Example 3

Screening Aptamer Particle Libraries

The particle library will be panned against touch preparations of breast tissue containing both normal and malignant cells. Slides used will be selected as those with small numbers of clearly identifiable tumor cells in a background of many normal cells. The normal cells will serve to sponge away aptamer particles that bind to targets found on both normal and tumor cells. Tumor specific aptamer particles will be recovered by either positive or negative selection using a laser capture microscopy (FIG. 29B).

Example 4

Amplification and Regeneration of Aptamers

Aptamers bound to the target cells will be amplified by real time PCR. The amplified aptamers will then subjected to several rounds of asymmetric PCR to enrich for the template strand. The templates will be re-circularized using the ligation template from above and RCA used to generate particles as originally done (FIG. 29C). Multiple rounds of panning will be performed. The real time PCR amplification will give a rough quantitative estimate of the number of bound particles in each round. Successful enrichments will be indicated by a substantial increase in the number of bound particles (for example, 100-1000 fold).

Once a pool of aptamers has been enriched against the breast tumor cells, individual aptamer sequences will be determined by cloning the final amplified products into a plasmid vector and sequencing. Clonal populations of aptamer particles derived from individual aptamers can be recreated from these clones by the same PCR/asymmetric PCR approach used in the screening rounds.

The aptamer particles can be readily labeled either with DNA binding fluorescent dyes (for example, Sybr gold, or oligreen) or by hybridization of a fluorescently labeled oligonucleotide probe. The clonal populations will be tested for specific binding to breast tumor cells by fluorescent in situ histochemistry. Individual aptamer particles stained with a DNA dye such as Oligreen, are sufficiently bright to be detected by a flow cytometer.

Example 5

Development of Multimeric Polyvalent Aptamer Particles

Figure 30:
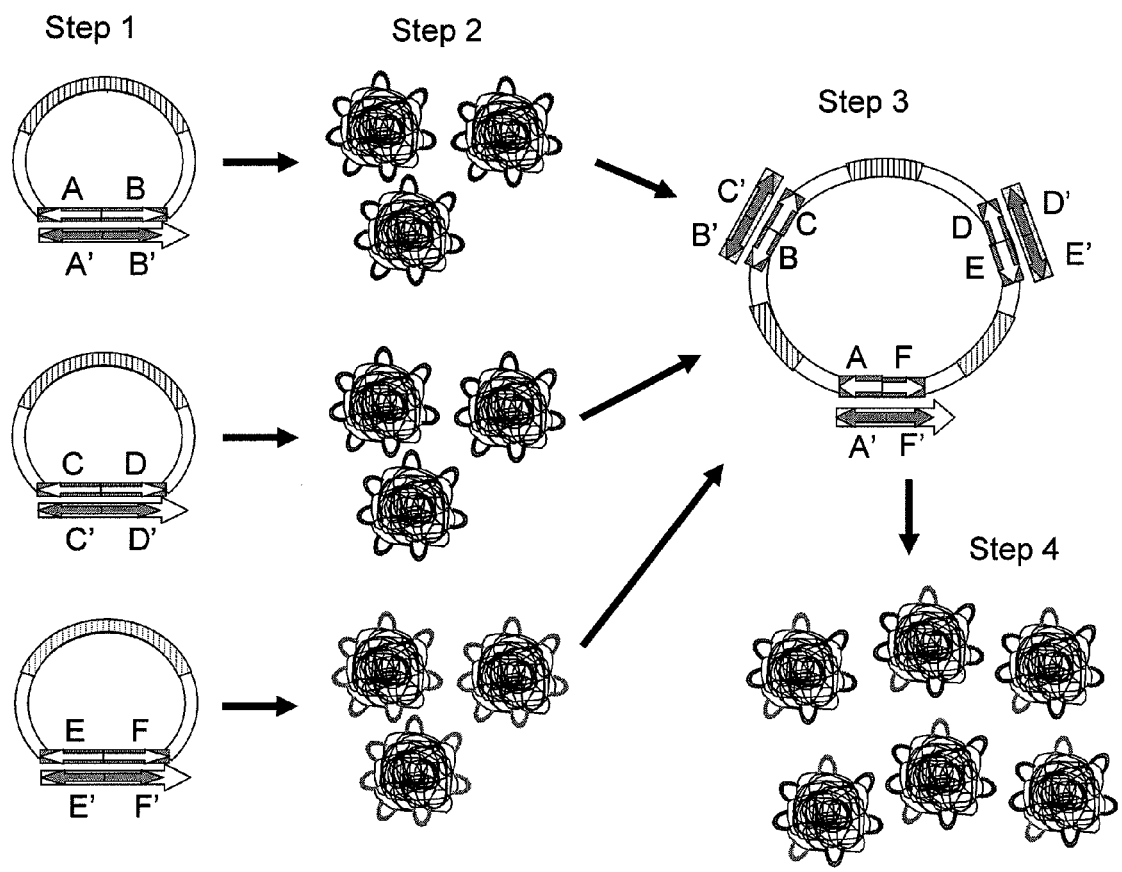
FIG. 30 shows a schematic for an example strategy for selection and combinatorial breeding of multimeric polyvalent aptamer particles. Step1 shows several aptamer libraries with unique ligation and PCR primers are generated. Step 2 shows each library is independently screened for several rounds against the target. Step 3 shows the products of the initial screenings are combinatorially assembled into multimeric templates and polyvalent DNA particles are generated. Step 4 shows the particles are subjected to subtractive screening to enrich the desired binding activity and eliminate unwanted cross-reactivities.

The modular nature of the DNA particles allows for multiple discrete aptamer sequences to be displayed on a given particle. The specificity of particles for cancer cells should be improved if more than one ligand is targeted, creating an "AND" type function for binding. This will be implemented by performing several selections against a given target cell population using libraries with different circularization and PCR primer sequences (FIG. 30). The products of each selection can then be combinatorially assembled by creating particles that consist of one unit from each library. In this way we can "breed" particles that optimize selectivity and exploit the potential that each aptamer unit might recognize a distinct library. In each round, the three component pieces will be resorted so that the optimal combination will enrich over several rounds of selection.

Example 6

DNA Nanoparticle Libraries for Imaging and Therapeutic Applications

Rolling Circle Amplification (RCA) of a circular DNA template produces a continuous single stranded complementary concatemeric nanoparticle. These particles may have applications in biological sensing, detection, and therapeutics. RCA reactions were monitored in realtime and the relationship between reaction times and conditions and particle size determined by dynamic light scattering and gel electrophoresis. DNA binding fluorescent dyes were used to visual the particles in flow cytometry and fluorescent microscopy. A purification strategy based on size exclusion chromatography was developed. The nuclease sensitivity profiles of the particles were determined for both endo and exo nucleases: these could be attenuated by the incorporation of phosphorothioate nucleotides during the RCA reaction or by modifying the 5' or 3' bases of the strand. The stability of the particles in human serum and plasma was evaluated and the interactions with serum proteins was profiled. These experiments lay the foundation for further development of DNA nanoparticles for biomedical applications.

Example 7

Production & Characterization of DNA Particles

Incorporation of Phosphorothioate Nucleotides

Figure 31:
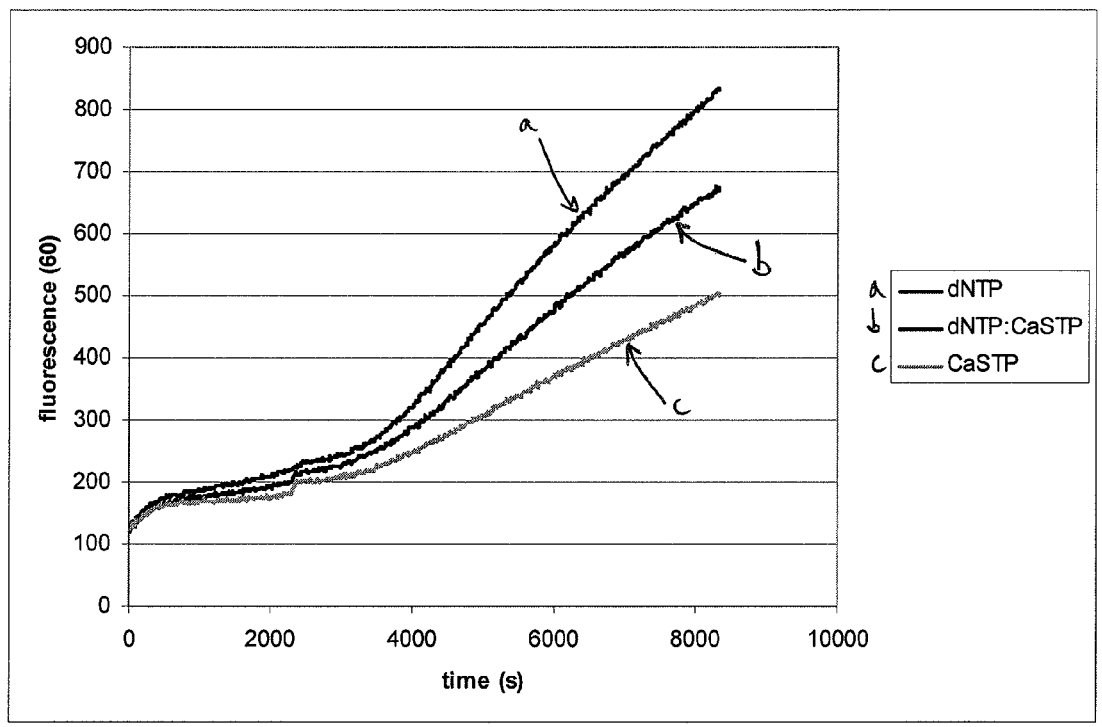
FIG. 31 shows a graph of fluorescence over time. RCA reactions were run using either dNTPs, a mixture of dNTP and phosphorothioate backbone cytosine nucleotides (CαSTP) at a 1:1 ratio with dCTP, or with a nucleotide cocktail where all dCTP was replaced with CαSTP.

RCA reactions were run using either dNTPs, a mixture of dNTP and phosphorothioate backbone cytosine nucleotides (CaSTP) at a 1:1 ratio with dCTP, or with a nucleotide cocktail where all dCTP was replaced with CaSTP. The results indicate that the phi29 DNA polymerase can incorporate CaSTP in place of dCTP during the RCA process, albeit with some loss of efficiency (FIG. 31).

Method to Purify the Particles by Size Exclusion Chromatography

Figure 32:
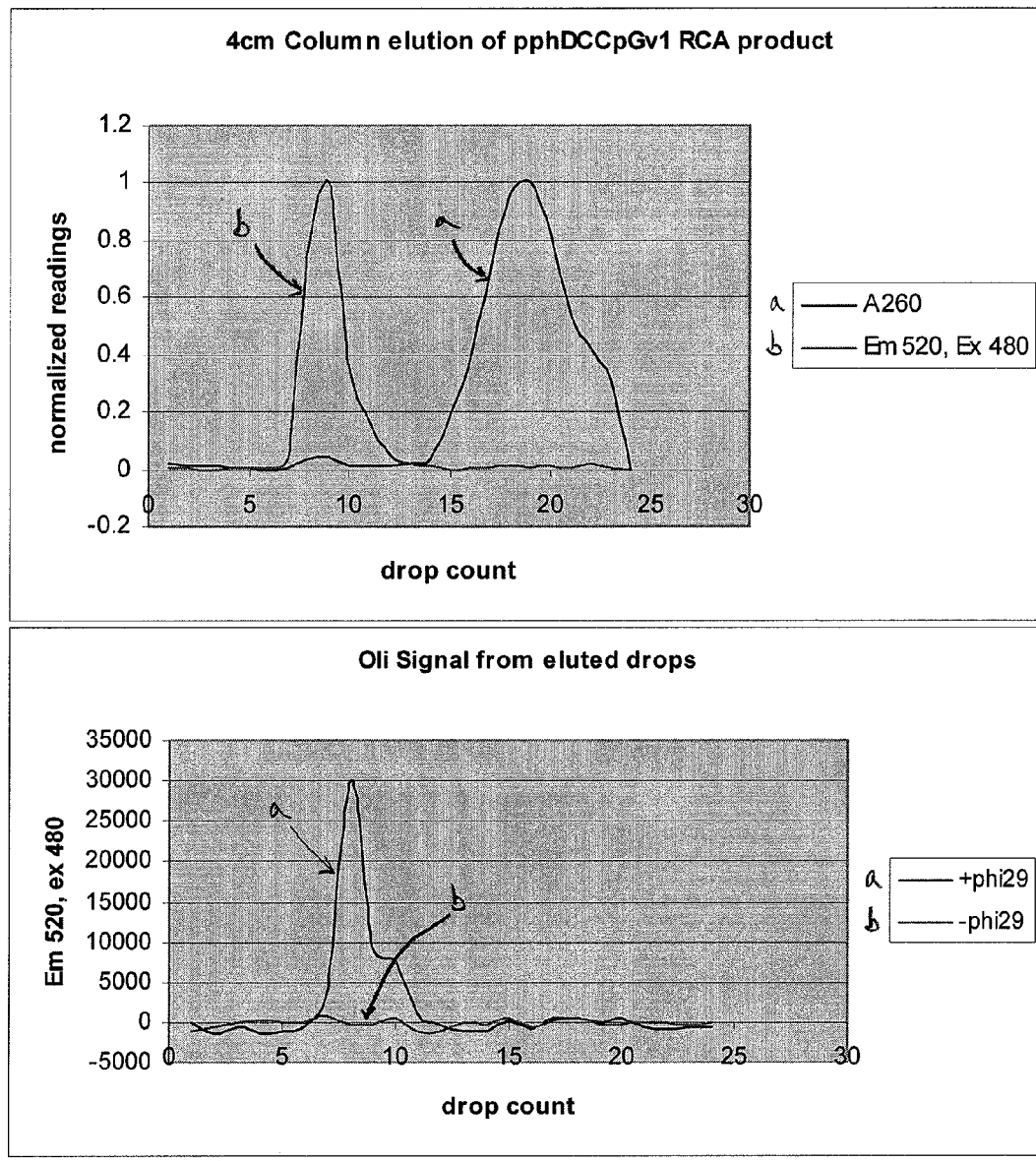
FIG. 32 shows graphs of spectrometer readings vs. drop count.

Protocol for size exclusion resins: 1. Template circles were RCAed at 1 nM in 50 µl volumes for 30 minutes and stopped with 5 µl 500 mM EDTA. Oli Green 1× was included in the reaction. 2. EconoColumns (BioRad) 0.5 cm internal diameter×5 cm length were filled with Bio-Gel P-100 Medium Resin (90-180 µm hydrated radius, fraction range 5-100 kDa). The resin was hydrated in PBS and was packed to a column height of 3.7 cm, total column volume 726 µl. PBS elution buffer was drained to the top of the column and 50 µl of sample was applied and 1 drop was released from the bottom of the column to let sample enter resin—column was then closed. 1 mL of PBS was added to provide hydrostatic pressure (this was kept constant as column flowed) and drops were collected on full flow rate. Drops were then measured for A260 and Ex 480 Em 520 showing clear fractionation between nucleotides and DNA created (FIG. 32).

Method to Purify Small Volumes of Particles by Drop Dialysis & Centrifugal Cconcentration Protocol for drop dialysis: 1. RCA products were made at 1 nM in 100 pl with ligations from the streptavidin padlock probe for 5, 10, 30 and 60 minutes respectively and stopped with 10 µl 500 mM EDTA. 2. Three Millipore MF membranes 0.05 µm VMWP (2.5 cm) were floated on 100 mL TBS in a glass dish until hydrated. 30 µl from each time point was applied for each time point. 20 µl of each sample was recovered at the appropriate time point. Time points were 30, 60, and 120 minutes. A zero time point was not applied but kept aside. 3. 10 µl of each recovered sample from each time point was mixed with 40 µl TBS and 0.125 (1×) stock Oli Green and measured at ex 480 em 520.

Figure 33:
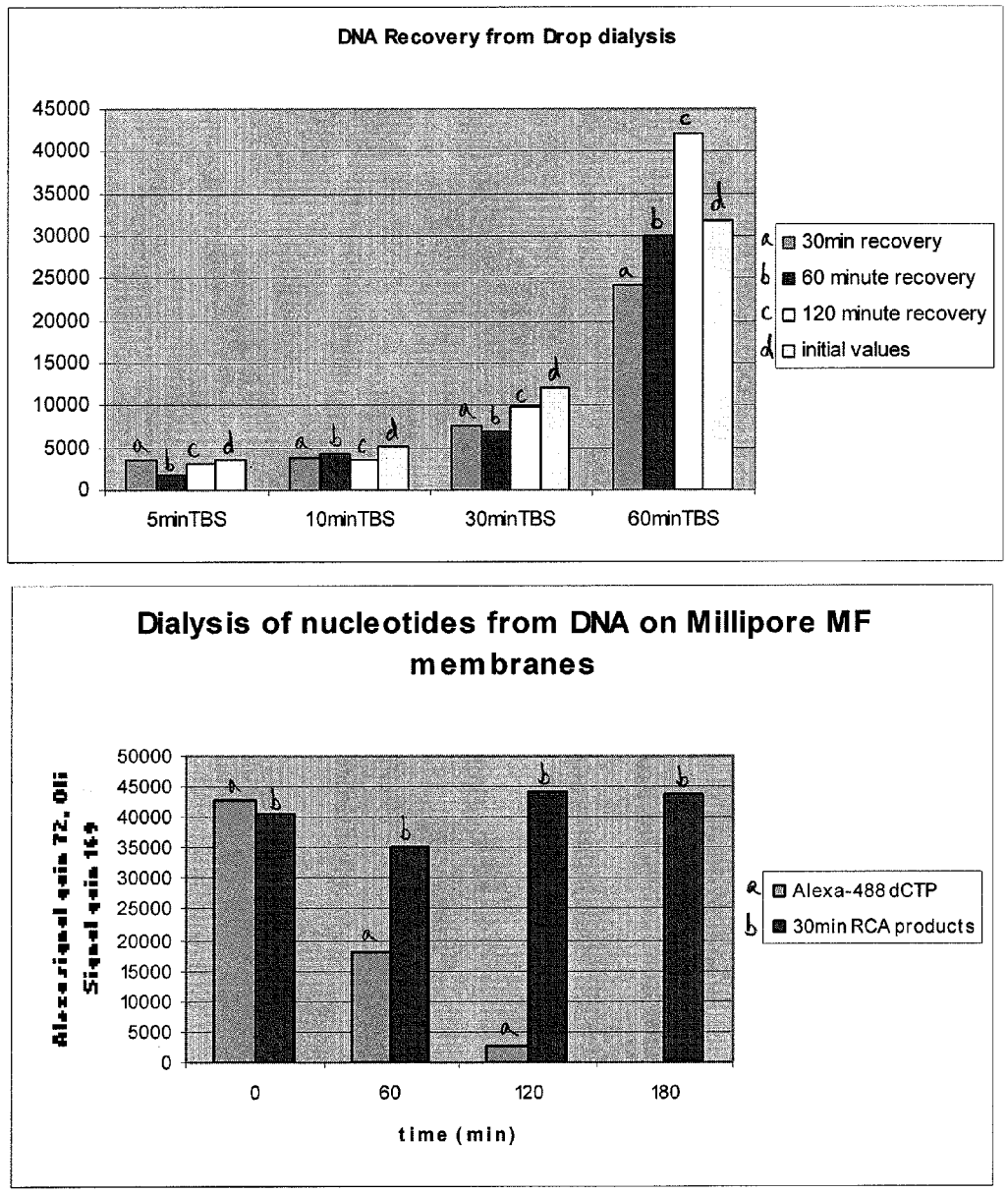
FIG. 33 shows graphs of DNA recovery from drop analysis, and dialysis of nucleotides from DNA on Millipore MF membranes.

FIG. 33 shows a drop dialysis recording of 30 minute unlabelled RCA reaction (normal dNTPs) along side a different drop containing Alexa-488 nucleotides. Every hour 1 µl of each drop was removed and diluted in 50 µl PBS and measured. The Alexa-488 nucleotides were measured by simple fluorescence and the DNA was measured by Oli Green.

Figure 35:
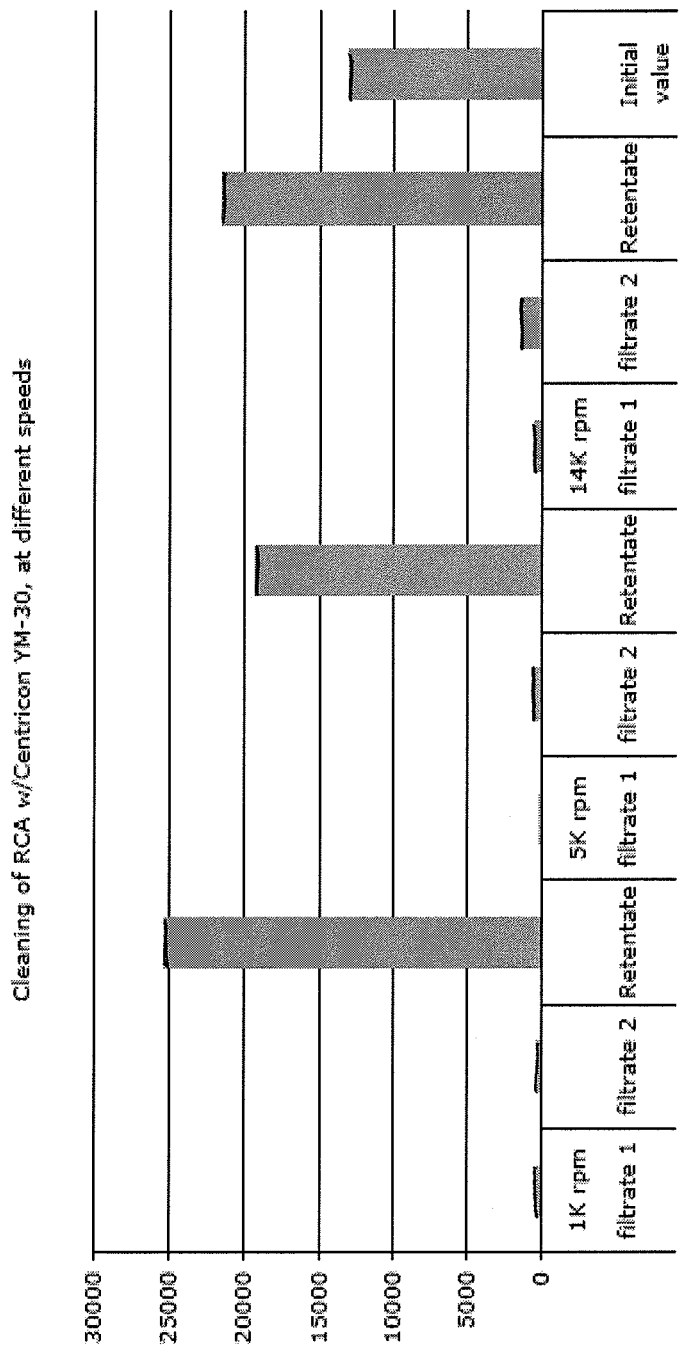
FIG. 35 shows a graph of cleaning of RCA with centricon YM-30 at different speeds.

DNA particles were cleaned with centricon YM-30 column at different speed. Speed 14,000 rpm and 5,000 rpm gave similar amount of flow through, but 1,000 rpm did not seem sufficient to drive the liquid through the membrane in a reasonable time (FIG. 35).

Method for DNAse and Exonuclease Resistance Profiles

Figure 36:
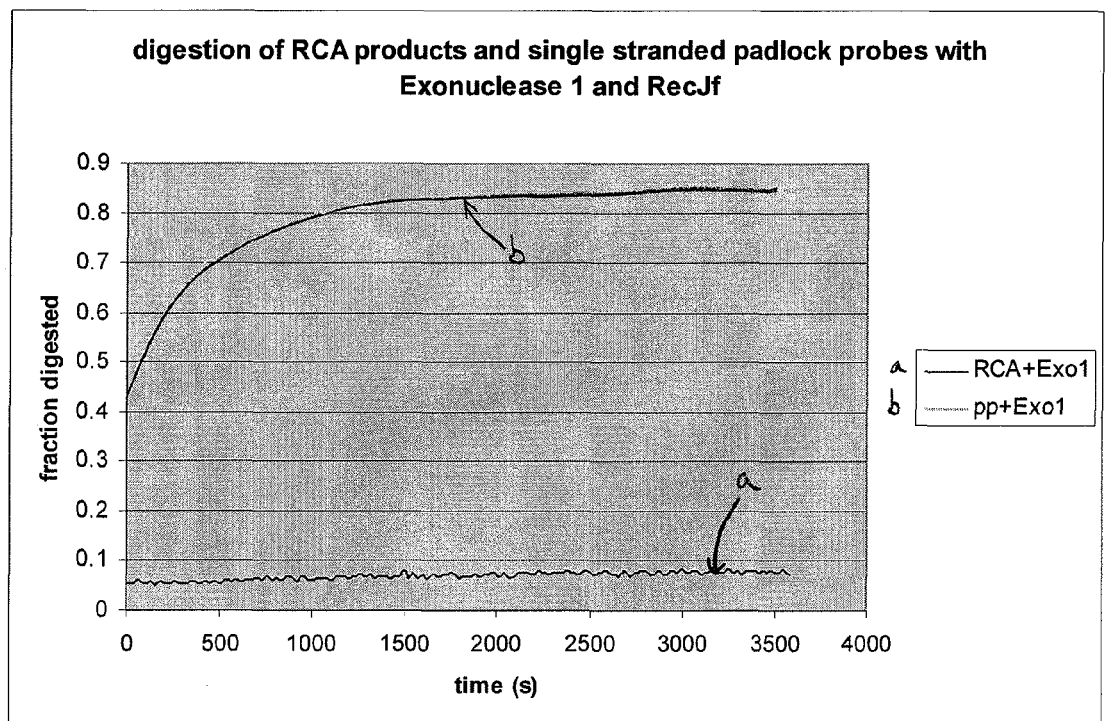
FIG. 36 shows a graph of digestion of RCA products and single stranded padlock probes with Exonuclease I and RecJf.

Step 1. Template circles were RCAed at 1 nM using phosphodiester dNTPs for 10 min at 30° C. and heat inactivated at 65° C. for 10 min. Step 2. RCA products were mixed 1:1 with 1×NEB buffer 2 containing 2× OliGreen stock dye. Step 3. Similarly, ss probe (unligated linear templates) was diluted to 100 nM in phi29 buffer and mixed 1:1 with 1×NEB buffer 2 containing 2× OliGreen. Step 4. Each sample was divided into 3 equal aliquots of 100 μl and each aliquot received either 20 units Exonuclease 1 or nothing. Samples were monitored by Ex 480 Em 520 at 37° C. over 1 hour with 20 second interval reads. Step 5. Percent digestion is calculated as the 1−(the ratio of the digested signal to blank signal). Step 6. RecJ may not be optimal. Also note that the ExoI digestion was already very progressed by the time readings started (FIG. 36).

More experiments to characterize DNA particles include experiments where serum stability and interactions are tested. The incorporation of nucleotides with free carboxy, thiol, amine for conjugating other small molecules is tested. Incorporation of biotinylated nucleotides is tested. Attenuation of nuclease sensitivity by incorporation of modified DNA or RNA backbones is tested.

Labeled with DNA Binding Dye (Oligreen) by Flow Cytometry & Microscopy

Figure 37:
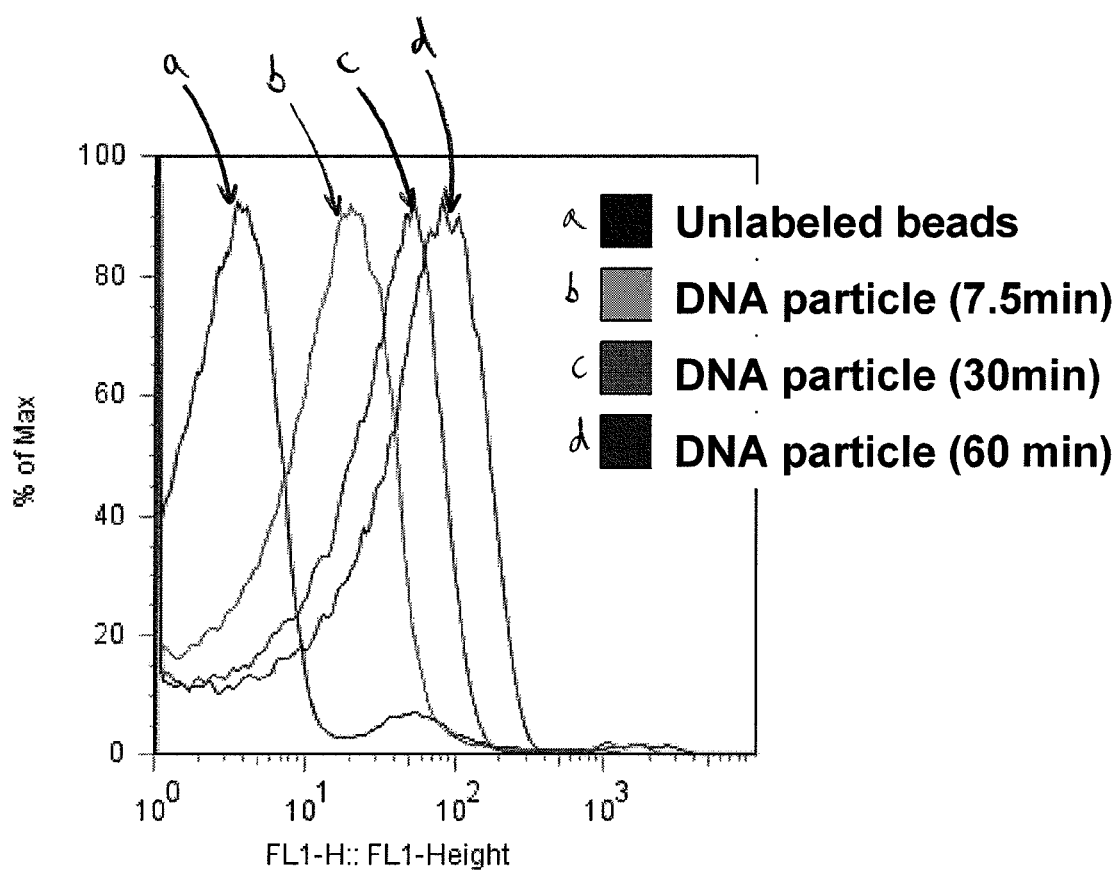
FIG. 37 shows a graph of fluorescence intensity for various DNA particles.

DNA particles were made by RCA reactions of varying times, labeled with Oligreen dye, and run on a flow cytometer. The fluorescence intensity correlates with the length of the reaction and presumably the size of the particles (FIG. 37).

Figure 38:
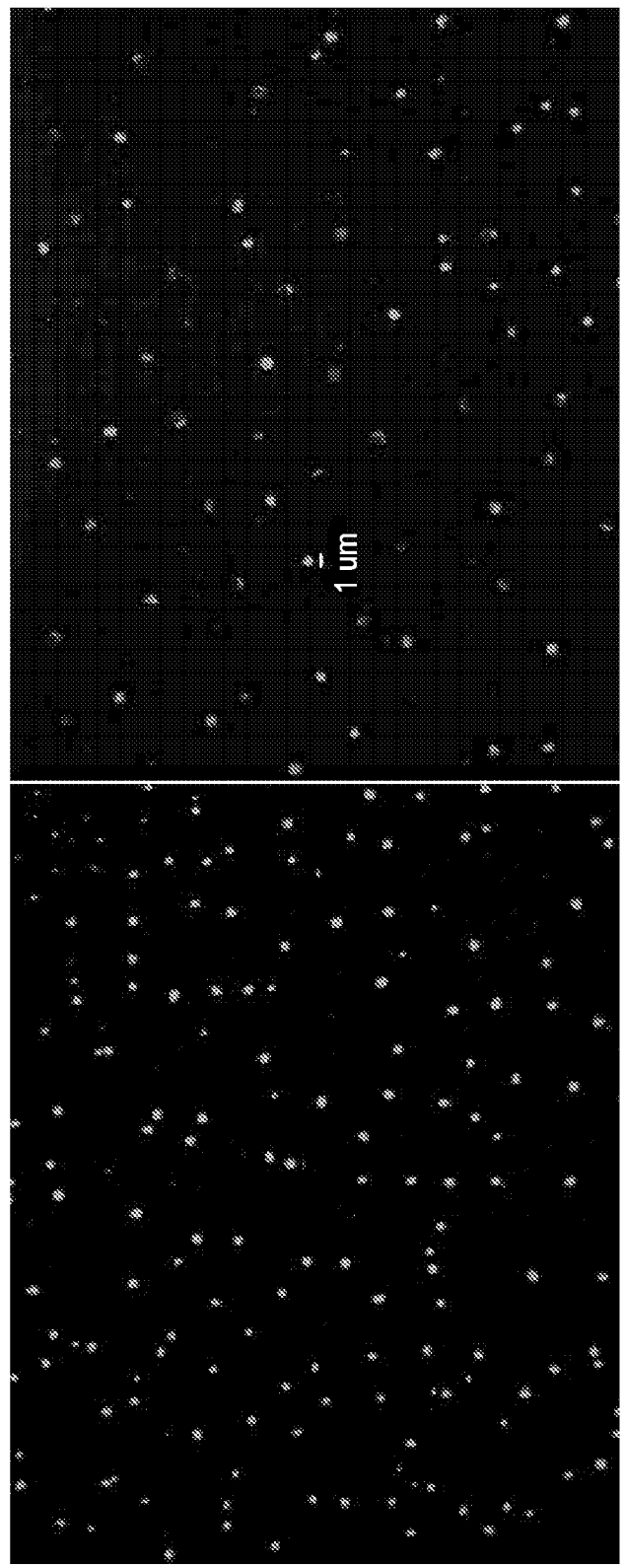
FIG. 38 shows DNA nanoparticles visualized with Sybr Green dye. Lower panel: 100× of 30 min RCA. Upper panel: 100×90 min RCA. Particle density is dependent on the spot and the time it has been under the light (photo-bleaching occurs).

DNA nanoparticles visualized with Sybr Green dye (FIG. 38). LEFT: 100× of 30 min RCA, RIGHT: 100×90 min RCA. Particle density is dependent on the spot and the time it has been under the light (photo-bleaching occurs).

Labeled with Incorporated Fluorescent Nucleotides or Hybridized Probe by Flow Cytometry.

Figure 39:
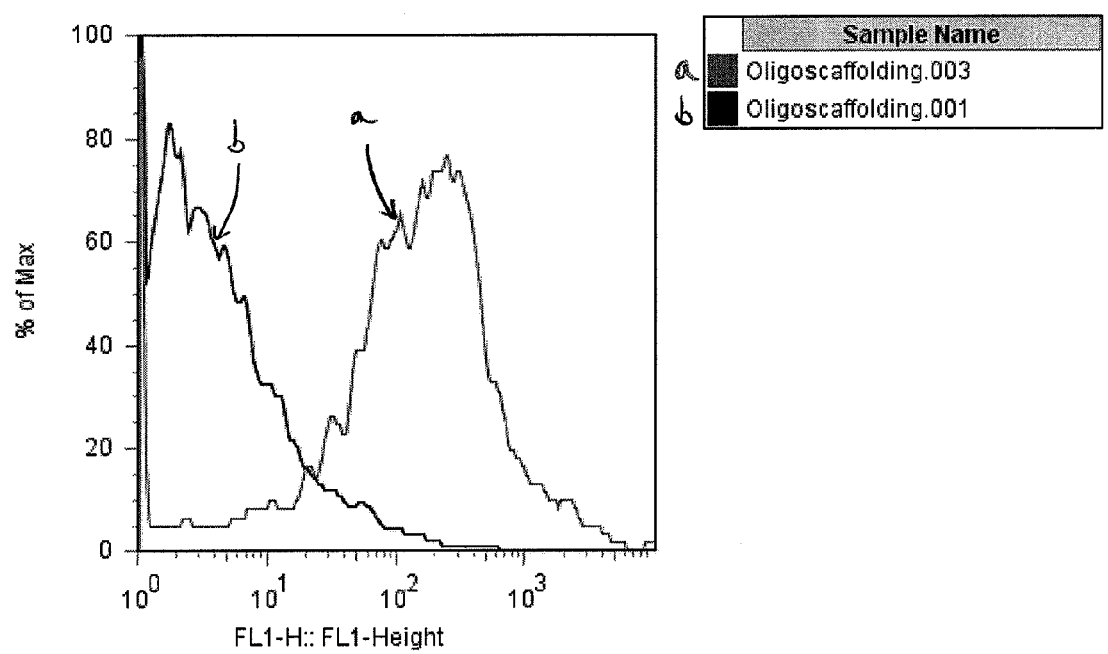
FIG. 39 shows a graph of incorporated Alexa 488 fluorescence.
Figure 40:
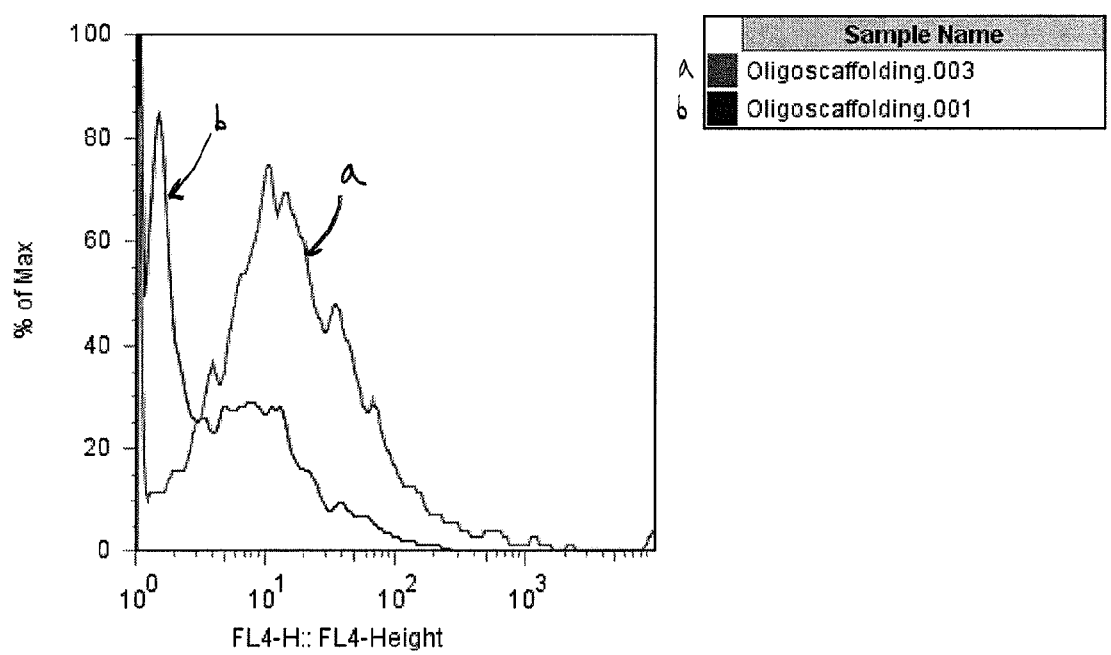
FIG. 40 shows a graph of hybridized probe fluorescence.

This is an example of Alexa-488 labelled DNA balls. The experiment was to hybridize on Alexa-647 oligos and see dual fluorescence. Sample 1 was the non labelled DNA with no oligo. Sample 3 was Alexa-488 labelled DNA hybridized to Alexa-647 tagged oligo. The incorporated Alexa 488 fluorescence is shown in FIG. 39, while the hybridized probe fluorescence is shown in FIG. 40.

Size Distribution by Dynamic Light Scattering

Figure 41:
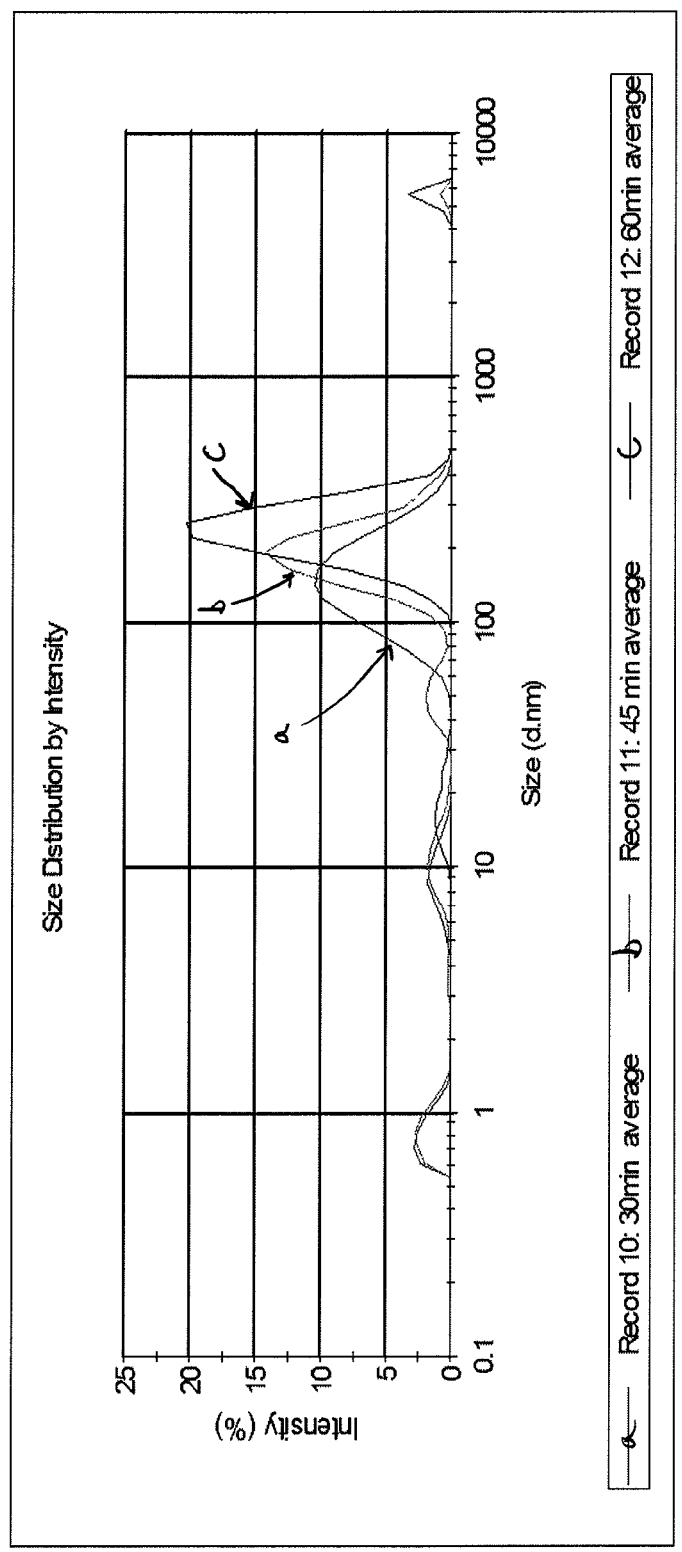
FIG. 41 shows a graph of size distribution by intensity.

A Zetasizer Nano instrument was used to measure the size distribution of DNA nanoparticles produced by RCA reactions of varying time, using dynamic light scattering (FIG. 41). We have noticed in other batches that the size seems to peak around 250 nm, even with longer reaction times. It is suspected that the size of the particles may be limited by the processitivity of the phi29 enzyme. Dynamic light scattering may also underestimate size due to the low index of refraction of the particles.

Agarose Gel Electrophoresis

Figure 42:
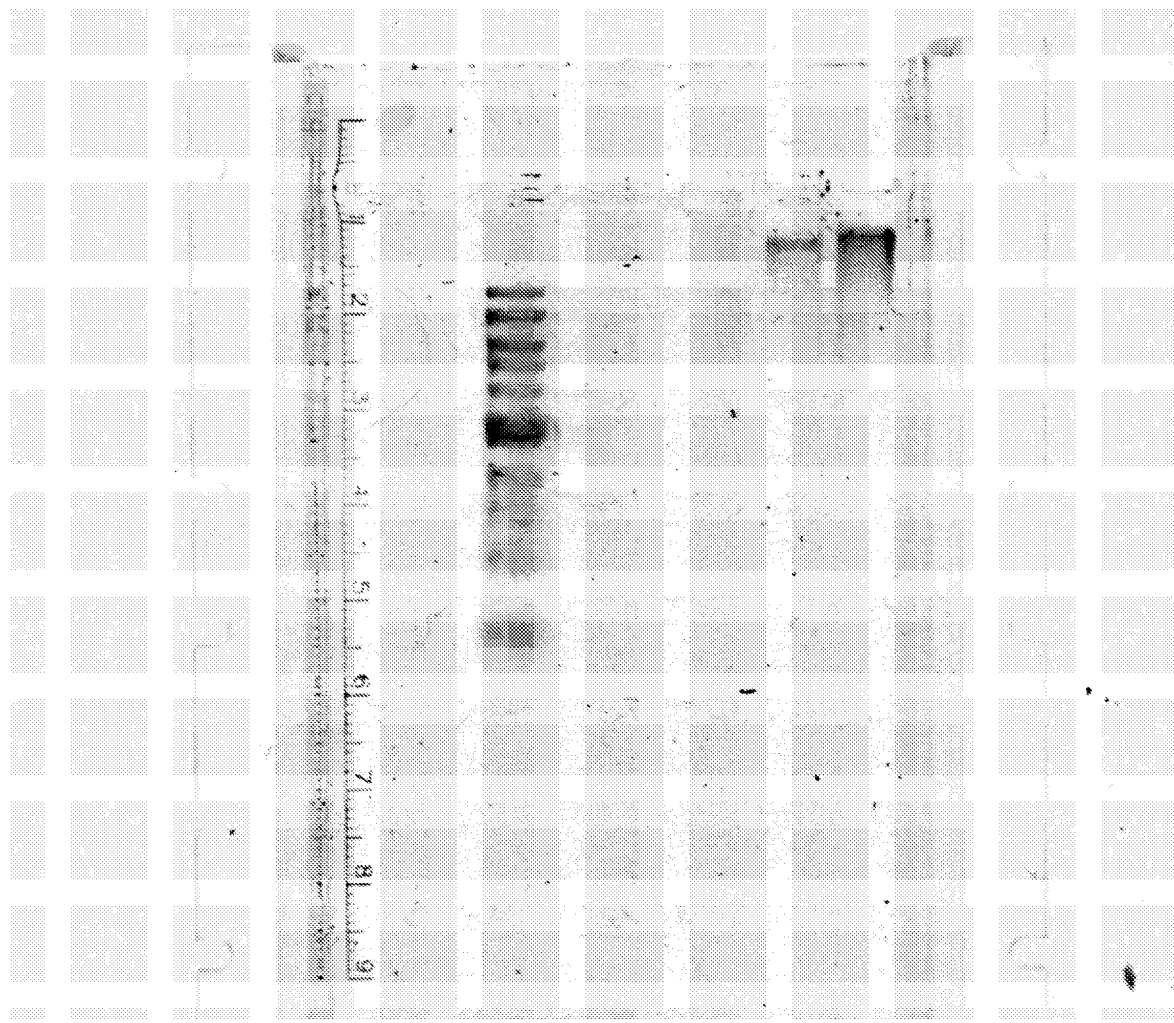
FIG. 42 shows a photograph of an agarose gel.

RCA reactions were run for time points 30 sec, 1 min, 2 min, 5 min, 10 min across left to right from the 1 kb ladder (FIG. 42). The top band on the ladder is 10 kb. The RCA reactions were stopped on time by EDTA and then mixed with alkaline denaturing buffer. They were then heated to 95° C. for 5 min. The gel was a 0.7% agarose alkaline gel. Samples were run for 3 hours at 40 V and stained with GelRed. The products (including the ladder) should be rendered single stranded by the alkaline conditions.

In more experiments to visualize DNA nanoparticles, nanoparticles are visualized using electron microscopy.

Example 8

Generating a DNA Particle Library

Methods to Produce, Select, Amplify, and Reproduce DNA Particles

An overview of the strategy is shown in FIG. 6. (A) LIGATION: (1) Prepare the buffer and add the library and the gluing primer (gp). (2) Boil a water bath, mix solution well and place in water bath. Allow water to cool to RT slowly. (3) Once about 33° C., add 1 μl T4 ligase and ligate at RT for 1 hour. TABLE 1 summarizes components of the reaction.

TABLE 1

| | Component | Volume |
|---|---|---|
| buffer | Water | 41.5 μl |
| | T4 ligase 10X buffer | 5 μl |
| | 500 mM DTT | 0.5 μl |
| | Total: | 47 μl |
| | 10 μM library | 0.5 μl |
| | 10 μM gp | 1.5 μl |
| | T4 ligase | 1 μl |

(B) VERIFICATION OF THE RINGS (RCA): (1) Add 49 μl of the master mix with oli green and add 0.5 μl of ligated sample. (2) Ensure that the TECAN is at 30° C. and add 0.5 μl phi 29 polymerase. (3) Mix together and run in TECAN with program 3Hour RCA FAM to visualize linear amplification—note slope of curve. (4) Run a reference sample with: 0.5 μl sal inv pp (Standard for RCA). TABLE 2 summarizes components of the reaction.

TABLE 2

| Component | Volume | | |
|---|---|---|---|
| Water | 40.5 μl | 101 μl | 413.1 μl |
| 10X phi buffer | 5 μl | 12.5 μl | 51 μl |
| dNTPs 10 mM | 3 μl | 7.5 μl | 30.6 μl |
| 500 mM DTT | 0.5 μl | 1.25 μl | 5.1 μl |
| Oli Green from stock | 0.125 μl | 0.313 μl | 10.2 |
| Ligated sample (1 nM) | 0.5 μl | | |
| Phi29 polimerase | 0.5 μl | | |

(C) CREATION OF DNA BALLS: (1) Add to the 49 μl of the Master Mix 0.5 μl of ligated sample. (2) Right before starting the program add 0.5 μl phi 29 polymerase. (3) Run all tubes at 30° C. for 30 minutes. (4) Stop the reactions with 5 μl 500 mM EDTA—Mix well and store at 4° C. TABLE 3 summarizes components of the reaction.

TABLE 3

| Component | Volume | | | |
|---|---|---|---|---|
| PCR water | 40.5 μl | 101.25 μl | 141.75 μl | 413.1 μl |
| 10X phi buffer | 5 μl | 12.5 μl | 17.5 μl | 51 μl |
| dNTPs 10 mM | 3 μl | 7.5 μl | 10.5 μl | 30.6 μl |
| 500 mM DTT | 0.5 μl | 1.25 μl | 1.75 μl | 5.1 μl |
| Ligated sample | 0.5 μl | | | |
| Phi29 polimerase | 0.5 μl | | | |

(D) ELISA WELLS: (1) Rinse the Elisa well 2 times with TBS-Tween and 2 times with TBS. (2) Add the solution (~55 μl) in the well and incubate for 20 min in a shaker. (3) Rinse 3 times with TBS-Tween and 3 times with TBS. (4) Elute with 26.6 μl of 0.04% biotin in DI-Water. (5) Let it rest in a shaker for 20 min. The 55 μl can be divided into two parts and select with those. This decreases the risk of loosing some of the positive samples. In addition the two parts can be taken along and at the end, at the PCR cleaning, be re-combined again.

(E) PCR: (1) Take the 26.5 μl of the selected RCA and add 22 μl of PCR mmx and 1 μl of VB and VF; (2) Add 0.5 μl of Stoffel enzyme. (3) Program: Open SYBR Green with Dissociation curve protocol. Select the correct wells that your samples. Thermal profile: START: 120 sec at 95° C.; CYCLES: 35 cycles, 30 sec at 95° C., 60 sec at 61° C., 20 sec at 72° C. END: 60 sec at 95° C., 30 sec at 55° C., 30 sec at 95°

C. (4) Remove 25 μl from each tube and store in new tubes to be run in a gel for analysis—use a 1.5% precast Gel Red agarose gel run at 115 V for 1 hr. (5) Remove 15 μl from each of the two remaining and transfer to a new tube and store at −20° C. for future reference. (6) Put aside 10 μl of the solution for the asymmetric PCR. TABLE 4 summarizes components of the reaction.

TABLE 4

| Component | Volume | | | |
|---|---|---|---|---|
| PCR Water | 26.5 μl | 66.25 μl | 92.75 μl | 278.25 μl |
| Stoffel 10X Buffer | 5 μl | 12.5 μl | 17.5 μl | 52.5 μl |
| 10 mM dNTPs | 5 μl | 12.5 μl | 17.5 μl | 52.5 μl |
| 25 mM MgCl$_2$ | 10 μl | 25 μl | 35 μl | 105 μl |
| 100 X SYBR (final conc 2X) | 1 μl | 2.5 μl | 3.5 μl | 10.5 μl |
| 10 μM vB (200 nM final conc) | 1 μl | 2.5 μl | 3.5 μl | 10.5 μl |
| 10 μM vF protected Phos | 1 μl | 2.5 μl | 3.5 μl | 10.5 μl |
| Stoffel Fragment | 0.5 μl | | | |

(F) GEL: Create gel: 100 mL 0.5×TBE buffer, 2.5 g Agarose. Boil: 60 sec MIX, 30 sec MIX, 10-30 sec and mix until liquid. Add 10 μl of 10000× GelRed dye. Pour gel (~50 mL) on the tray and add the comb. Let it cool (~20-30 min). Only once cooled remove the comb. Solutions for the gel: 15 μl sample. 6 μl diluted dye. (160 μl water+40 μl of Bluejuice 10× and 40 μl Bluejuice 10×). Run 1.5 μl only for the ladder (100 bp) vs the 20 μl total of sample w/dye. Load a bit of 0.5 TBE buffer on the platform, add the gel in the tray and cover it with buffer. Run at 70V for 80 min (G) ASSYMMETRIC PCR: Mix together 10 μl of the PCR product with 37.5 μl of a PCR mmx and 2 μl of VF protected phosphate. Add 0.5 μl of Stoffel Fragment, flick and put in the machine. Program: Start: 120 sec @ 94° C.; Cycles: 10 cycles, 30 sec at 94° C., 60 sec at 61° C., 20 sec at 72° C. Rest: 4° C. After the asymmetric PCR, PCR clean each sample. TABLE 5 summarizes components of the reaction

TABLE 5

| Component | Volume | | |
|---|---|---|---|
| PCR water | 21.5 μl | 53.75 μl | 225.75 μl |
| 10X Stoffel Buffer | 4 μl | 10 μl | 42 μl |
| dNTP 10 mM (2.5 mM ea) | 4 μl | 10 μl | 42 μl |
| MgCl$_2$ (25 mM) | 8 μl | 20 μl | 84 μl |
| vF protected phos (final conc. 400 nM) | 2 μl | 5 μl | |
| PCR product | 10 μl | | |
| Stoffel fragment | 0.5 μl | | |

(H) LIGATION 2 and after: To the cleaned sample add 5 μl of T4 ligase 10× buffer, 0.5 μl of 500 mM DTT and 1.5 μl of gluing primer added T. Boil water and place mix in water and allow to cool to RT. Add 1 μl T4 Ligase and ligate for 1 hour.

(I) VERIFICATION OF THE RINGS considerations from round 2 on (RCA): Ligation2Slope/slope standard=x. Ligation3Slope/slope standard=y. To get back to the same concentration you need to dilute:100 x/y μl of ligated sample over 100 μl of DI water.

(J) ELISA WELL consideration from round 2 on: If the sample on the PCR spikes too early, try to dilute it. After run 2 or 3 run the RCA in an empty container to see eventual non-specific binding.

Example 9

Selection Against a Cellular Target (Primary Human Dendritic Cells)

Procedure: 1. Count 105 cells to use in 1 mL. 2. Spin 3 min at 3000 rpm remove supernatant and add 50 μl of RCA. 3. Let react for 1 hr on ICE. 4. At the same time put 1.2 mL of Cell media on as many eppendorf as the planned rinses steps and keep it in the ice box. 5. Spin the cells 3 min at 3000 rpm. 6. Remove the supernatant and rinse with 500 μl of COLD 5% BSA in PBS. 7. Remove the cell media from one of the test tube and add the liquid with the cells. 8. Discard the empty tube. 9. Repeat it as many times as your rinses steps. 10. Remove the supernatant and add 50 μl of Hypotonic Lysis buffer and 3 μl of Proteinase K (10 mg/mL). 11. Put in heat block at 56° C. for 1 hr. 12. Move to a second heat block in order to stop the protease at 95° C. for 15 min. 13. The sample is ready to be used.

Figure 43A:
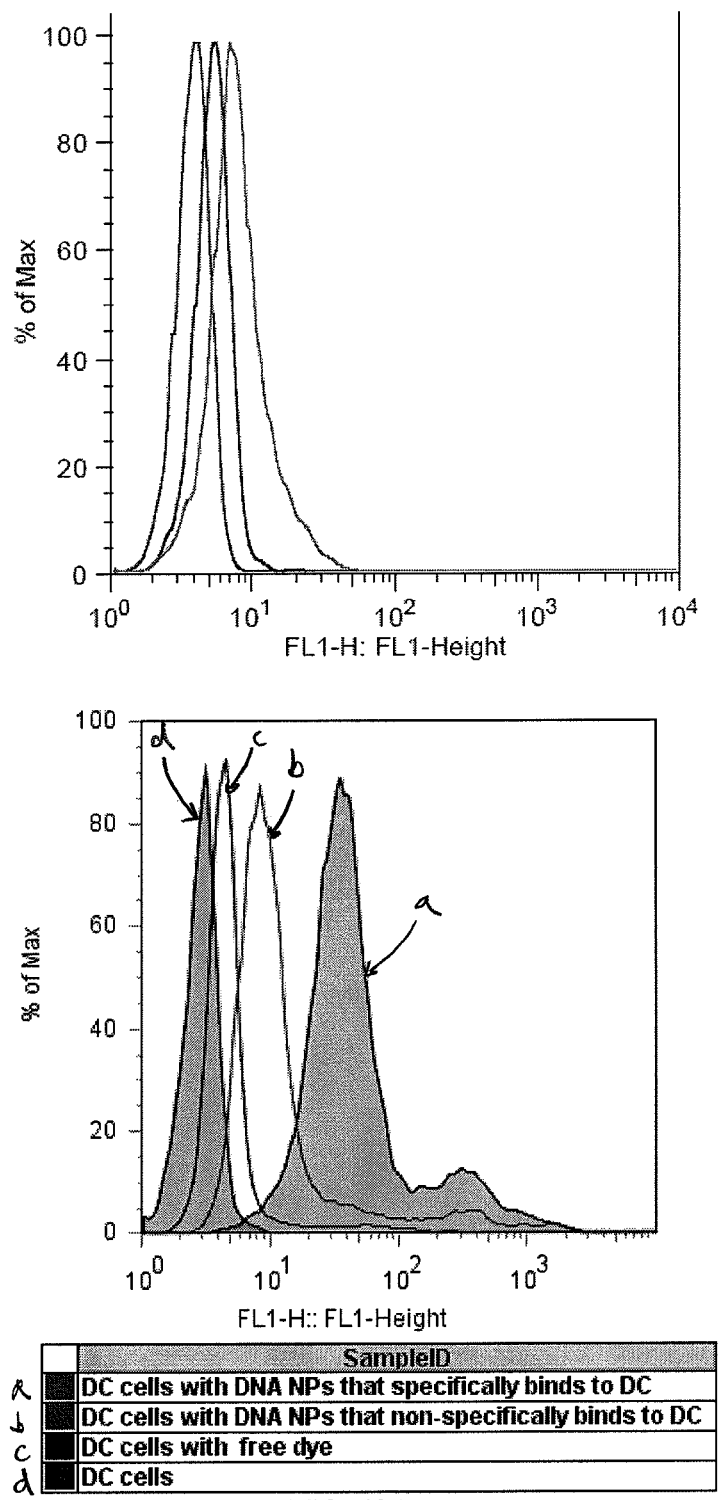
FIG. 43A shows graphs of fluorescence intensity, and includes an example of a cloned particle (shaded) with high affinity for DC as compared to a control particle (red) or unstained cells (blue and grey).

Results of a selection against dendritic cells (DC). The final pool of particles after 7 rounds of selection by the procedure above was labeled with alexa nucleotides and added to dendritic cells (green line). An irrelevant particle was used as a control (blue line). The red line is the cells alone. The shift in fluorescence, as measured by flow cytometry, indicates enrichment of DC binding particles. The pool of particles was cloned into a plasmid vector and individual clones selected, sequenced, and regenerated by PCR, ligation, and RCA to create individual clonal particle populations. These were then assayed as above. FIG. 43A shows an example of a cloned particle (shaded) with high affinity for DC as compared to a control particle (red) or unstained cells (blue and grey).

Figure 43B:
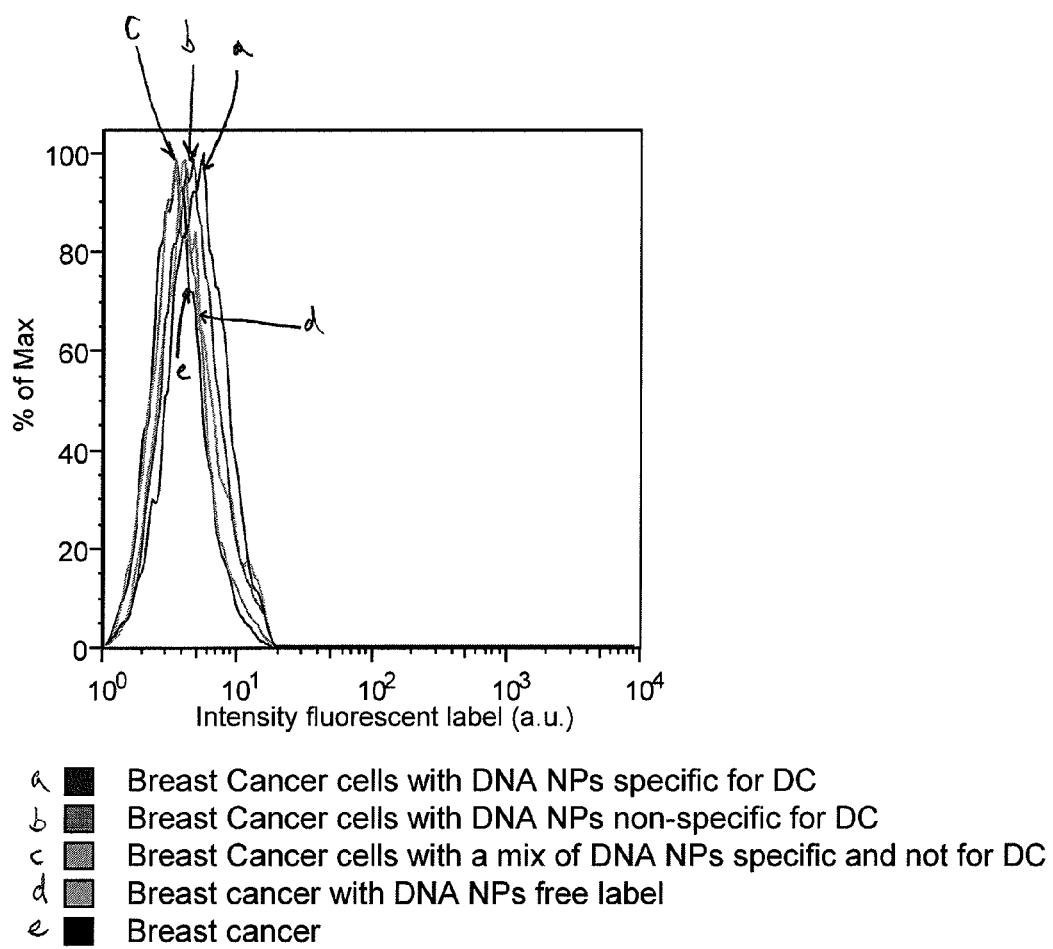
FIG. 43B shows a graph of fluorescence intensity, and includes an example of clonal particle was assayed against the MDA-MB-231 breast cancer cell line.

The same clonal particle was assayed against the MDA-MB-231 breast cancer cell line (FIG. 43B).

The particle originally selected against DC does not seem to bind the breast cancer cell line, suggesting that some level of cell specificity may have been achieved even without a counter selection strategy. This example shows selection resulting in unique sequence particles that bind to the cells much better than control particles In more experiments to select against a cellular target (primary human dendritic cells), resulting in unique sequence particles that bind to the cells much better than control particles the following experiments are carried out: Selective enrichment of particles that bind to one cell type preferentially over another is performed. In vivo selection for tumor targeting particles in a mouse model is carried out. Multi-library combinatorial selection is carried out. Selection for enzymatic activity is carried out.

Example 10

Functional Experiments

Loading of Doxorubicin into DNA Particles

Figure 44:
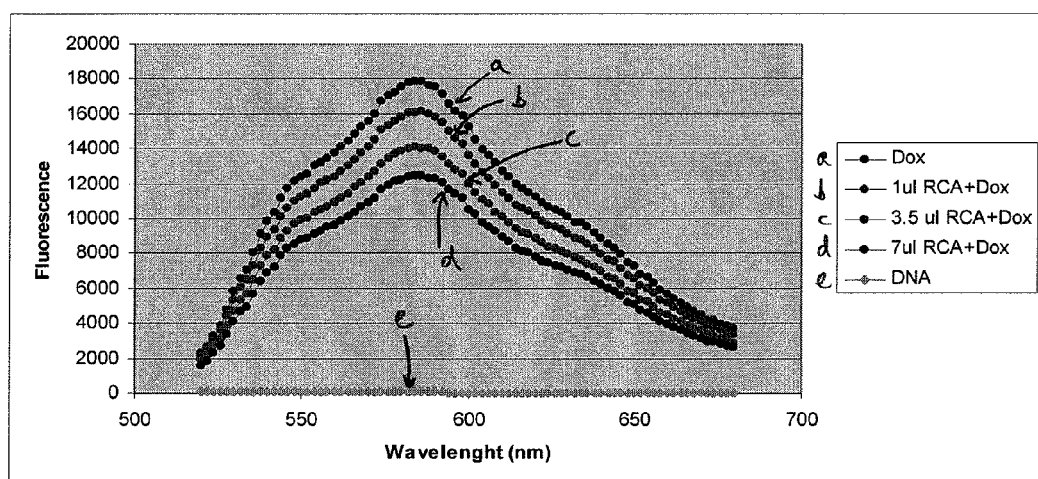
FIG. 44 shows a graph of fluorescence of particles loaded with doxorubicin.

The fluorescence of doxorubicin is quenched with the addition of DNA nanoparticles, indicating doxorubicin binding to the particles (FIG. 44).

Protection of Cells from Dox when Untargeted Particle is Used

Figure 45:
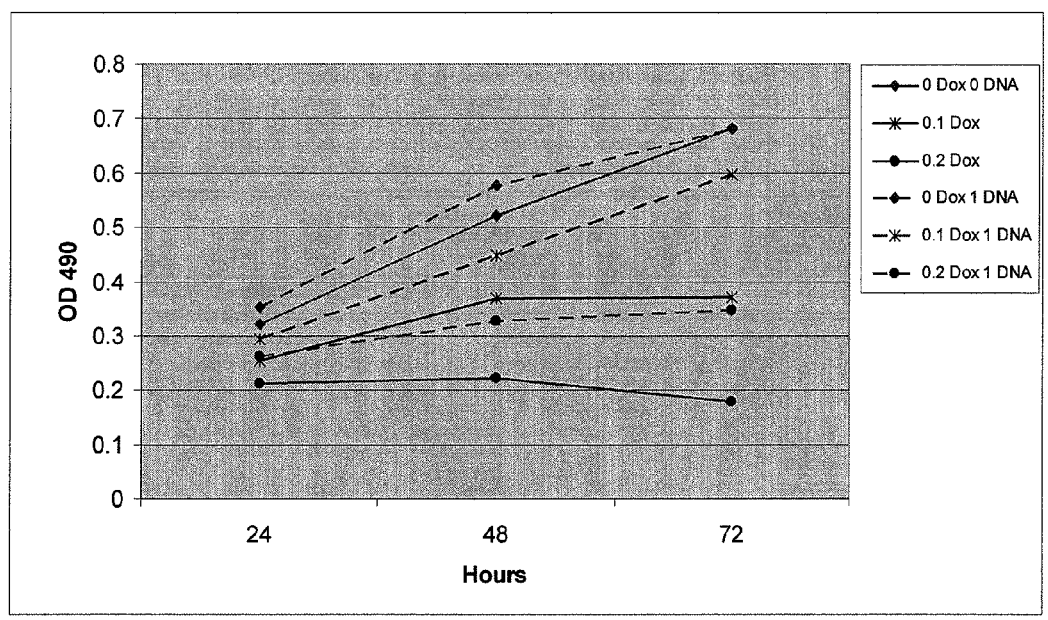
FIG. 45 shows a graph of OD490 over time.

The IC$_{50}$ was determined to be 0.1 μg of Doxo for 104 cells. When this amount of Doxo is incubated with the DNA particles, the survival is almost 100%, indicating that DNA absorbed the Doxo and protect cells from the toxicity of Doxo. This preliminary data indicate two things: (1) DNA is not able to get into the cells by itself. Targeted DNA particles may be selected or a targeting moiety added. (2) At the same time, DNA nanoparticles absorbed Doxo, which is good for our purpose of loading DNA with drugs (FIG. 45).

Lack of Non-Specific Activation of Immune Cells with Untargeted Particles

Figure 46:
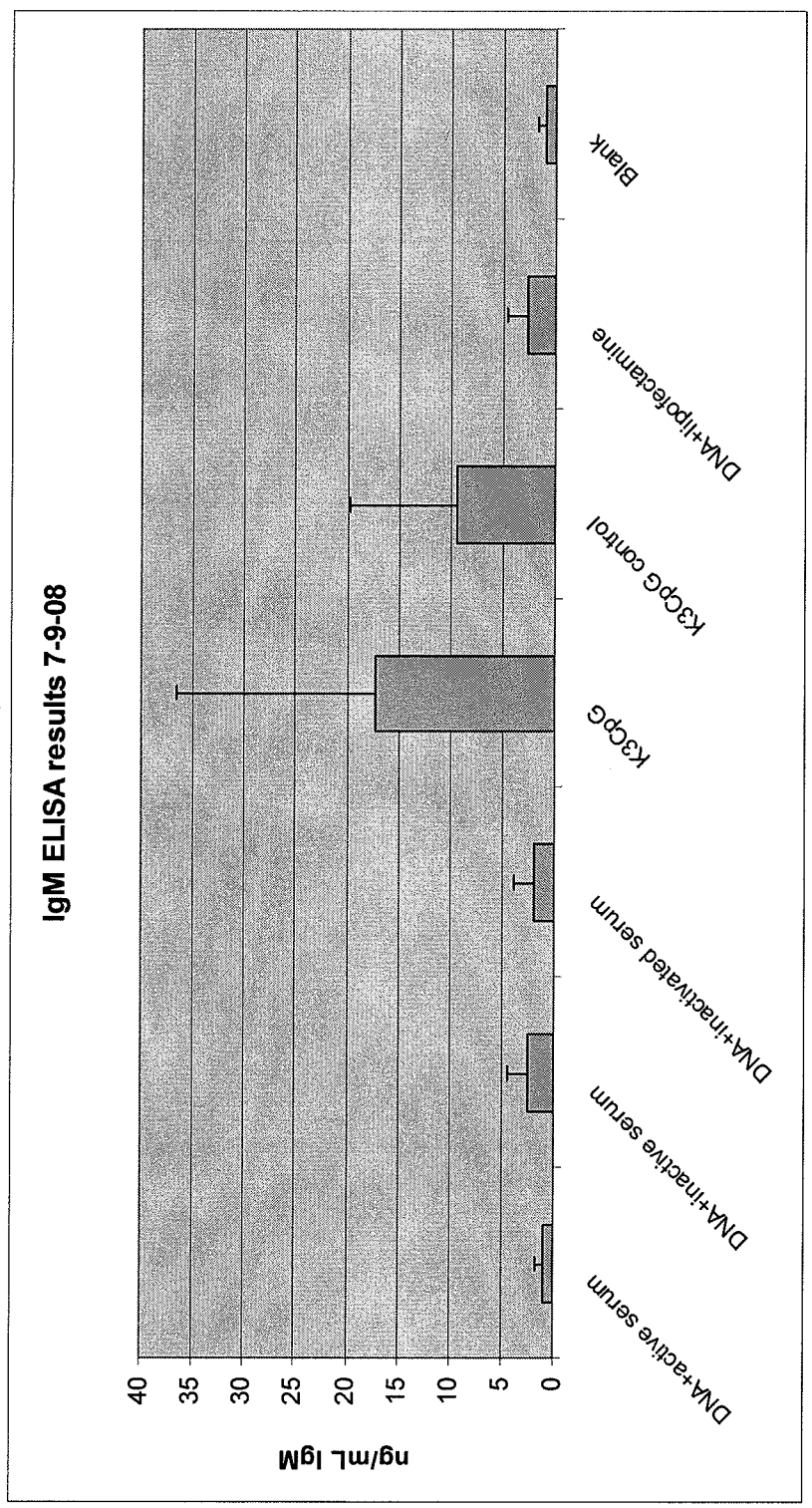
FIG. 46 shows a graph of IgM secreted from PBMC in the presence of nanoparticles.

DNA nanoparticles containing an immunogenic CpG sequence were incubated with PBMCs and IgM secretion measured. The K3 oligonucleotide is a positive control and contains the same stimulatory sequence as the DNA nanoparticles. "DNA" in the FIG. 46 refers to the nanoparticles. The experiments were conducted in both primary serum and heat inactivated serum.

In more experiments to demonstrate function of DNA nanoparticles the following experiments are carried out. Immune activation by targeted particle containing CpG motifs is performed. Immune activation by targeted particle hybridized to an immuno-stimulatory peptide is performed. Immune activation by chemical conjugation of a TLR3 agonist is performed. Immune activation by combinations of the above is performed. Cell targeting by hybridization of a targeted peptide is performed.

Example 11

Applications: Therapeutic

In experiments to demonstrate therapeutic applications of DNA nanoparticles the following experiments are carried out. Cancer therapy by targeted delivery of doxorubicin is performed. Cancer therapy by immune activation is performed. Cancer therapy by direct killing of tumor cells is performed. Vaccine adjuvant for protective vaccines is performed.

Example 12

Applications: Imaging

In experiments to demonstrate imaging applications of DNA nanoparticles the following experiments are carried out. Ex vivo imaging of cancer cells with tumor specific particles fluorescently labeled or biotinylated for histochemistry is performed. In vivo imaging with particles that hold contrast agents is performed.

Example 13

DeNAno: Selectable Deoxyribonucleic Acid Nanoparticle Libraries

DNA nanoparticles of approximately 250 nm were produced by rolling circle replication of circular oligonucleotide templates which results in highly condensed DNA particulates presenting concatemeric sequence repeats. Using templates containing randomized sequences, high diversity libraries of particles were produced. A biopanning method that iteratively screens for binding and uses PCR to recover selected particles was developed. The initial application of this technique was the selection of particles that bound to human dendritic cells (DCs). Following 9 rounds of selection the population of particles was enriched for particles that bound DCs, and individual binding clones were isolated and confirmed by flow cytometry and microscopy. This process, which has been termed DeNAno, represents a novel library technology akin to aptamer and phage display, but unique in that the selected moiety is a multivalent nanoparticle whose activity is intrinsic to its sequence. Cell targeted DNA nanoparticles may have applications in cell imaging, cell sorting, and cancer therapy.

The paradigm of nanotechnology for applications in the medical field has been oriented around the framework of bottom-up construction. Generally, a scaffold of polymer or metal serves as a basis for the addition of functional moieties to lend the nanomaterial the desired capabilities such as selective targeting, transport of therapeutic and imaging agents, and immune evasion (Ferrari, M. Cancer nanotechnology: opportunities and challenges. *Nat Rev Cancer* 5, 161-171 (2005)). When biopolymers such as DNA are used, they are often rationally designed to form a predetermined structure (Zhang, C. et al. Conformational flexibility facilitates self-assembly of complex DNA nanostructures. *Proc Natl Acad Sci USA* 105, 10665-10669 (2008)). However, this approach has overlooked a powerful tool of molecular biology: the simple creation and efficient combing of libraries with diversity of $10^9$ or more (Wilson, D. S. & Szostak, J. W. In vitro selection of functional nucleic acids. *Annu. Rev. Biochem.* 68, 611-647 (1999); Smith, G. P. & Scott, J. K. Libraries of peptides and proteins displayed on filamentous phage. *Meth-ods Enzymol.* 217, 228-257 (1993); Clackson, T., Hoogenboom, H. R., Griffiths, A. D. & Winter, G. Making antibody fragments using phage display libraries. *Nature* 352, 624-628 (1991)). Small nucleic acid aptamer sequences have been identified with binding and enzymatic properties, but their use in nanoparticle based applications has mostly involved grafting them onto other materials (Tuerk, C. & Gold, L. Systematic evolution of ligands by exponential enrichment: RNA ligands to bacteriophage T4 DNA polymerase. *Science* 249, 505-510 (1990); Ellington, A. D. & Szostak, J. W. In vitro selection of RNA molecules that bind specific ligands. *Nature* 346, 818-822 (1990); Bartel, D. P. & Szostak, J. W. Isolation of new ribozymes from a large pool of random sequences [see comment]. *Science* 261, 1411-1418 (1993); Huang, C. C., Huang, Y. F., Cao, Z., Tan, W. & Chang, H. T. Aptamer-modified gold nanoparticles for colorimetric determination of platelet-derived growth factors and their receptors. *Anal. Chem.* 77, 5735-5741 (2005)). In this study, the concepts of diverse library selection methods with nanoparticles have been have fused by creating libraries of DNA nanoparticles by rolling circle replication of randomized circular templates and selecting for particles that bind to a target cell type.

Figure 47:
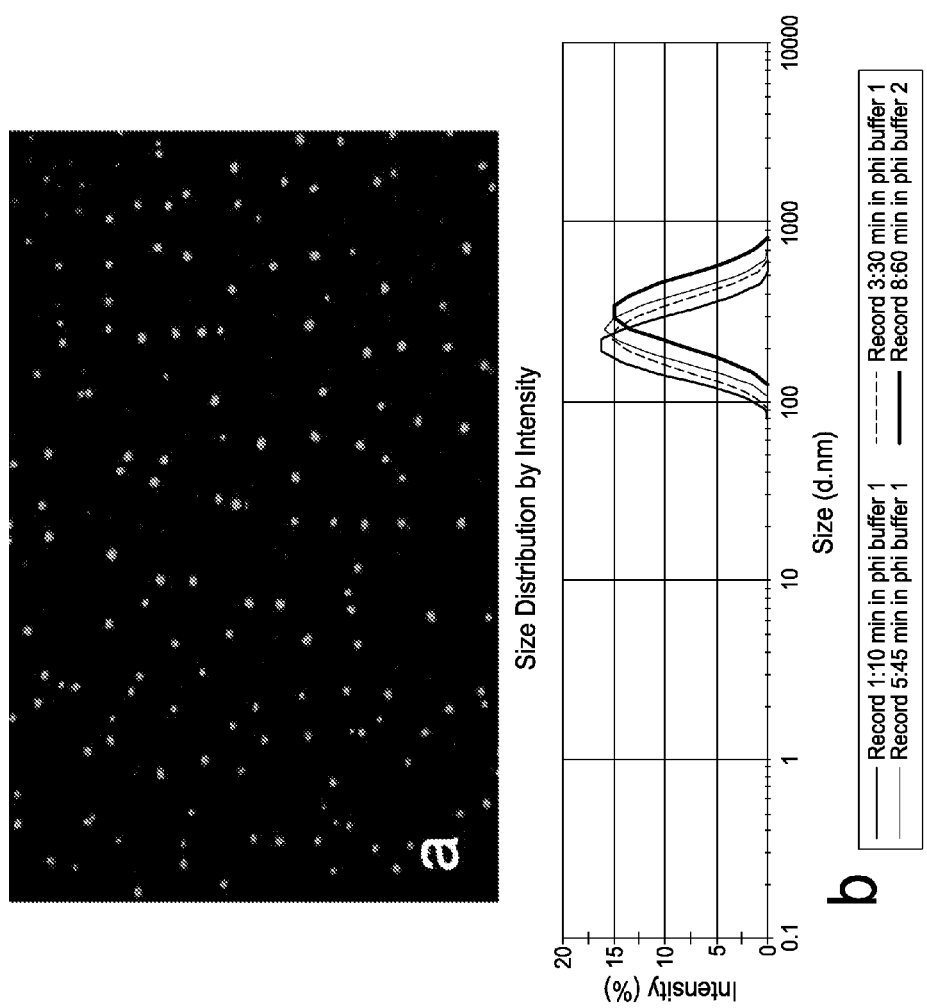
FIGS. 47A and 47B relate to production and basic characterization of DNA nanoparticles.
Figure 48:
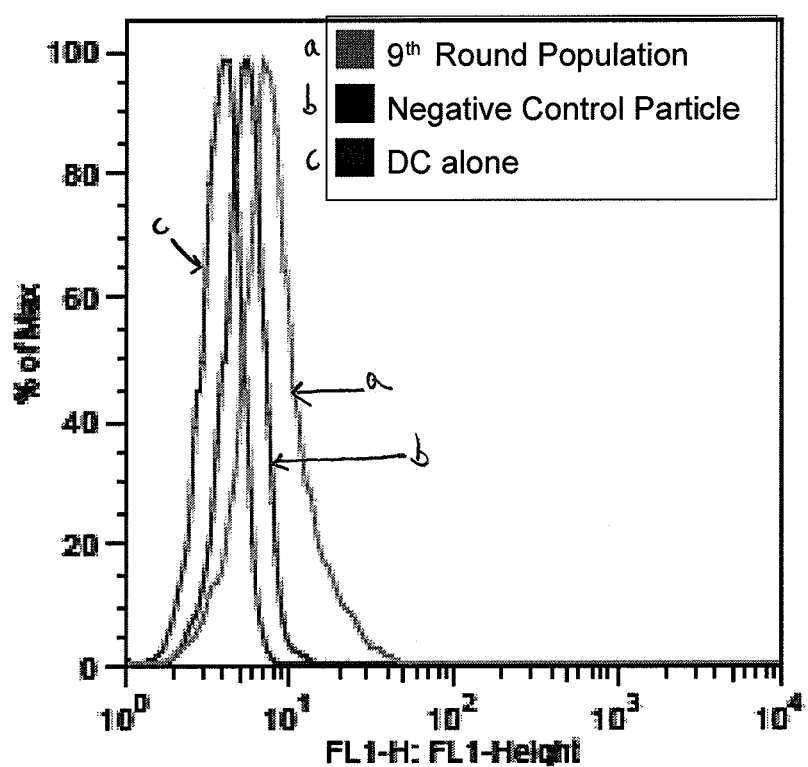
FIG. 48 and FIG. 49 relate to flow cytometry assays of DNA nanoparticles incorporating Alexa488 dCTP. Nine rounds of selection were performed as summarized in FIG. 9 after which the selected population was used to generate fluorescent DNA nanoparticles which were incubated against dendritic cells. From the $9^{th}$ round of selection, individual population members were cloned using a Promega pGEM-T cloning kit and served as templates for fluorescent nanoparticle generation which were individually incubated with dendritic cells. Of these clones, several were observed to bind DCs with varying degrees of efficacy. The variation can be seen in FIG. 49 which compares several "positive" clones to a "negative" clone with less binding capability.

Rolling circle replication of a circular oligonucleotide template using a strand displacing DNA polymerase produces a continuous single strand of DNA that is the concatemeric complement of the template. The single strand condenses into a discrete particle that can be visualized by fluorescent microscopy and flow cytometry if fluorescently labeled (FIG. 47) (Blab, G. A., Schmidt, T. & Nilsson, M. Homogeneous detection of single rolling circle replication products. *Anal. Chem.* 76, 495-498 (2004); Jarvius, J. et al. Digital quantification using amplified single-molecule detection. *Nat Methods* 3, 725-727 (2006); Larsson, C. et al. In situ genotyping individual DNA molecules by target-primed rolling-circle amplification of padlock probes. *Nat Methods* 1, 227-232 (2004)).

The processivity of the strand displacing enzyme most commonly used, phi29 DNA polymerase, is ~60 kb so that a particle produced from a 100-200 oligonucleotide template will consist of several hundred complementary copies. The size of the particles is a function of the reaction kinetics and can be controlled by stopping the reaction with saturating amounts of EDTA and/or heat in activation of the polymerase. Dynamic light scattering (DLS) estimates that particles produced from reactions of 10-60 minutes have hydrodynamic radii between 217-338 nm with polydispersity indices of 0.228-0.333 (FIG. 8). These measurements are in good agreement with a freely joined chain model of polymer condensation which estimates a 60 kb ssDNA strand to have a hydrodynamic radius of 379 nm (Austin, R. Nanopores: The art of sucking spaghetti. *Nat Mater* 2, 567-568 (2003)). Because of their large size and chaotic single stranded structure, the particles will not migrate in an agarose gel.

The library screening process consists of three major steps which are performed iteratively: particle synthesis, selection, and amplification. A random library template sequence (5'-Phos-GCGCGGTACATTTGCTGGACTA-$N_{60}$-TGGAG-GTTGGGGATTTGATGTTG 3'; SEQ ID NO:13) (Integrated DNA Technologies, Coralville, Iowa) was circularized with a template sequence (TCC AGC AAA TGT ACC GCG CCA ACA TCA AAT CCC CAA CCT; SEQ ID NO:14) using T4 DNA ligase (New England BioLabs, Ipswich, Mass.) and polymerized with phi29 DNA polymerase (NEB) for 30 minutes at 30° C. and terminated by addition of 50 mM EDTA. The initial library particle synthesis reaction produced over $10^{10}$ unique nanoparticles and was used to begin a selection directed against primary human dendritic cells with an eye towards vaccine or cancer immunotherapy applications (Fong, L. & Engleman, E. G. Dendritic cells in cancer immunotherapy. *Annu Rev Immunol* 18, 245-273 (2000)). Bound particles were amplified by PCR using primers that bound to the sequences flanking the random region. Because each particle contains several hundred copies of the sequence unit, PCR amplification from a single particle is robust. To regenerate the library, the desired single strand template was enriched after symmetric PCR by adding a 20 fold excess of the desired strand's phosphorylated primer v6F (5'-Phos-GCG CGG TAC ATT TGC TGG ACT A; SEQ ID NO:15). The regenerated single strands were then circularized to form a pool of template circles for the next round of particle synthesis and selection (FIG. 4). Briefly, DNA nanoparticle iterative selection scheme. ssDNA libraries are ligated with T4 ligase and polymerized with phi29 DNA polymerase. 3'-5' exonuclease activity of phi29 DNA polymerase ensures nanoparticle purity from extraneous DNA. Immature DCs were cultured in RPMI 1640 medium supplemented with 2 mM L-glutamine, 50 mM 2-mercaptoethanol, 10 mM HEPES, penicillin (100 U/mL), streptomycin (100 mg/mL), 5% human AB serum, 1000 U GM-CSF/mL and 200 U IL-4/mL and harvested in days 5-7. Cell incubation and washing followed by QPCR (200 nM primers, 95° C. 2 min, cycle 95° C. 30 sec, 61° C. 1 min, 72° C. 20 sec to completion. 5 µL of resultant reaction was added to 45 µL fresh PCR buffer with 400 nM phosphorlyated template primer v6F. 10 additional cycles of PCR generate an excess of the desired single strand. DNA was purified with a QIAquick Nucleotide Removal Kit (Qiagen, Valencia, Calif.), eluted into T4 DNA Ligase Buffer and recircularized to begin the next round. Nine rounds were produced after which sequences were cloned using a pGEM-T cloning kit (Promega, Madison, Wis.).

Figure 49:
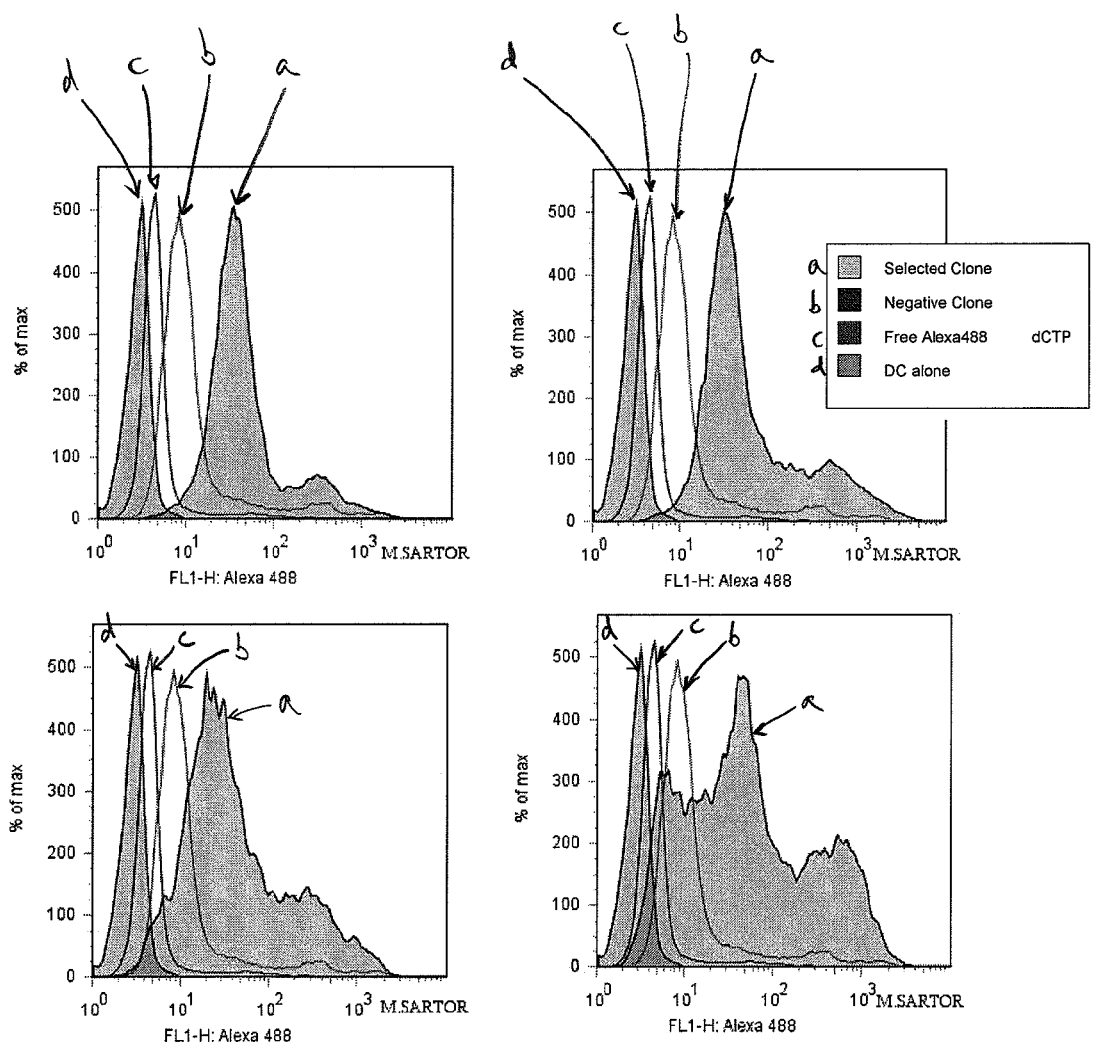

After nine rounds of selection the pool of selected sequences served as templates for the generation of fluorescent DNA nanoparticles by replacing 10% of total dCTPs with ChromaTide® Alexa Fluor® 488-7-OBEA-dCTP (Invitrogen, Carlsbad, Calif.) in the polymerization reaction and incubating for 30 minutes at 30° C. followed by inactivation by EDTA. These fluorescent nanoparticles were used in all analyses of binding by flow cytometry and microscopy. An increase in total population fluorescence was observed compared to a negative DNA nanoparticle control, suggesting that cell binding particles had become enriched (FIG. 49).

Figure 50:
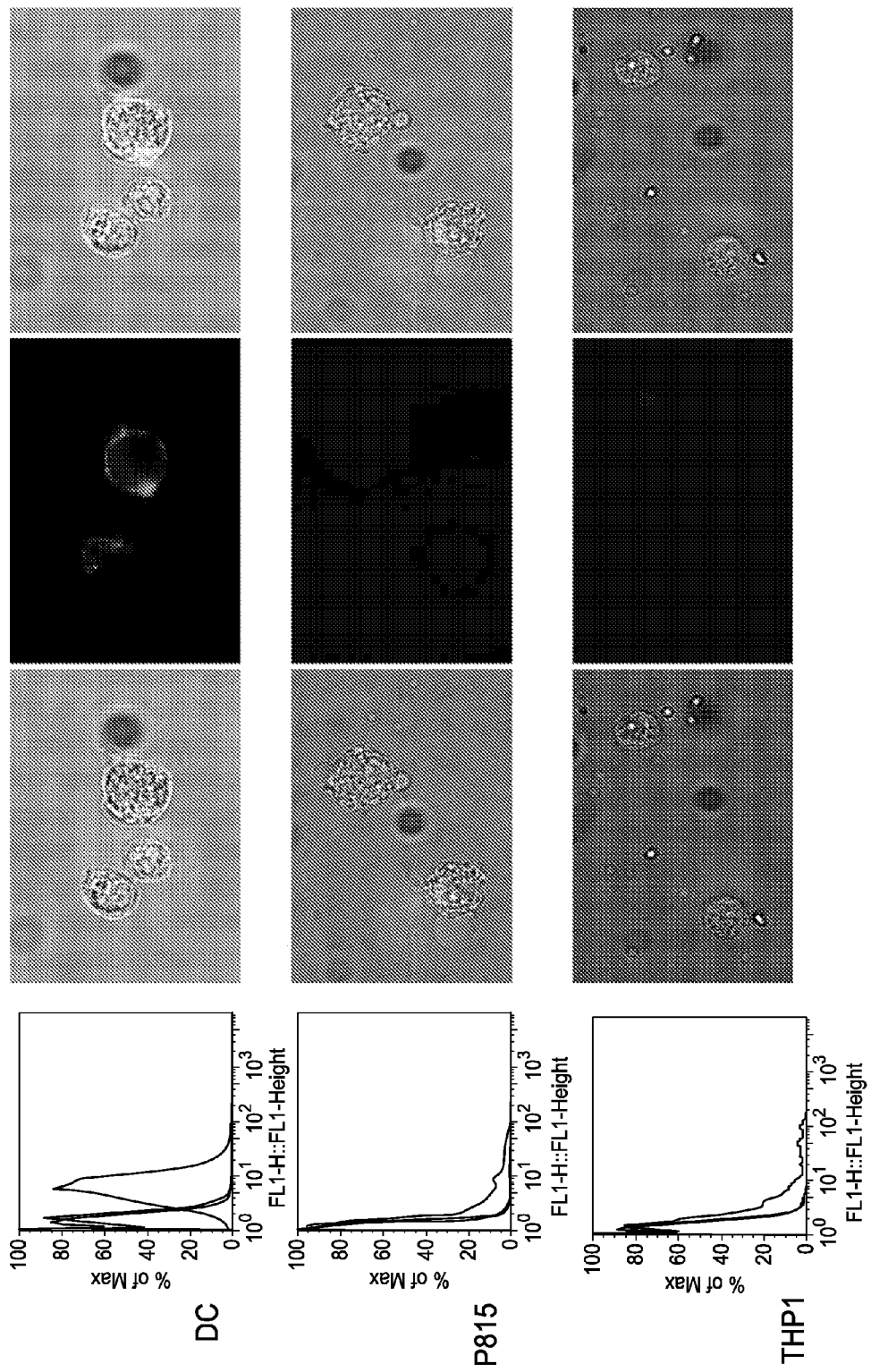
FIG. 50 provides data relating to flow cytometry data and bright field/fluorescence microscopy for cell binding assays of dendritic cell binding DNA nanoparticles. Microscopy images show bright field, fluorescent and overlays from left to right. For flow cytometry data, DNA nanoparticles of both the selected sequence (Clone 3, green) and its reverse complement incorporating Alexa$_{488}$-dCTP were assayed for binding to DCs, P815 and THP1 cell lines. DCs were cultured as described herein. OTHP1 and P815 cells were maintained in RPMI supplemented with 10% FBS and 1% PSG at 37° C. Fluorescent DNA nanoparticles incubated with 5×10$^4$ cells of each respective cell line were aliquoted and resuspended in 50 µL of media (DCs resuspended in their original media). 50 µL of the RCA reaction mix containing synthesized DNA nanoparticles was added directly to each cell line, mixed gently, and incubated on ice for 20 min in the dark. Cells were washed 3 times and formaldehyde fixed to be analyzed by flow and microscopy. Both analyses clearly demonstrate DC specificity as well as specificity for the selected sequence over its reverse complement.

Individual population members were cloned, sequenced, regenerated as fluorescent particles, and similarly tested for binding by flow cytometry. Several clones were found to bind to DCs more than an irrelevant particle control with some of them demonstrating similar binding patterns. The multivalent binding nature of these nanoparticles may lend them the ability to bind a pattern of surface markers on a cell surface rather than a single target. In the four clones tested in FIG. 3, there is definitive homology in the binding characteristics of Clones 3 and 4 that differs significantly from Clones 10 and 12. It is possible that subpopulations of nanoparticles have been selected that bind to unique but distinctive cell surface patterns. It is also interesting to note that even among clones that exhibited similar binding patterns by flow, there was no obvious primary sequence homology. The shape space of such long concatemers is enormous and it likely that even divergent primary sequences may accommodate similar cell surface targets. Consequently, a single clone (Clone 3; SEQ ID NO:01) (5'-GCGCGGTACATTTGCTGGACTATGCAT-GTTCGTAGTTATATAGGGGGATTGTT TGATAGTCG-GAACCGCTGTGCTCAAAGTTTGGAGGT-TGGGGATTTGATGTTG-3') was pursued for additional validation (primer sites underlined). Particles with the sequence of Clone 3 were independently generated from a synthetic oligonucleotide template for all subsequent experiments. A control particle made from the reverse complement of the Clone 3 template was also produced. While the selection scheme used did not include a subtractive or counter-selective step to exclude generic cell binding, the selected DNA nanoparticles bound only to DCs and not to human THP1 (acute monocytic leukemia) and mouse P815 (mastocytoma) cell lines (FIG. 50).

Both flow cytometry and fluorescent microscopy supported the conclusion that the selected particles bind to DCs specifically while the reverse complement control particle did not. Other cell types tested including K562 (chronic myelogenous leukemia) and primary CLL cells (chronic lymphocytic leukemia) also showed no difference between control and selected nanoparticles (data not shown). Cell binding could be completely abrogated by incubation of the nanoparticles with oligonucleotides that hybridize to the selected random regions, though hybridizing a smaller oligonucleotide to the flanking sequence did not affect the DC binding (data not shown). This suggests that the binding is a consequence of the single stranded nature of the particle, presumably due to specific secondary structure. It is important to note that the DC specificity that we observed was an inadvertent result that cannot be assumed in most positive selection mechanisms. Both the power and weakness of random library selections against complex targets such as cells is that the binding target need not be known in advance so there is no reason to believe that any selected ligand would bind a target unique to a particular cell type. However, subtractive or counter-selective screens against non-specific cell types can be used if necessary to enrich for cell specificity.

An important component of many biological nanoparticle applications for in vivo use is the ability to selectively target the desired cells or tissue. Monoclonal antibodies are the primary tool for biomolecular recognition both experimentally and in vivo. However, the general immunogenicity of non-human antibodies and the immune clearance of nanoparticle aggregated humanized antibodies raise concerns about this approach with nanoparticles. As a result, many nanoparticle applications have turned to molecular selection of aptamers and peptides for targeting ligands in place of antibodies. However, since each of these methods produces a small affinity ligand, the transition to a multivalent platform is commonly performed by the relatively crude method of simply attaching several monomers to a common surface, assuming the coupling can be performed without losing the binding activity of each monomer ligand. A potential problem with this approach is that weak non-specific binding can gain sufficient avidity to dilute the desired specificity. In contrast, because DNA nanoparticles described herein are composed of concatemeric repeats of a sequence they offer a native multivalent platform in a single particle that allows us to perform a selection on whole particles in the same context of ultimate usage.

DNA has a unique complement of overlapping biochemical, structural, and functional activities when compared to other polymers typically used in nanoparticle synthesis. DNA motifs can act as ligands to specific biomolecules, DNA can be immunogenic if it contains unmethylated CpG motifs, it can act as a scaffold for hybridizing other oligonucleotide conjugates, it can have enzymatic activity, it is easily chemically modified to allow small molecule or metal ion attachment and metals can be directly deposited onto DNA for imagining, and it can carry DNA binding drugs (Klinman, D. M. Adjuvant activity of CpG oligodeoxynucleotides. Int. Rev. Immunol. 25, 135-154 (2006); Breaker, R. R. & Joyce, G. F. A DNA enzyme that cleaves RNA. Chem. Biol. 1, 223-229 (1994); Berti, L., Alessandrini, A. & Facci, P. DNA-Templated Photoinduced Silver Deposition J. Am. Chem. Soc 127, 11216-11217 (2005)). DNA has a long clinical history and a favorable toxicity and biodegradability profile (Fichou, Y. & Ferec, C. The potential of oligonucleotides for therapeutic applications. Trends Biotechnol 24, 563-570 (2006)). Cell specific DNA nanoparticles are a potential affinity reagent for research work and are an attractive platform for targeted imaging or therapeutic applications.

Example 14 ssDNA-Nanoparticles as Molecular Marker for Detection of Cancer Cells

Cancer cells have molecular alterations that can be used for their identification at early stages of the disease. ssDNA-nanoparticles are designed able to bind to these cell alterations. These particles can be created by rolling cycle amplification (RCA) from a template DNA. Different DNA templates can be combined together to create a multivalent DNA nanoparticle able to recognize more than one alteration. Starting from a random DNA-library, MDAMB-231 cells (epithelial breast cancer cell) were incubated with DNA-sequences for several biopanning cycles to enrich the binding sequences. After donning and sequencing of the motifs, these were incubated with 3 different cell lines (2 breast cancer cell lines, MDA-MB-231 and MCF-7, and one monocytic cell line, THP-1) to test the specificity of the ssDNA-nanoparticles. Forty clones have been analyzed and at least 2 of them are candidates for specific binding to MDA-MB-231. These methods and ssDNA nanoparticles are useful in breast cancer and other types of cancers, for example, lung, pancreatic, brain. The ssDNA nanoparticles contribute to the development of new tumor markers and help to consolidate the use of a new technology, Nano-technology, for diagnosis of cancer.

Figure 51:
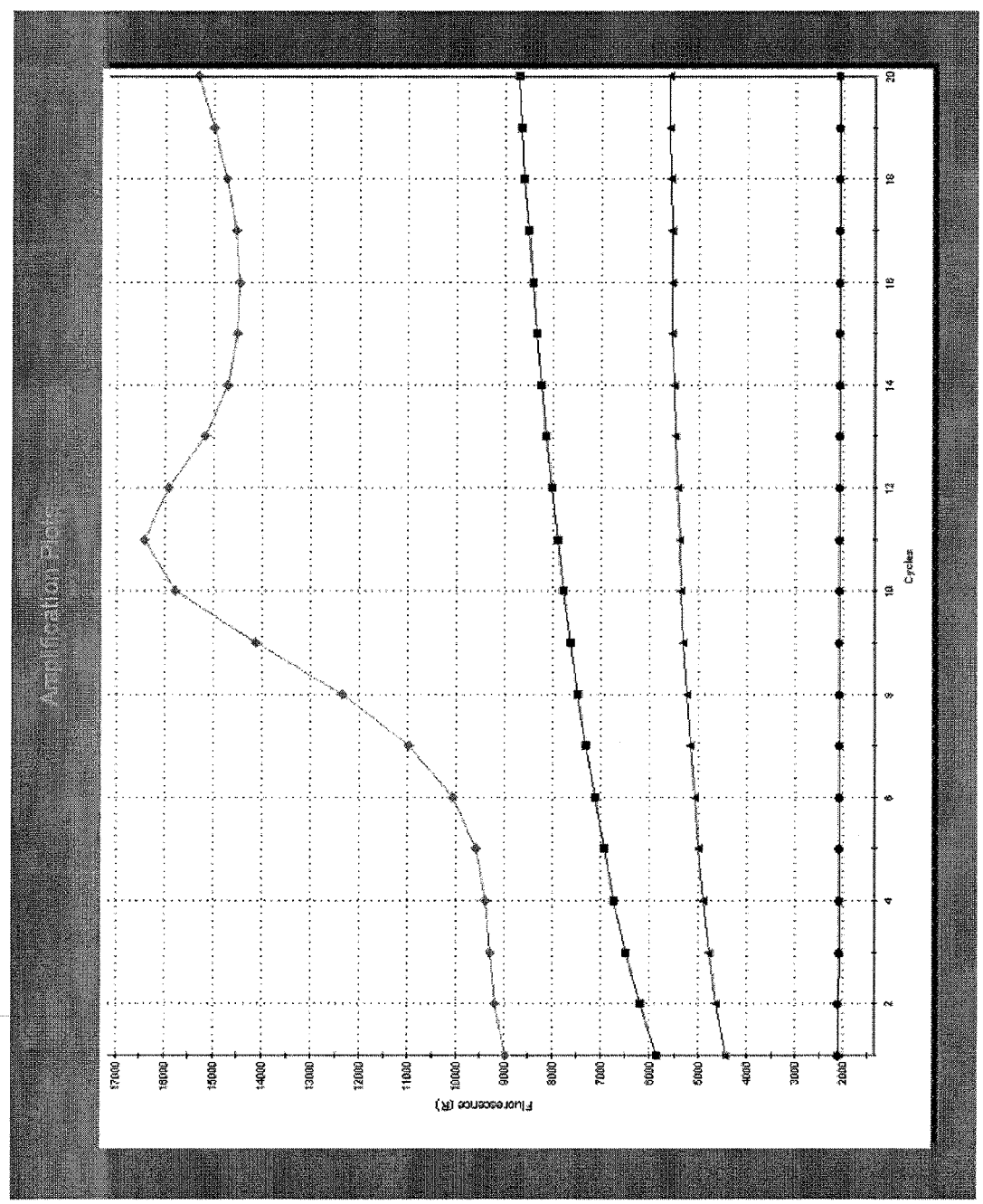
FIG. 51 relates to the generation of ssDNA nano-particles: ♦ (upper line): cells+qPCR+RCA; ■: cells+qPCR reagent; ▲: cells+qPCR+RCA(−); ♦ (lower line): cells. A graph of fluorescence (R) vs. number of cycles. Eight bio-panning cycles have been made starting from a random DNA-library. In each bio-panning cycle, MDA-MB-231 cells (epithelial breast cancer cells) were incubated with ssDNA nanoparticles and the binding particles were amplified by qPCR. The goal of each cycle was to enrich and amplified the binding motifs.

FIG. 51. Generation of ssDNA nano-particles: ♦ (upper line): cells+qPCR+RCA; ■: cells+qPCR reagent; ▲: cells+qPCR+RCA(−); ♦ (lower line): cells. A graph of fluorescence (R) vs. number of cycles. Eight bio-panning cycles have been made starting from a random DNA-library. In each bio-panning cycle, MDA-MB-231 cells (epithelial breast cancer cells) were incubated with ssDNA nanoparticles and the binding particles were amplified by qPCR. The goal of each cycle was to enrich and amplified the binding motifs.

Figure 52:
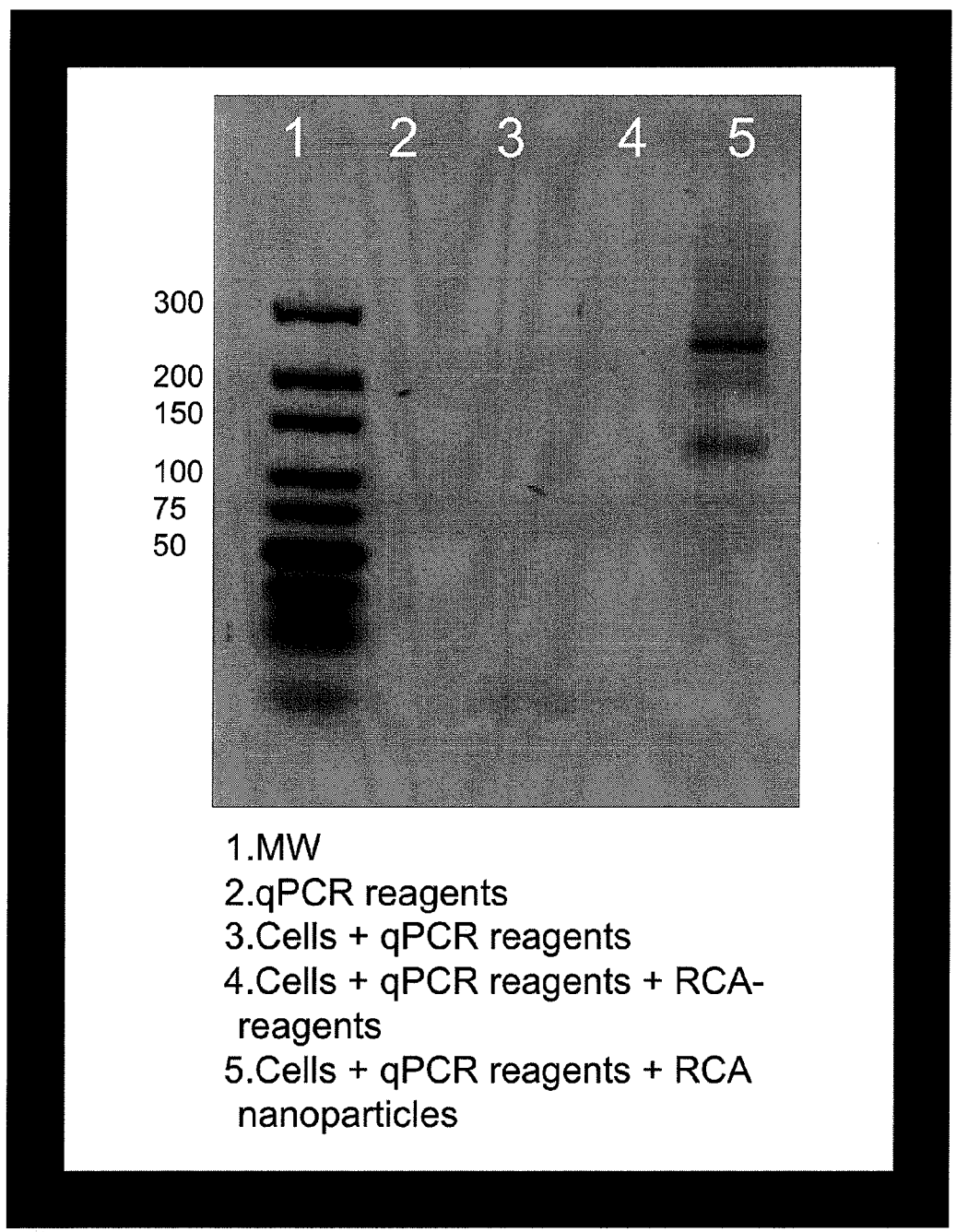
FIG. 52 relates to DNA gel of amplified sequences: After each bio-panning cycle, the amplified samples were run in a DNA gel where the amplified products can be visualized. In all the bio-panning cycles, amplified products were observed only from the samples corresponding to cells+RCA particles (lane 5). No amplification of cell DNA was observed (lane 2, 3 and 4). Line 1 represents the molecular weight ladder.

FIG. 52. DNA gel of amplified sequences: After each bio-panning cycle, the amplified samples were run in a DNA gel where the amplified products can be visualized. In all the bio-panning cycles, amplified products were observed only from the samples corresponding to cells+RCA particles (lane 5). No amplification of cell DNA was observed (lane 2, 3 and 4). Line 1 represents the molecular weight ladder.

Figure 53A:
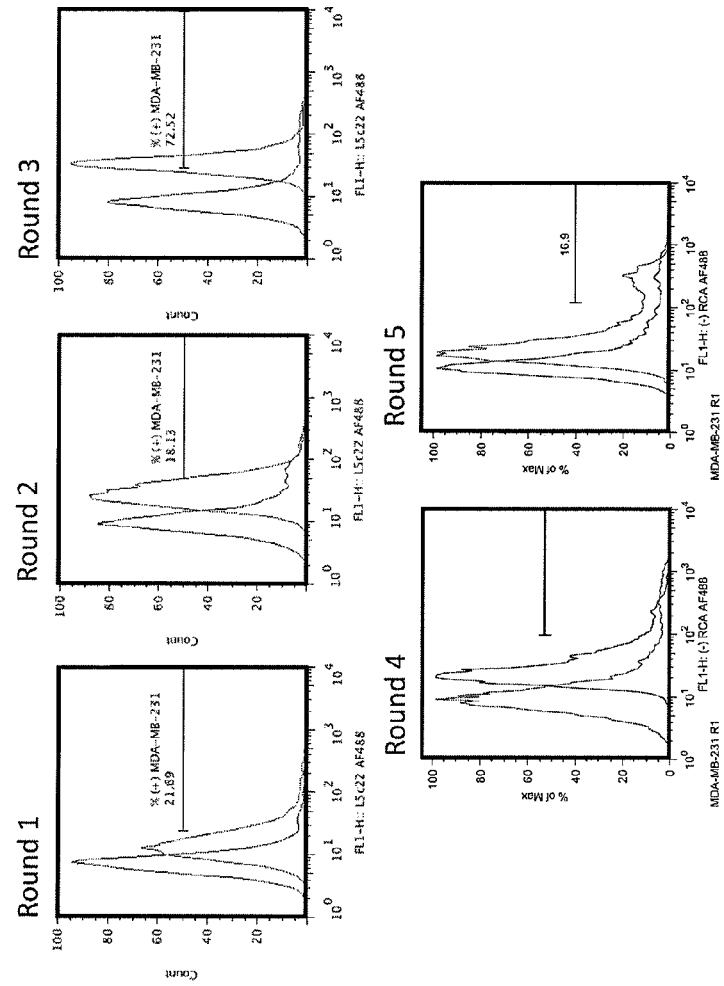
FIGS. 53A-53C show graphs including FACS analysis to test the binding and specificity of ss-DNA nanoparticles. ss-DNA nanoparticles were generated by RCA and incubated with the epithelial breast cancer cells, MDA-MB-231.
Figure 53B:
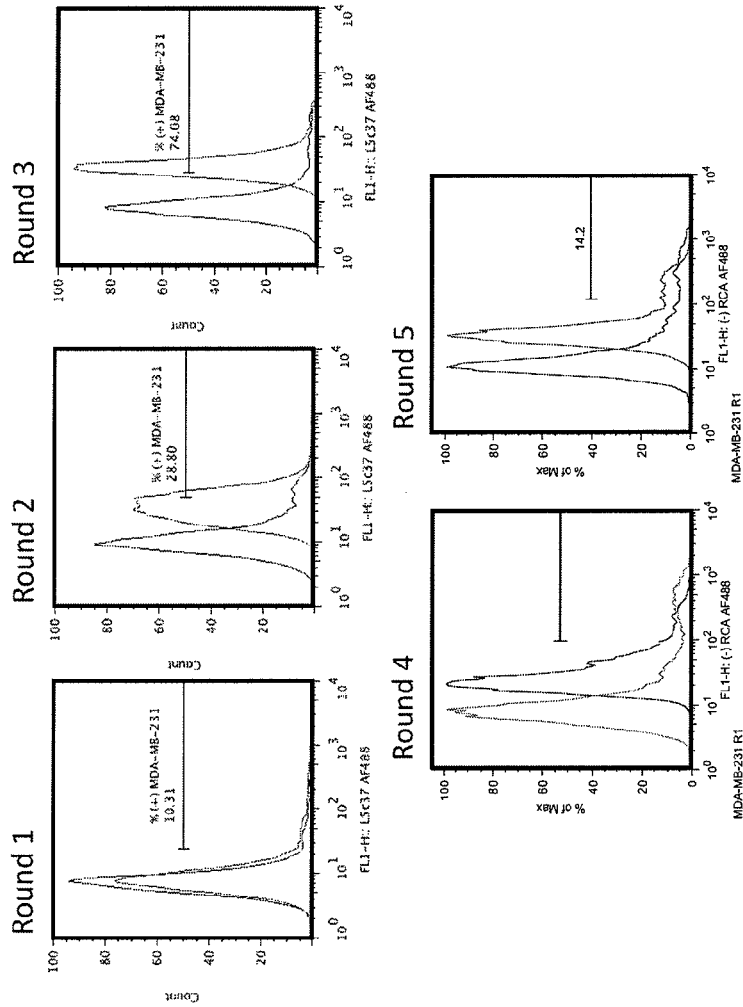
Figure 53C:
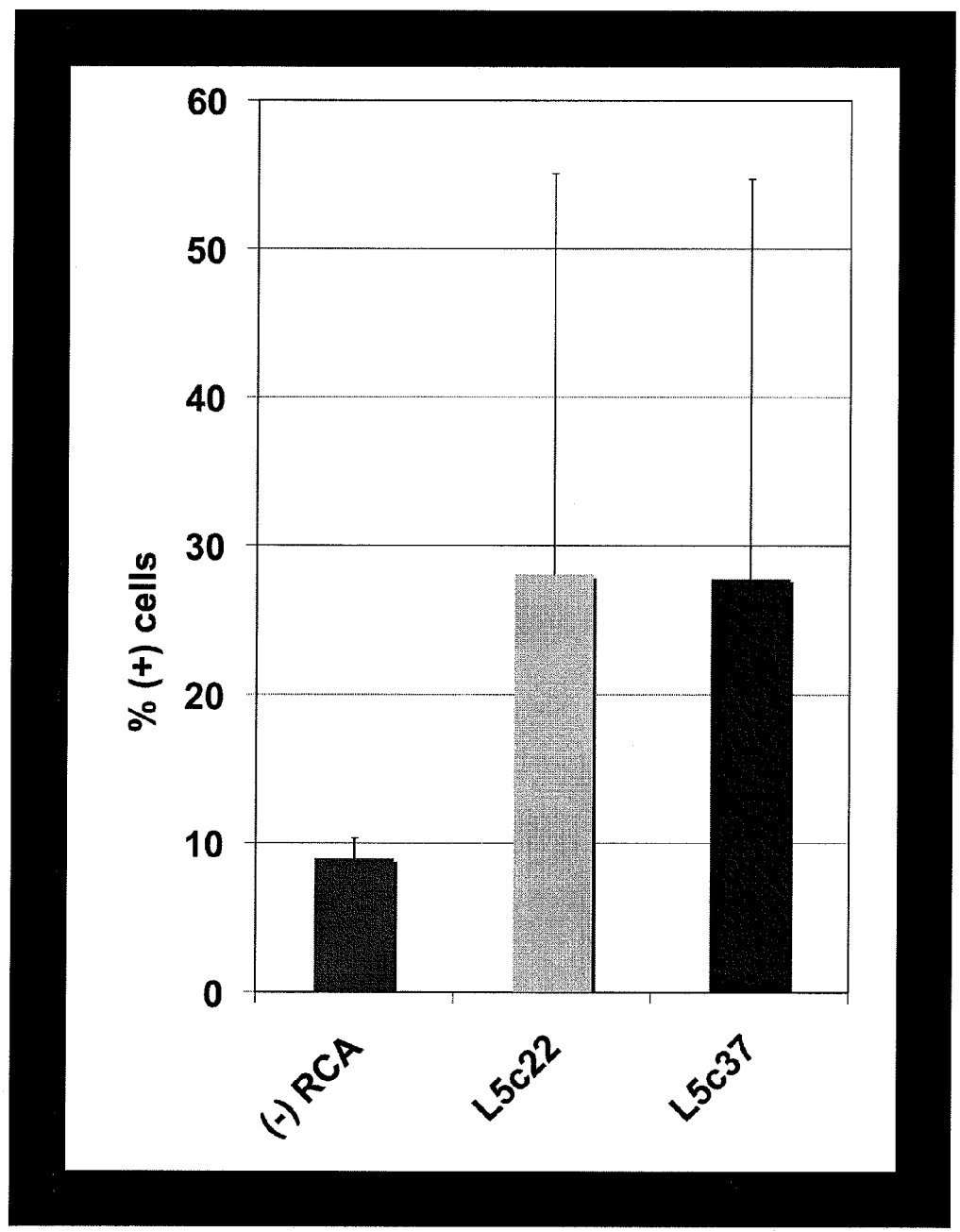
Figure 54A:
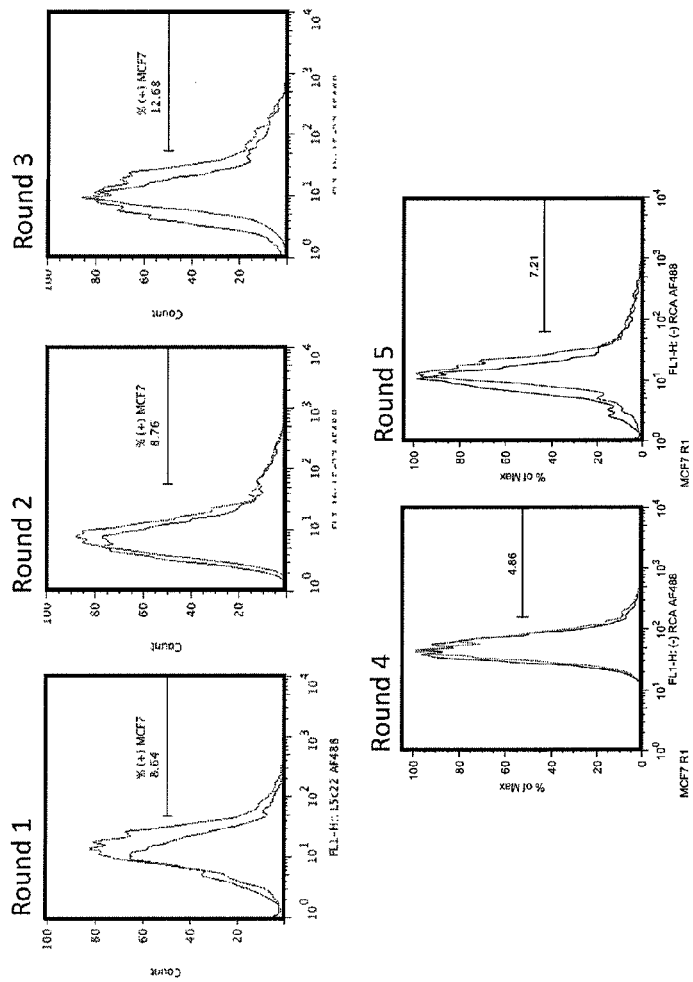
FIGS. 54A-54C shows graphs including FACS analysis to test the binding and specificity of ss-DNA nanoparticles. ss-DNA nanoparticles were generated by RCA and incubated with the epithelial breast cancer cells, MCF-7.
Figure 54B:
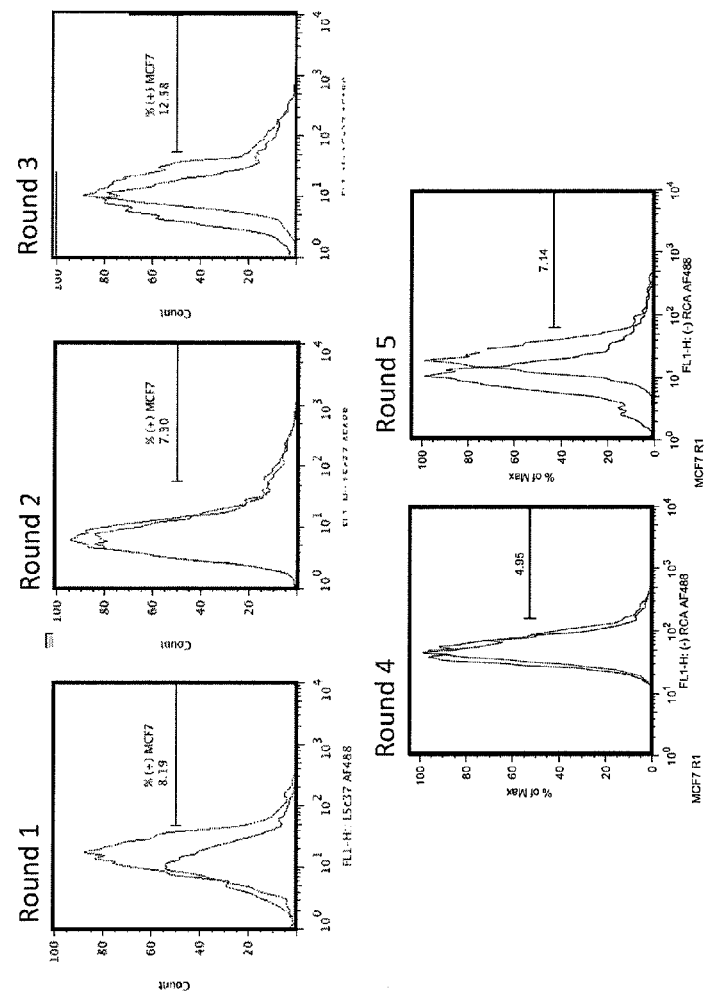
Figure 54C:
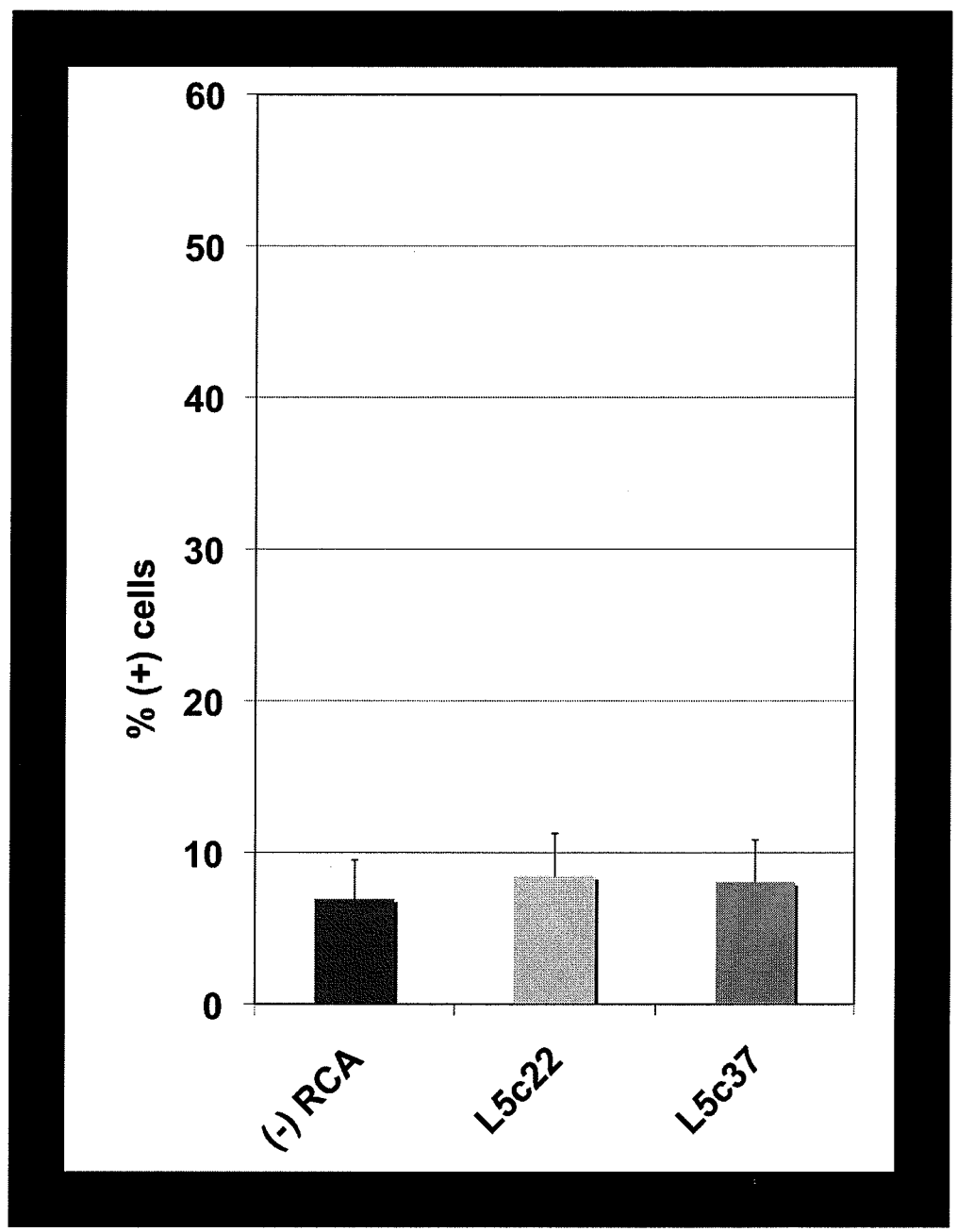
Figure 55A:
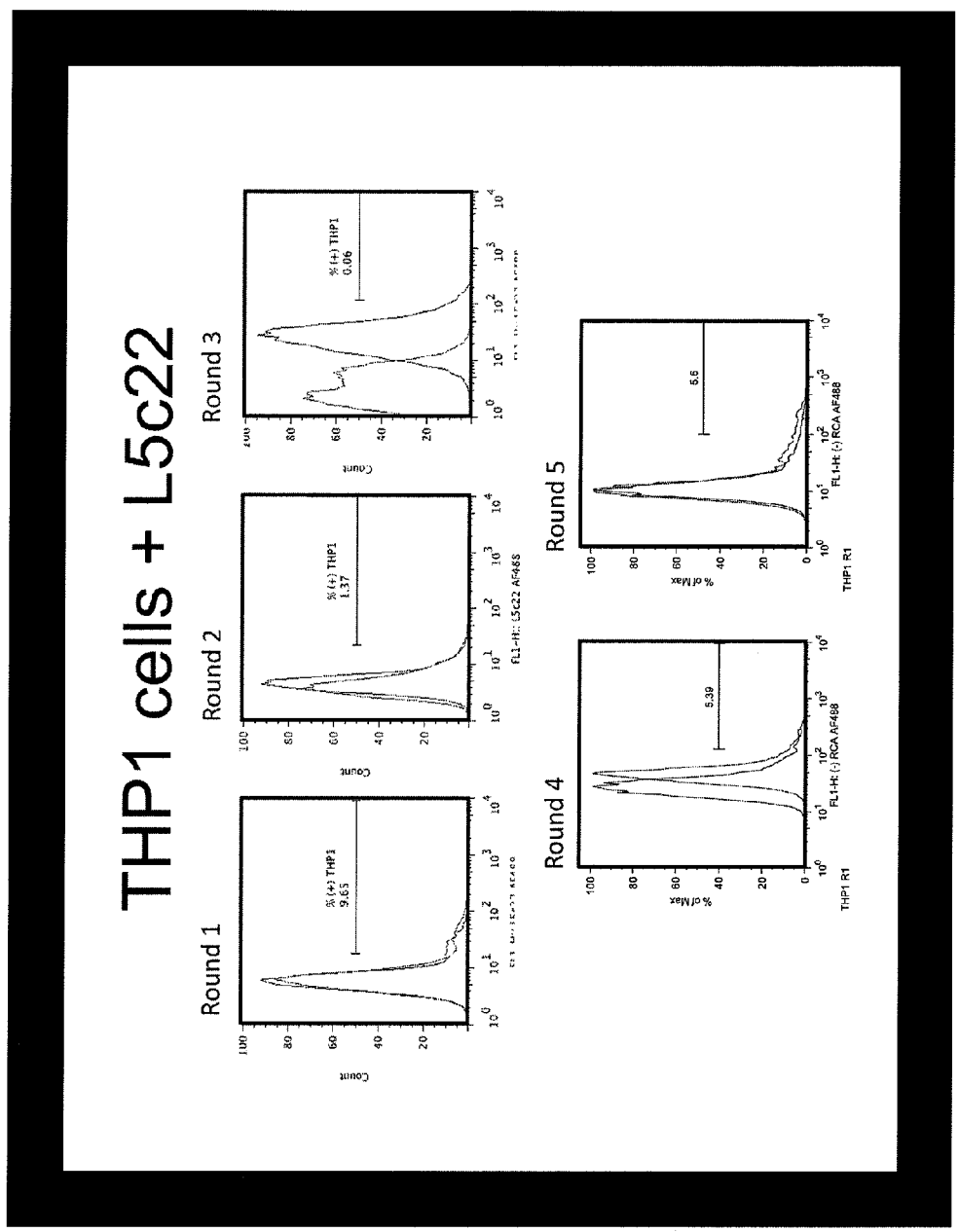
FIGS. 55A-55C show graphs including FACS analysis to test the binding and specificity of ss-DNA nanoparticles. ss-DNA nanoparticles were generated by RCA and incubated with the monocytic cell line, THP-1.
Figure 55B:
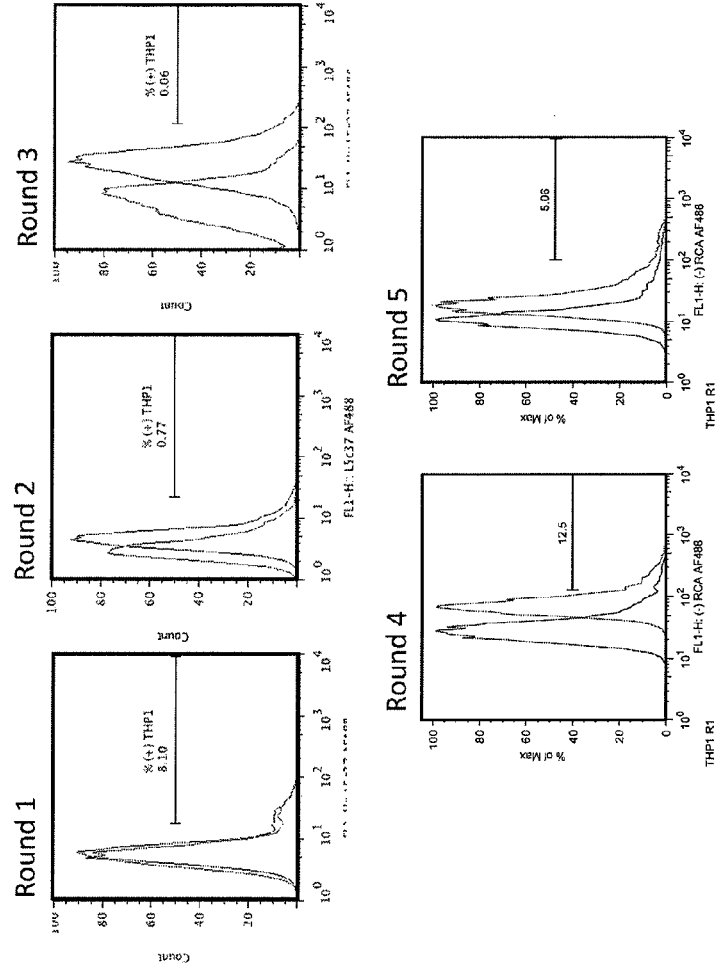
Figure 55C:
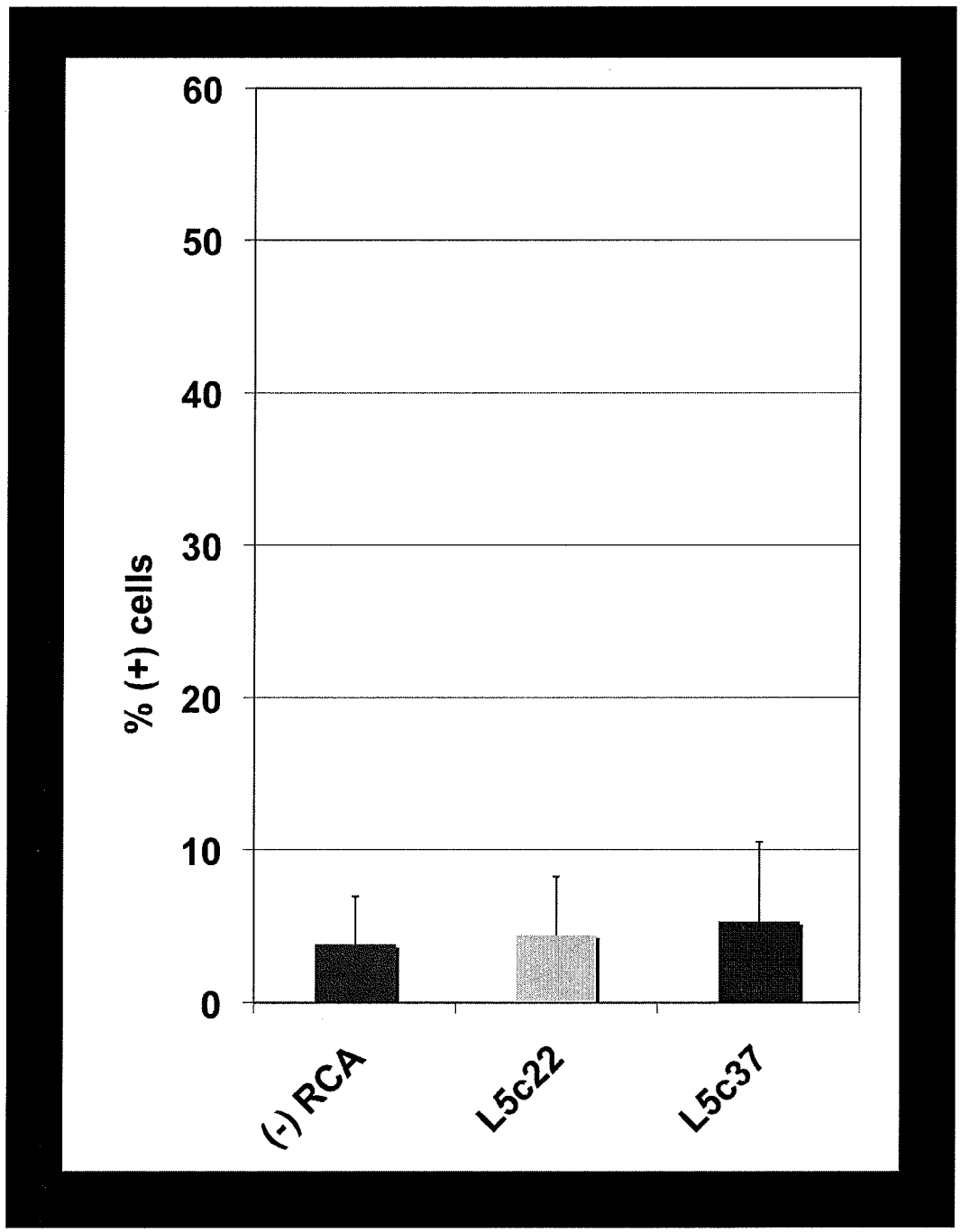

FACS analysis of the binding ss-DNA nanoparticles to test specificity of the particles are shown in FIGS. 53-55. ss-DNA nanoparticles were generated by RCA and incubated with 3 different cell lines: Two epithelial breast cancer cells, MDA-MB-231 (FIGS. 53A-53C) and MCF-7 (FIGS. 54A-54C), and a monocytic cell line, THP-1 (FIGS. 55A-55C). This test was repeated five times. Of 40 clones analyzed, 2 of them, L5C22 and L5c37, were specific for MDA-MB-231 cells as is shown in the FACS plots (blue line, background ((−)RCA); red line, specific signal). The last column represents the average of the results of five experiments.

Example 15

Bi-Specific DNA-Nanoparticles

Figure 56:
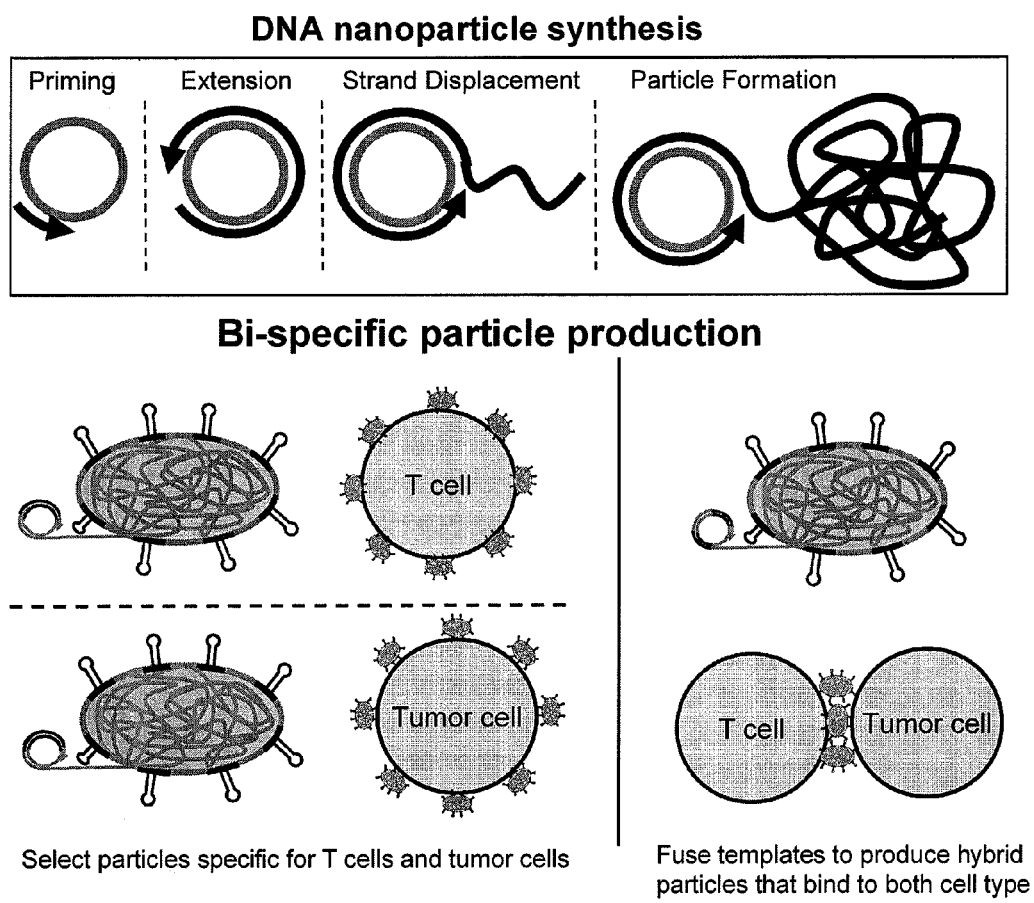
FIG. 56 shows a general example scheme for the production bi-specific DNA-nanoparticles (NP) that bind to both tumor cells and T cells.

This example illustrates the production bi-specific DNA-nanoparticles (NP) that bind to both tumor cells and T cells. Binding particles that bind the pancreatic tumor cell line, panc02, are used as the tumor binding moiety. In this example, T cell binding DNA-NP are selected using a DNA-NP library technique to identify DNA-NP that bind to mouse and human T cells. Each moiety is selected against separately. Construct and validate Hybrid particle that bind to T cells and pancreatic cancer cells are constructed and validated. In addition, the effects of bi-specific DNA-NP on tumor growth and metastasis are evaluated. The scheme is summarized in FIG. 56.

DNA-NP differ from other affinity reagents in several ways. Each particle contains many copies of the sequence elements so there is intrinsic multivalent display of the modules, allowing avidity to compensate for low monovalent affinity. Molecular modeling suggests that the repeating units that make up a particle can adopt more complex secondary structures than simply repeating the predicted structure of the monomer. The modular nature of the particle template construction allows multiple distinct recognition elements to be assembled into a single molecular entity. Furthermore, the selection method allows the optimal particle to be evolved in the same molecular context in which it will be used, rather than transplanting them to some other framework or particle for application.

DNA-NP are produced using methods described herein. Briefly, DNA-NP are produced by enzymatic DNA synthesis using a strand displacing DNA polymerase, phi29, and a circular oligonucleotide template. The resulting RCA products are concatemers complementary to the template circular oligonucleotide. These long single stranded products collapse into randomly coiled nanoparticles. DNA-NP can be readily analyzed by Dynamic Light Scattering (DLS) and a low polydispersity index. A typical 30 minute reaction produces particles ~250 nm in size, with an estimated DNA length of ~30 kb.

DNA nanoparticle libraries are constructed using methods described here. A general scheme is shown in FIG. 7. Particles that bind to human breast cancer cell line MDA-MB-231 and mouse pancreatic cell line panc02 have been selected. In each case, enrichment of cell binding particles was observed after 4 rounds of selection and clones taken from the 6th round were shown to have cell line specific binding. Strikingly, a clearly sequence motif was apparent among the clones that bound to panc02. The particles do not bind to several other epithelial derived cell lines tested.

Figure 57A:
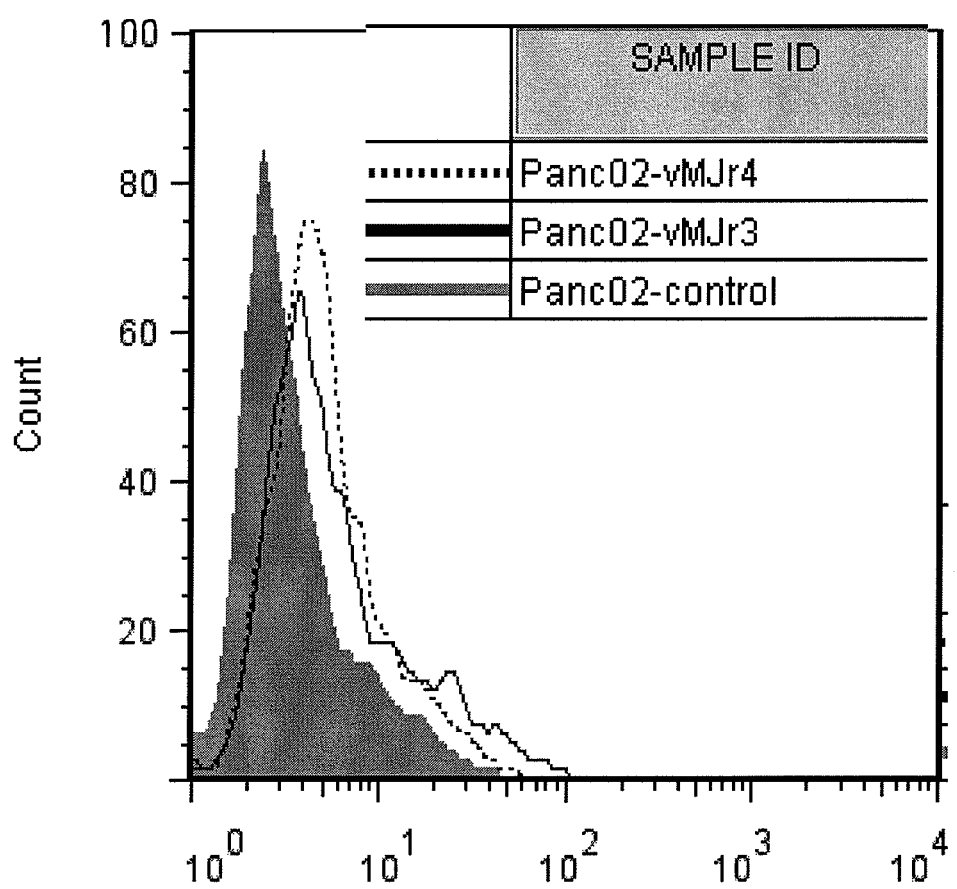
FIGS. 57A and 57B summarize the results of the selection of pancreatic cancer cell line panc02 targeting particles. The mouse pancreatic lines panc02 was panned with a single module DNA nanoparticle library. After the $3^{rd}$ and $4^{th}$ round, the selected pool was fluorescently labeled and tested on the target cells by flow cytometry (FIG. 57A). The clones that contain the AATGGGGCG (SEQ ID NO:12) motif bind specifically to panc02, whereas the clones lacking the motif (C21 and C50) do not (FIG. 57B). In the experiment shown, the four clones that show a fluorescent shift in the left panel all contain the motif whereas the clones without the motif are no better than controls. No difference is seen against other epithelial cell lines.
Figure 57B:
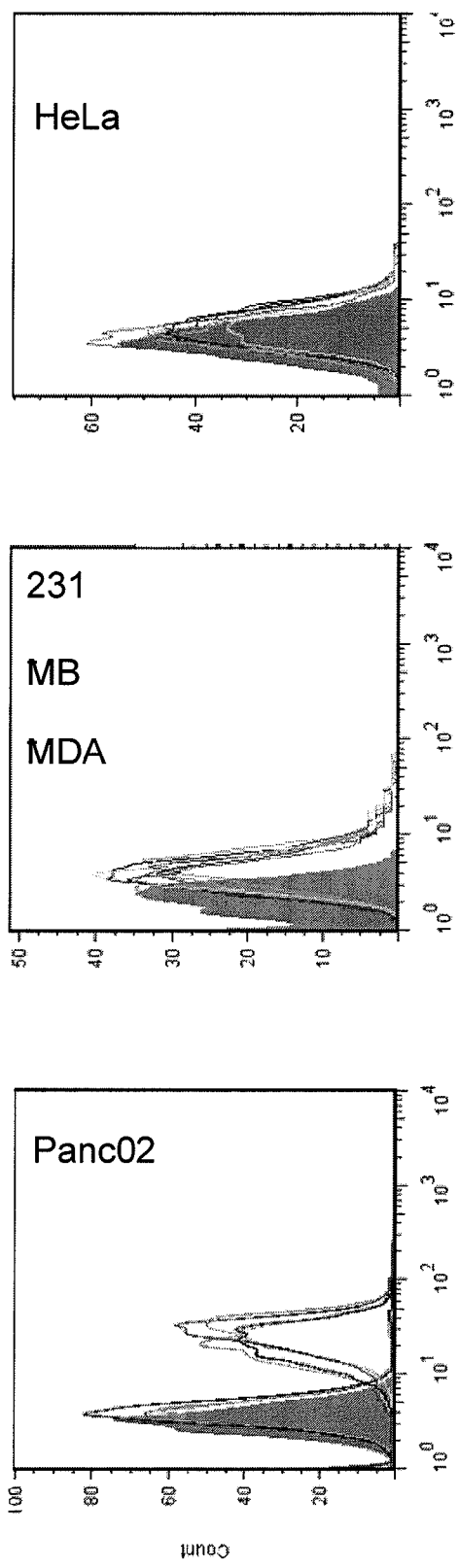
Figure 58:
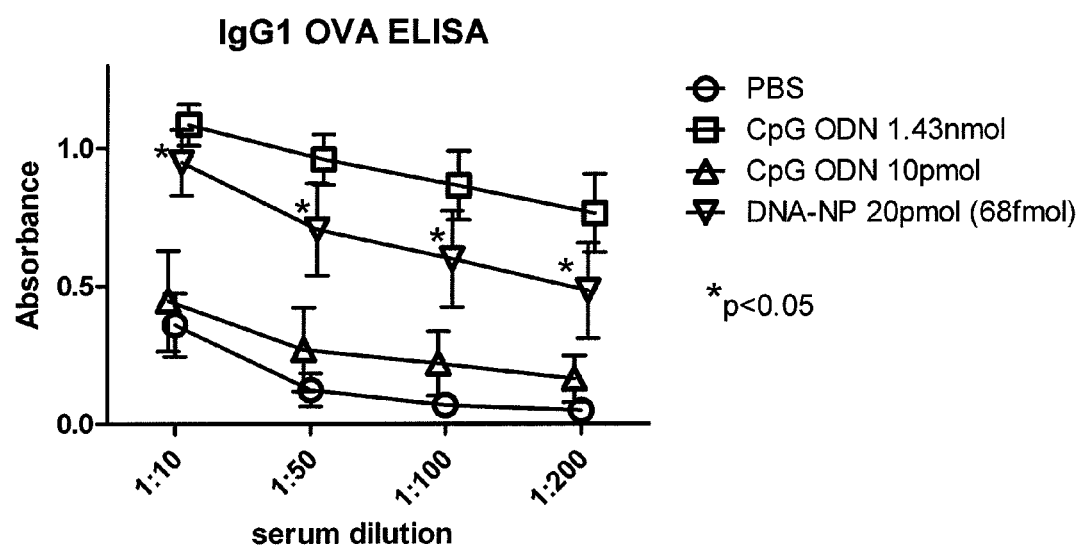
FIG. 58 provides data relating to an ELISA experiment. Mice immunized with DC binding DNA-NP, or CpG oligonucleotides (ODN).

FIGS. 57A and 57B summarizes the results of the selection of pancreatic cancer cell line panc02 targeting particles. The mouse pancreatic lines panc02 was panned with a single module DNA nanoparticle library. After the 3$^{rd}$ and 4$^{th}$ round, the selected pool was fluorescently labeled and tested on the target cells by flow cytometry (FIG. 57A). A shift indicating enrichment of binding clones was observed. After the 5$^{th}$ and 6$^{th}$ round, clones were generated from the selected pool and sequenced (TABLE 6). 10 of the 12 sequenced clones contained a specific sequence motif: AATGGGGCG (SEQ ID NO:12). In two of the clones the motif appears in the same frame (C45 and C58). Two independent clones for each we recovered with the sequence of clone 40 and 46.

TABLE 6

| Clone | Sequence | SEQ ID NO: |
|---|---|---|
| C33 | TGCTTTTTGGAACTCCTGCTAGATGATGGAATATCAAGGCT GATTAAACGGGGCGTTTCCTGAAATGTATTACTTGTTGAGG TGACGTTGAGTTGGATCC | 02 |
| C39 | TGCTTTTTGGAACTCCTGCTTAGCAGTAAGAAAGTACAATG GGGCGATAACCCCAATCATGACTAAAAATATGATTCGGAGG TGACGTTGAGTTGGATCC | 03 |
| C40 | TGCTTTTTGGAACTCCTGCTAAACAAAAGAGGATTGTATGG GGCGTATCAGTTCGACTATCTGGTAGAGCAAAGAAAAGTGG TGACGTTGAGTTGGATCC | 04 |
| C43 | TGCTTTTTGGAACTCCTGCTAACCGGAAGTTCGTATGGCCA AAGCTGATTAAAACGGGGCGTTTACACAAGGTGTATGTGGG TGACGTTGAGTTGGATCC | 05 |
| C44 | TGCTTTTTGGAACTCCTGCTATAGCTGAAGGATATTGGATC GGGGTTGGATTTACGATTTAGATTTGTTATGTTCTCTTGGG TGACGTTGAGTTGGATCCGGTGACGTTGAGTTGGATCC | 06 |
| C45 | TGCTTTTTGGAACTCCTGCTGAATAGAGAACAACTAAATTC TGCAATGATGTTGCGTAGTGACTAANGATCAAATGGGGCGG TGACGTTGAGTTGGATCC | 07 |
| C46 | TGCTTTTTGGAACTCCTGCTGATCAGGTTATAAAGCGTTAA TAGCTTAATAAAACTTGAAAGGTAATAAATGGGGCGTCTGG TGACGTTGAGTTGGATCC | 08 |
| C58 | TGCTTTTTGGAACTCCTGCTAAAGAGTACGAGGTAGAAATA TGAGAAACTTTAAATTTGTCCAGCAGATCCTAATGGGGCGG TGACGTTGAGTTGGATCC | 09 |
| C21 | TGCTTTTTGGAACTCCTGCTAGACGTTAGATGTATCTGACC TTACGACTTCAACTTCCTTCTAAATCTGCCCACAACGATGG TGACGTTGAGTTGGATCC | 10 |
| C50 | TGCTTTTTGGAACTCCTGCTCAACTTGTGTCCTCTTGAAAG AGTCGGTCATACCTATAAGAATACTTTTATACAGCCAAAGG TGACGTTGAGTTGGATCC | 11 |

The clones that contain the AATGGGGCG (SEQ ID NO: 12) motif bind specifically to panc02, whereas the clones lacking the motif (C21 and C50) do not (FIG. 57B). In the experiment shown, the four clones that show a fluorescent shift in the left panel all contain the motif whereas the clones without the motif are no better than controls. No difference is seen against other epithelial cell lines.

Selecting for T Cell Binding DNA-NP

DNA-NP that bind to an implantable mouse tumor cell line (panc02) are used. Therefore, DNA-NP that bind the T-cell binding motif also, are selected. Three approaches are used. (1) Primary mouse T cells obtained from PBMCs by negative selection are screened. Binding particles are checked for binding to human T cells. (2) A mixture of human and mouse T cells is screened, with the notion that a crossreactive particles would have a selective advantage during the screening. Candidate particles are checked against both mouse and human T cells. (3) Alternate mouse and human will be alternated in each round of screening.

Once a particular screening is performed for 6-8 cycles, the pool of particles present at that stage is analyzed by incorporating fluorescent nucleotides and checking the binding by flow cytometry. If the population looks like it has enriched for binding, individual candidate particles are recovered by subcloning the PCR amplified templates into bacteria. Candidates are sequenced and regenerated by asymmetric PCR/RCA for further testing as particles. The specificity of binding clones is analyzed by incubating the particles with PBMCs and anti-CD3 antibodies. The particle fluorescence should be confined to the CD3+ population.

Construct and Validate Hybrid Particle that Bind to T Cells and Pancreatic Cancer Cell.

The templates for the T cell and panc02 binding motifs are ligated together. Adding an additional module to a cell binding particle does not significantly reduce the cell binding. At least five unique combinations of panc02 and T cell binding motifs are produced and tested for binding to both cell types independently by flow cytometry. T-cell/panc02 cell cros slinking is evaluated in several ways. First, varying numbers of particles with an equal mixture of both cell types are incubated together. High concentrations of particles will lead to wholesale crosslinking and essential agglutinate the cells are expected, whereas lower concentrations will form primarily heterocellular dimers. The former is evaluated by microscopy and the later by flow cytometry using differently labeled anti-CD3 and anti-EpCAM antibodies to distinguish hetero and homocellular aggregates.

In addition, direct cell lysis during co-culture of the panc02 with T cells from the same mouse strain (C57BL/6) from which the line was derived, using either LDH or chromium release assays is evaluated. The stoicheometry of particle to target cells is optimized by titrating the particles and the relative number of cells, and the time course for cell lysis determined. In addition, the effect, if any, of particle size is evaluated, by producing particles of ~50, 100, and 200 nm as measured by dynamic light scattering. With this panel of assays, which hybrid DNA-NP combinations are most potent is determined.

Evaluate the Effects of Bi-specific DNA-NP on Tumor Growth and Metastasis.

Hybrid particles are analyzed for circulating half-life in normal mice, as a function of particle size. In addition, particle accumulation in liver, spleen, and lymph nodes are measured. In all cases, the particles can be easily quantitated by real-time PCR, with the same primers used to amplify the particles during the selection. Indeed, since each particle consists of many copies of the repeated sequence, single particle sensitive is achievable. Some of these methods allow the de-selection of any particle that has exceptionally rapid clearance, and establish the optimal size for subsequent tumor studies.

Example 16

Targeting Dendritic Cells with DNA-Nanoparticles

Dendritic cell (DC)-based immune therapy for cancer has met with some success using ex vivo approaches of injecting antigen-pulsed mature DCs into patients. However, in vitro generation of DCs is costly, cumbersome, and difficult to standardize. Thus, activation of DCs in situ is an attractive approach but requires agents that can both specifically target and activate DC. DNA-NP library technology is described herein that can select cell specific binding NP made solely of single stranded DNA. Using such techenology, DNA-NP have been identified that bind specifically to DCs, are taken up, induce $Ca^{2+}$ flux, and IL-6 secretion by DCs, and can act as vaccine adjuvants in mice. These results show a DC targeting molecule that also carries intrinsic adjuvant properties. This example illustrates targeted DNA-NPs that bind to and stimulate DCs, and cause immune activation and prevent or retard tumor growth.

Production, Characterization, and Purification of DNA Nanoparticles

DNA nanoparticles were produced by methods described herein. High diversity libraries of DNA-NP were generated using methods described herein, and DNA-NP that bind specifically to DCs were selected through an iterative screening and re-amplification.

DC binding DNA-NP was verified using separate batches of particles and synthesizing particles from both the original clone (PCR from bacteria colonies harboring the clone, followed by asymmetric PCR with a 5' phosphate on only the desired primer for subsequent strand ligation and rolling circle amplification (RCA) or from a synthetic oligonucleotide template with the same sequence. The stability of particles kept at −20° C. and 4° C. for several weeks; no loss of activity was observed.

DC Binding DNA-NP Activate DC

DC binding DNA-NP cause DC activation as measured by cytokine secretion, and $Ca^{2+}$ signaling, and surface marker expression. IL-6 secretion is a commonly used indicator that DC have matured into immune activating cells, though a full cytokine secretion profile is ultimately desirable to confirm this point. DCs exposed to several of the DC binding DNA-NPs secrete IL-6, IL-12, and TNF-alpha. In addition, $Ca^{2+}$ flux 20 seconds after DC were exposed to DC binding DNA NP was detected, but not after exposure to control DNA-NP.

An immunization study was carried out in which DNA-NP were mixed with ovalbumin and injected s.c. into mice, boosted two weeks later, and analyzed a week after the final boost for antibody responses by serum IgG titers. Robust antibody responses were seen in all mice immunized with DC binding DNA-NP even though the dose is much lower than typical immunization protocols with CpG oligonucleotides (ODN) (FIG. 57). Since our particles are single molecules made up of contameric repeats (n=~300) of the complement of the template circle from which they are produced, the dose can be expressed as either the number of particles (68 fmol), or as the number of complement repeats (20 pmol).

Screening DNA-NP that Activate DC

Five 5 DNA-NP that bind to DC were identified. All 5 DC binding DNA-NPs are compared for their ability to activate myeloid (CD11c+) bone marrow-derived DCs (BM-DCs) in vitro, as these are known to function similarly to human monocyte-derived DCs. BM-DCs will be generated (Telusma G, et al. Dendritic cell activating peptides induce distinct cytokine profiles. Int Immunol. 2006; 18:1563-1573). DC activation and maturation is characterized by altered surface expression of characteristic molecules, production of large amounts of cytokines and enhanced T cell stimulatory capacity. DC stimulatory capacity of the DC-binding DNA-NPs is evaluated in three ways: 1) their ability to alter the expression of surface molecules on immature DCs that are classically up or down regulated upon maturation; 2) their ability to induce secretion of inflammatory cytokines, and finally 3) their ability to mature DCs into effective antigen presenting cells that can activate antigen-specific T cells. The particles are ranked according to their activity in these assays.

In vivo selection of ligands that bind to cells or soluble proteins has been well established, for example, with phage displayed peptide libraries. In vivo selections have two significant advantages. The first is that the selection is being performed in the very same environment that the ultimate product will be used. The second is that the rest of the animal acts as a subtractive substrate that will remove any non-specific particles.

In vivo selections are performed with DNA-NP by injecting the DNA particle library subcutaneously and recovering the draining lymph nodes several hours later. The lymph nodes are treated with collagenase to create single cell suspensions, and the CD11c+ DCs are isolated by magnetic bead separation. Subsequently the particle recovery, re-amplification, and ligation will be as described herein.

Injection of DNA-NP into Tumors to Activate Tumor Infiltrating DC

All in vivo experiments are conducted in a transplantable mouse model of melanoma using the mouse melanoma cell line B16-OVA that expresses chicken ovalbumin (OVA), which serves as a tumor marker to monitor immune responses. When injected s.c. into C57/BL6 mice, B16-OVA produces a local tumor growth.

C57/BL6 mice (n=5 per group) are inoculated with $5 \times 10^5$ B16 cells s.c. Once the tumors reach 3-5 mm in size, they receive intra-tumoral injection of: 50 µl of PBS, DC binding DNA-NP, or a control DNA-NP. DNA-NPs are injected at 1 and 10 µg/ml (~$10^{10}$ and $10^{11}$ particles) suspended in PBS. 24-48 hours later the mice will be sacrificed and the tumor, draining lymph nodes, blood, liver, and spleen are collected. Histology is performed on the tumor and the number of infiltrating lymphocytes compared (CD3+ and CD11c+) to controls. Single cell suspensions are made by treating the tissue with collagenase and tumor infiltrating DCs are analyzed for the expression levels of co-stimulatory and adhesion molecules, e.g. CD80, CD86, MHC class II, CD40, by flow cytometry. The expression of IL-12, IFNγ, TNF-α and RANTES is determined by intracellular staining combined with surface CD11c and analyzed by flow cytometry.

Long term tumor monitoring is performed. Groups of mice (n=5) are inoculated with tumor and injected with DNA-NP or controls. The mice receive 5-10 daily injections of DC-targeting DNA-NPs, control non-targeting DNA-NPs or PBS. Mice are monitored for tumor size a set of calipers: $A \times B^2/2$ (A=long axis, B=short axis) daily until the last injection and then bi-weekly over a period of 20 days. After 20 days or if the tumors reach 1.5 cm in diameter, whichever occurs first, mice are sacrificed. The spleen, liver, and kidney will be weighed and tissue analysis will be performed by our molecular pathology core. If the pilot study indicates potential tumor retardation or regression in the mice that received the DNA-NP without overt toxicity then a larger study will be designed in coordination with the biostatistics core.

Immunization with DNA-NP and Model Tumor Antigens

Co-injection of the most potent DNA-NPs with tumor antigen is likely to lead to the induction of anti-tumor immune response. OVA serves a model tumor antigen for which tool to measure immune responses have been developed and thus allows one to easily monitor the potency and type of induced immune response.

Immunizations: Groups of C57BL/6 mice (n=10) receive s.c. injections of OVA/PBS (as negative control), OVA/IFA (positive control), or OVA/CpG (positive control), and 3 different doses of OVA/DNA-NPs (1-100 µg/mouse), that demonstrate DC activation. Two to three weeks after the primary immunization, the animals receive a second "booster" immunization performed exactly as the first injections. Blood is obtained from mice at three time points: before immunization for base antibody levels, before the booster immunization and 1-2 weeks after the second "booster" immunization. Plasma IgG and IgM levels specific for the injected antigen is measured by direct ELISA using plates coated with antigen=OVA protein. The antibody results are determined in arbitrary units against an ELISA reference serum in order to reliable compare results obtained on different days. The type of immune response is evaluated by measuring the subclass antibody concentrations. In mouse, the production of IgG2a is recognized as characteristic of a Th1 response, whereas the production of IgG1 is characteristic of a Th2 response. Therefore, the assessment of the type of immune response is done by measuring IgG1, IgG2a and IgG2b levels by ELISA. The ratio of IgG2a/IgG1 antibody titers is used as indicator of Th bias.

The in vivo induced T cell responses is detected in vitro using the following assays: (1) Proliferation assays are performed by adding $OVA_{257-264}$ peptides (to stimulate CD8 T cells) and $OVA_{323-336}$ (to stimulate CD4 T cells), PBS/no peptide (negative control), or ConA (positive control) to splenocytes from immunized mice which contain T cells and antigen presenting cells, and measuring the uptake of [$^3$H]-thymidine after 4 d. (2) A Th2 response is also characterized by the secretion of Th2 type cytokines, such as IL-4, IL-5, whereas a Th1 type response is characterized by the secretion of IL-2 and IFN-$\gamma^{46-47}$. To measure type of T cell responses, splenocytes are set up as described herein using phorbol myristate acetate (PMA) and soluble anti-CD3, since ConA is not a very potent stimulus for Th2 cytokines. After 24 h the culture supernatants are assessed for IL-4, IL-2, IL-5, IL-10, TGF-$\alpha$ and IFN-$\gamma$ levels by ELISA. (3) IFN-$\gamma$ ELISPOT and intracellular flow cytometry assays (using brefeldin A to prevent leakage of the cytokines for the latter) for IL-4, IL-2 and IFN-$\gamma$ are used to measure the number of cytokine secreting T cells and double labeling for CD4 and CD8 to detect the type of T cells responding. (4) To measure the generation of functional CTL responses splenocytes are cultured in medium only and re-stimulated for with mitomycin C-treated (50 µg/ml) or irradiated B16-OVA cells and IL-2 for 6 days. As positive control splenocytes are stimulated with concavalin A (5 µg/ml). Expanded splenocytes are cultured with B16-OVA target cells and B16 (=negative control target cells), using a standard 4 h LDH assay.

Tumor Rejection Studies

Conditions that gave the strongest immune responses are used for tumor rejection studies. Prophylactic setting: _7 days after the final immunization C57/BL6 mice (10 per group) are challenged with 5×10$^5$ B16 cells s.c. and tumor growth are monitored as described herein. Therapeutic setting: C57/BL6 mice are inoculated with 5×10$^5$ B16 cells s.c. Once the tumors reach 3 mm in size, groups of mice (n=20) receive s.c. immunizations of OVA protein mixed with: PBS, or the DNA-NPs conditions that induced strongest immune responses. Half the mice from each group (n=10) are sacrificed 7 days after the final immunization to analyze immune responses and the other half are monitored for tumor progression.

Pharmacodynamics and Toxicity of DNA-NPs in vivo

Immunization experiments provide an opportunity to gain insight into the in vivo distribution and half life of the DNA-NPs, as well as any associated toxicity. Organs and blood are recovered from the sacrificed animals and tissue extracts prepared. DNA-NP are quantified by real time PCR to evaluate the biodistribution and circulating levels of the particles.

A powerful feature of the DNA-NP methods described herein is that the template sequence from which the particles are generated can be easily manipulated. One or more synthetic oligonucleotides can be used to build the template and beyond a minimum size of 60-80 bases, the RCA reaction proceeds equally well on templates regardless of size. Therefore, once discrete particle sequences are identified a hybrid template can be prepared by coupling the templates at the ligation step. Certain DC binding particles that show activity can be combined to further enhance their potency.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

What is claimed is:

1. A method of making a nanoparticle comprising:
   contacting a circular single-stranded nucleic acid template with a nucleic acid polymerase, wherein said template includes a module sequence which binds to a target molecule bound on the surface of an intact cell, wherein the module sequence in monovalent form has low affinity for the target molecule and in multivalent form binds to the target molecule with a high avidity; and
   amplifying said template with said polymerase to produce said nanoparticle, wherein said nanoparticle comprises a continuous strand of nucleic acid which folds into a ball conformation and comprises a concatamer of said module sequence.

2. The method of claim 1, wherein said nucleic acid template is DNA.

3. The method of claim 1, wherein said nucleic acid template is RNA.

4. The method of claim 1, wherein said nucleic acid polymerase is a strand displacing polymerase.

5. The method of claim 4, wherein said strand displacing polymerase is a DNA polymerase.

6. The method of claim 4, wherein said strand displacing polymerase is selected from the group consisting of phi29 polymerase, Klenow fragment, VENT® (Exo) DNA polymerase, 9° $N_m$ DNA polymerase, Bst DNA polymerase, M-MuLV reverse transcriptase, and AMV reverse transcriptase.

7. The method of claim 1, wherein said amplifying has a duration of more than 1 minute.

8. The method of claim 1, further comprising circularizing a linear nucleic acid template to produce said circular nucleic acid template.

9. The method of claim 8, wherein said linear nucleic acid template is more than 10 bases in length.

10. A non-naturally occurring nanoparticle made according to the method of claim 1.

11. The nanoparticle of claim 10, wherein said nucleic acid comprises DNA.

12. The nanoparticle of claim 11, wherein said DNA is more than 100 kb in length.

13. The nanoparticle of claim 11, wherein said DNA comprises a sequence encoding a sequence selected from a siRNA, reporter gene, therapeutic protein, and CpG sequence.

14. The nanoparticle of claim 10, further comprising a nucleic acid intercalating drug.

15. The nanoparticle of claim 10, further comprising an oligonucleotide-linked entity selected from the group consisting of an aptamer, drug, peptide, and siRNA.

16. A liposome comprising the nanoparticle of claim 10.

17. A pharmaceutical composition comprising the nanoparticle of claim 10.

18. A method of treating cancer comprising administering the pharmaceutical composition of claim 17 to a subject in need thereof.

19. A method for identifying nanoparticles comprising a module sequence capable of binding to a target molecule with high avidity comprising:
generating a library of nanoparticles comprising putative module sequences using the method of claim 1;
contacting said library to a target molecule; and
selecting for a nanoparticle that binds said target molecule, wherein the module sequence in monovalent form has low affinity for the target molecule and in multivalent form binds to the target molecule with a high avidity.

20. The method of claim 19, wherein said target molecule comprises a tumor cell.

21. A non-naturally occurring nanoparticle comprising a single-strand nucleic acid comprising a continuous strand of nucleic acid which folds into a ball conformation and comprises a concatameric module sequence which binds to a target molecule bound on the surface of an intact cell, wherein the module sequence in monovalent form has low affinity for the target molecule and in multivalent form binds to the target molecule with a high avidity.

22. The nanoparticle of claim 21, wherein said nucleic acid comprises DNA.

23. The nanoparticle of claim 22, wherein said DNA is more than 100 kb in length.

24. The nanoparticle of claim 22, wherein said DNA comprises a sequence encoding a sequence selected from a siRNA, reporter gene, therapeutic protein, and CpG sequence.

25. The nanoparticle of claim 21, further comprising a nucleic acid intercalating drug.

26. The nanoparticle of claim 21, further comprising an oligonucleotide-linked entity selected from the group consisting of an aptamer, drug, peptide, and siRNA.

27. A liposome comprising the nanoparticle of claim 21.

28. A pharmaceutical composition comprising the nanoparticle of claim 21.

29. A method of treating cancer comprising administering the pharmaceutical composition of claim 28 to a subject in need thereof.

30. A method of identifying a target comprising:
contacting said target with the nanoparticle of claim 21, wherein said module sequence selectively binds to said target; and
identifying binding of said module sequence to said target.

31. The method of claim 30, wherein said target is a tumor cell.

32. The method of claim 30, wherein said identifying binding comprises identifying a reporter moiety associated with said nanoparticle.

33. The nanoparticle of claim 21, wherein the single-strand nucleic acid comprises a plurality of concatameric sequences.

34. The nanoparticle of claim 33, wherein said plurality of concatameric sequences encode a plurality of module sequences.

35. A library of nanoparticles comprising at least two populations of nanoparticles, wherein said each of said at least two populations comprise nanoparticles comprising a single-strand nucleic acid comprising a continuous strand of nucleic acid which folds into a ball conformation and comprises a concatamer of at least one different module sequence which binds to a target molecule bound on the surface of an intact cell, wherein the module sequence in monovalent form has low affinity for the target molecule and in multivalent form binds to the target molecule with a high avidity.

36. The library of claim 35, wherein said plurality of concatameric sequences encode a plurality of aptamers module sequences.

37. The method of claim 1, wherein the target molecule comprises a protein.

38. The method of claim 19, wherein the target molecule comprises a protein.

39. The nanoparticle of claim 21, wherein the target molecule comprises a protein.

40. The library of claim 35, wherein the target molecule comprises a protein.

* * * * *

SEQUENCE LISTING

```
<160> NUMBER OF SEQ ID NOS: 15

<210> SEQ ID NO 1
<211> LENGTH: 105
<212> TYPE: DNA
<213> ORGANISM: Artificial Sequence
<220> FEATURE:
```

<223> OTHER INFORMATION: Primer, vector, or motif

<400> SEQUENCE: 1
gcgcggtaca tttgctggac tatgcatgtt cgtagttata taggggatt gtttgatagt     60 cggaaccgct gtgctcaaag tttggaggtt ggggatttga tgttg                    105

<210> SEQ ID NO 2
<211> LENGTH: 100
<212> TYPE: DNA
<213> ORGANISM: Artificial Sequence
<220> FEATURE:
<223> OTHER INFORMATION: Primer, vector, or motif

<400> SEQUENCE: 2 tgcttttgg aactcctgct agatgatgga atatcaaggc tgattaaacg gggcgtttcc    60
tgaaatgtat tacttgttga ggtgacgttg agttggatcc                          100

<210> SEQ ID NO 3
<211> LENGTH: 100
<212> TYPE: DNA
<213> ORGANISM: Artificial Sequence
<220> FEATURE:
<223> OTHER INFORMATION: Primer, vector, or motif

<400> SEQUENCE: 3 tgcttttgg aactcctgct tagcagtaag aaagtacaat ggggcgataa ccccaatcat    60
gactaaaaat atgattcgga ggtgacgttg agttggatcc                          100

<210> SEQ ID NO 4
<211> LENGTH: 100
<212> TYPE: DNA
<213> ORGANISM: Artificial Sequence
<220> FEATURE:
<223> OTHER INFORMATION: Primer, vector, or motif

<400> SEQUENCE: 4 tgcttttgg aactcctgct aaacaaaaga ggattgtatg gggcgtatca gttcgactat    60
ctggtagagc aaagaaaagt ggtgacgttg agttggatcc                          100

<210> SEQ ID NO 5
<211> LENGTH: 100
<212> TYPE: DNA
<213> ORGANISM: Artificial Sequence
<220> FEATURE:
<223> OTHER INFORMATION: Primer, vector, or motif

<400> SEQUENCE: 5 tgcttttgg aactcctgct aaccggaagt tcgtatggcc aaagctgatt aaaacggggc    60
gtttacacaa ggtgtatgtg ggtgacgttg agttggatcc                          100

<210> SEQ ID NO 6
<211> LENGTH: 120
<212> TYPE: DNA
<213> ORGANISM: Artificial Sequence
<220> FEATURE:
<223> OTHER INFORMATION: Primer, vector, or motif

<400> SEQUENCE: 6 tgcttttgg aactcctgct atagctgaag gatattggat cggggttgga tttacgattt    60
agatttgtta tgttctcttg ggtgacgttg agttggatcc ggtgacgttg agttggatcc   120

```
<210> SEQ ID NO 7
<211> LENGTH: 100
<212> TYPE: DNA
<213> ORGANISM: Artificial Sequence
<220> FEATURE:
<223> OTHER INFORMATION: Primer, vector, or motif
<220> FEATURE:
<221> NAME/KEY: misc_feature
<222> LOCATION: (0)...(0)
<223> OTHER INFORMATION: n = any nucleotide

<400> SEQUENCE: 7
tgcttttggg aactcctgct gaatagagaa caactaaatt ctgcaatgat gttgcgtagt     60
gactaangat caaatggggc ggtgacgttg agttggatcc                          100

<210> SEQ ID NO 8
<211> LENGTH: 100
<212> TYPE: DNA
<213> ORGANISM: Artificial Sequence
<220> FEATURE:
<223> OTHER INFORMATION: Primer, vector, or motif

<400> SEQUENCE: 8
tgcttttggg aactcctgct gatcaggtta taaagcgtta atagcttaat aaaacttgaa     60
aggtaataaa tggggcgtct ggtgacgttg agttggatcc                          100

<210> SEQ ID NO 9
<211> LENGTH: 100
<212> TYPE: DNA
<213> ORGANISM: Artificial Sequence
<220> FEATURE:
<223> OTHER INFORMATION: Primer, vector, or motif

<400> SEQUENCE: 9
tgcttttggg aactcctgct aaagagtacg aggtagaaat atgagaaact ttaaatttgt     60
ccagcagatc ctaatggggc ggtgacgttg agttggatcc                          100

<210> SEQ ID NO 10
<211> LENGTH: 100
<212> TYPE: DNA
<213> ORGANISM: Artificial Sequence
<220> FEATURE:
<223> OTHER INFORMATION: Primer, vector, or motif

<400> SEQUENCE: 10
tgcttttggg aactcctgct agacgttaga tgtatctgac cttacgactt caacttcctt    60
ctaaatctgc ccacaacgat ggtgacgttg agttggatcc                          100

<210> SEQ ID NO 11
<211> LENGTH: 100
<212> TYPE: DNA
<213> ORGANISM: Artificial Sequence
<220> FEATURE:
<223> OTHER INFORMATION: Primer, vector, or motif

<400> SEQUENCE: 11
tgcttttggg aactcctgct caacttgtgt cctcttgaaa gagtcggtca tacctataag    60
aatactttta tacagccaaa ggtgacgttg agttggatcc                          100

<210> SEQ ID NO 12
<211> LENGTH: 9
<212> TYPE: DNA
<213> ORGANISM: Artificial Sequence
<220> FEATURE:
```

```
<223> OTHER INFORMATION: Primer, vector, or motif

<400> SEQUENCE: 12 aatggggcg                                                                    9

<210> SEQ ID NO 13
<211> LENGTH: 105
<212> TYPE: DNA
<213> ORGANISM: Artificial Sequence
<220> FEATURE:
<223> OTHER INFORMATION: Primer, vector, or motif
<220> FEATURE:
<221> NAME/KEY: misc_feature
<222> LOCATION: (0)...(0)
<223> OTHER INFORMATION: n = a linker of 60 nucleotides

<400> SEQUENCE: 13
gcgcggtaca tttgctggac tannnnnnnn nnnnnnnnnn nnnnnnnnnn nnnnnnnnnn    60
nnnnnnnnnn nnnnnnnnnn nntggaggtt ggggatttga tgttg                  105

<210> SEQ ID NO 14
<211> LENGTH: 39
<212> TYPE: DNA
<213> ORGANISM: Artificial Sequence
<220> FEATURE:
<223> OTHER INFORMATION: Primer, vector, or motif

<400> SEQUENCE: 14
tccagcaaat gtaccgcgcc aacatcaaat ccccaacct                          39

<210> SEQ ID NO 15
<211> LENGTH: 22
<212> TYPE: DNA
<213> ORGANISM: Artificial Sequence
<220> FEATURE:
<223> OTHER INFORMATION: Primer, vector, or motif

<400> SEQUENCE: 15
gcgcggtaca tttgctggac ta                                            22
```